United States Patent
Kato et al.

(10) Patent No.: US 6,649,227 B2
(45) Date of Patent: Nov. 18, 2003

(54) DIFLUOROVINYL COMPOUND, LIQUID CRYSTAL COMPOSITION AND LIQUID CRYSTAL DISPLAY

(75) Inventors: Takashi Kato, Chiba (JP); Shuichi Matsui, Chiba (JP); Hiroyuki Takeuchi, Chiba (JP); Yasuhiro Kubo, Chiba (JP); Etsuo Nakagawa, Chiba (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 34 days.

(21) Appl. No.: 09/899,169

(22) Filed: Jul. 6, 2001

(65) Prior Publication Data

US 2002/0033472 A1 Mar. 21, 2002

(30) Foreign Application Priority Data

Jul. 7, 2000 (JP) ........................................ 2000-207243

(51) Int. Cl.$^7$ .................. C09K 19/34; C09K 19/30; C07D 319/06; C07C 25/13
(52) U.S. Cl. .............. 428/1.1; 252/299.61; 252/299.63; 252/299.66; 549/428; 549/356; 549/369; 549/370; 549/380; 570/128
(58) Field of Search ................ 428/1.1; 252/299.61; 252/299.63, 299.66; 570/128; 549/369, 370, 380, 428, 356

(56) References Cited

U.S. PATENT DOCUMENTS

| | | | |
|---|---|---|---|
| 4,877,548 A | | 10/1989 | Kitano et al. |
| 5,183,587 A | * | 2/1993 | Kitano et al. .......... 252/299.63 |
| 5,997,766 A | | 12/1999 | Kirsch et al. |

FOREIGN PATENT DOCUMENTS

EP      0 593 997     4/1994

* cited by examiner

Primary Examiner—Shean C. Wu
(74) Attorney, Agent, or Firm—McDermott, Will & Emery

(57) ABSTRACT

Provided are liquid crystalline compounds having a wide liquid crystal phase temperature range, low viscosity, a large elastic constant ratio $K_{33}/K_{11}$ and excellent solubility at low temperature, a liquid crystal composition using the same and a liquid crystal display. Preferred compounds are difluorovinyl compounds represented by Formula (1):

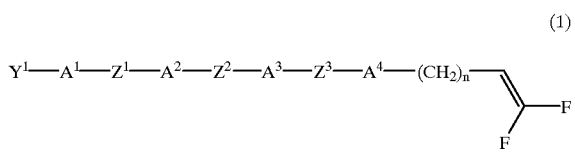

(1)

wherein $Y^1$, represents H or a straight chain or branched alkyl group having 1 to 10 carbon atoms, and optional —$CH_2$— in the above alkyl group may be replaced by —O— or —CH=CH—, but —O— is not adjacent to each other, and at least one H in $Y^1$ may be substituted with halogen or a cyano group: $A^1, A^2, A^3$ and $A^4$ each independently represent 1,4-cyclohexylene in which optional —$CH_2$— which is not adjacent to each other may be replaced by —O—, 1,4-phenylene in which optional H may be substituted with halogen, and a single bond, in which at least two of $A^1, A^2, A^3$ and $A^4$ have the ring structure described above, and at least one of them is 1,4-cyclohexylene in which —$CH_2$— is replaced by —O—; $Z^1$, $Z^2$ and $Z^3$ each independently represent a single bond, —$(CH_2)_2$—, —CH=CH—, —$(CH_2)_4$—, —O$(CH_2)_3$— or —$(CH_2)_3$O—; n represents 0 or an integer of 1 to 10, provided that when any of $A^1, A^2, A^3$ and $A^4$ is 1,4-phenylene, $Z^1, Z^2$ and $Z^3$ are single bonds, and among them, when $A^1$ is 1,3-dioxane-2,5-diyl and $A^2$ is 1,4-phenylene and when $A^3$ is 1,4-cyclohexylene and $A^4$ is a single bond, $Y^1$ is H, and n is not 0.

19 Claims, No Drawings

DIFLUOROVINYL COMPOUND, LIQUID CRYSTAL COMPOSITION AND LIQUID CRYSTAL DISPLAY

TECHNICAL FIELD

The present invention relates to a liquid crystalline compound and a liquid crystal composition. More specifically, it relates to a novel liquid crystalline compound which has a hetero ring structure and which has a difluorovinyl group at a terminal of the compound, a liquid crystal composition comprising the same, a liquid crystal display which is constituted with this liquid crystal composition and a synthetic intermediate for the liquid crystalline compound. In the present invention, the term of the liquid crystalline compound is used as a general term of a compound showing a liquid crystal phase and a compound that does not show a liquid crystal phase but is useful as a structural component for a liquid crystal composition.

BACKGROUND ART

Many display elements making use of characteristics of a nematic liquid crystal compound have so far been produced. In recent years, a liquid crystal display (LCD) is widely used for various uses including not only watches and portable electric calculators but also monitors for personal computers and portable telephones, and demand therefor has been growing large year by year. In accordance with it, improvement items for performances required for LCD have come to extend over many divergences such as an expansion in an operable temperature range, a shift to high density and coloring of the display, an acceleration in response and an expansion in a viewing angle. It is known that various display modes using electro-optical effects, such as a DS (dynamic scattering) mode, a TN (twist nematic) mode, a GH (guest host) mode, an STN (super twist nematic) mode, an IPS (in-plane switching) mode and a VA (vertical alignment) mode have been proposed in order as means for solving them.

In such situation, various characteristics are required to a liquid crystal composition used for LCD according to the respective display modes. First, the physical property values such as optical anisotropy ($\Delta n$), dielectric anisotropy ($\Delta \epsilon$), viscosity ($\eta$), conductivity and elastic constant ratio $K_{33}/K_{11}$ ($K_{33}$: bend elastic constant and $K_{11}$: spray elastic constant) of a liquid crystal composition are required to have values which are optimum for a display mode and a form of an element. In LCD may be used in outdoor at low temperature as a portable telephone and a mobile personal computer, a liquid crystal composition that is stably operated at low temperature is required. In order to meet this, a liquid crystalline compound constituting it has to be excellent in solubility at low temperature. Further, a portable telephone tends to be always increased, though it has a small display, in an information amount displayed thereon, so that display having high contrast is desired. In an STN mode that is mainly used for the LCD, a liquid crystalline compound having a high $K_{33}/K_{11}$ value is required in order to obtain high contrast ratio. Further, in order to achieve quick response in any of the LCD's shown above, a liquid crystal composition having low viscosity is required, and a liquid crystalline compound has to be indispensably reduced as well in viscosity. In addition thereto, given as common items of characteristics required to a liquid crystal composition are stability against moisture, light, heat and air that are usually present under use environment and stability against an electric field and electromagnetic irradiation. Further, the respective components of a liquid crystalline compound constituting a liquid crystal composition have to be chemically stable to each other in a use environment, and it is important as well that they have good solubility with each other.

In the existing state, however, it is very difficult to solve these problems only with the existing liquid crystal compounds and liquid crystal compositions, and it is an urgent matter to develop a novel liquid crystalline compound and liquid crystal composition which can meet the various requirements described above.

SUMMARY OF THE INVENTION

An object of the present invention is to provide a liquid crystalline compound which has particularly a wide liquid crystal phase temperature range, low viscosity, a large elastic constant ratio $K_{33}/K_{11}$ and solubility improved at low temperature so that the problems of conventional techniques can be overcome, a liquid crystal composition comprising the same, a liquid crystal display which is constituted with the above liquid crystal composition and an intermediate useful for producing the liquid crystalline compound having excellent characteristics.

In order to achieve the objects described above, the following inventions are claimed for the grant of a patent in the present application.

(1) A difluorovinyl compound represented by Formula (1):

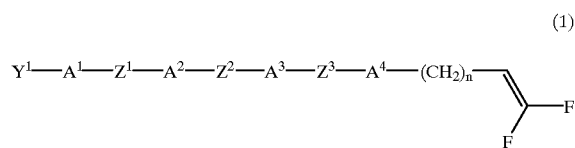

(1)

wherein $Y^1$ represents H or straight chain or branched alkyl group having 1 to 10 carbon atoms, and optional —$CH_2$— in the above alkyl group may be replaced by —O— or —CH=CH—, but —O— is not adjacent to each other, and at least one H in $Y^1$ may be substituted with halogen or a cyano group; $A^1$, $A^2$, $A^3$ and $A^4$ each independently represent 1,4-cyclohexylene in which optional —$CH_2$— which is not adjacent to each other may be replaced by —O—, 1,4-phenylene in which optional H may be substituted with halogen, and a single bond, in which at least two of $A^1$, $A^2$, $A^3$ and $A^4$ have the ring structure described above, and at least one of them is 1,4-cyclohexylene in which —$CH_2$— is replaced by —O—; $Z^1$, $Z^2$ and $Z^3$ each independently represent a single bond, —$(CH_2)_2$—, —CH=CH—, —$(CH_2)_4$—, —$O(CH_2)_3$— or —$(CH_2)_3O$—; n represents 0 or an integer of 1 to 10, provided that when any of $A^1$, $A^2$, $A^3$ and $A^4$ is 1,4-phenylene, $Z^1$, $Z^2$ and $Z^3$ are single bonds, and among them, when $A^1$ is 1,3-dioxane-2,5-diyl and $A^2$ is 1,4-phenylene and when $A^3$ is 4,cyclohexylene and $A^4$ is a single bond, $Y^1$ is H, and n is not 0.

(2) A difluorovinyl compound as described in the above item [1], wherein $A^1$, $A^2$, $A^3$ and $A^4$ each independently represent 1,4-cyclohexylene in which optional —$CH_2$— which is not adjacent to each other may be replaced by —O—, 1,4-phenylene and a single bond, in which at least two of $A^1$, $A^2$, $A^3$ and $A^4$ have the ring structure described above, and at least one of them is 1,4-cyclohexylene in which —$CH_2$— is replaced by —O—; $Z^1$, $Z^2$ and $Z^3$ each independently represent a single bond, —$(CH_2)_2$— or —$(CH_2)_4$—, provided that when any of $A^1$, $A^2$, $A^3$ and $A^4$ is 1,4-phenylene, $Z^1$, $Z^2$ and $Z^3$ are single bonds, and among them, when $A^1$ is 1,3-dioxane-2,5-diyl and $A^2$ is 1,4-phenylene and when $A^3$ is 1,4-cyclohexylene and $A^4$ is a single bond, $Y^1$ is H, and n is not 0.

(3) A difluorovinyl compound as described in the above item (1), wherein $A^1$ is 1,3-dioxane-2,5-diyl; $A^2$ is 1,4-cyclohexylene; and $A^3$, $A^4$, $Z^1$, $Z^2$ and $Z^3$ are single bonds.

(4) A difluorovinyl compound as described in the above item (1), wherein either one of $A^1$ and $A^2$ is 1,3-dioxane-2,5-diyl, and the other is 1,4-cyclohexylene; $A^3$ is 1,4-cyclohexylene; and $A^4$, $Z^1$, $Z^2$ and $Z^3$ are single bonds.

(5) A difluorovinyl compound as described in the above item (1), wherein either one of $A^1$, $A^2$ and $A^3$ is 1,3-dioxane-2,5-diyl, and the remaining two are 1,4-cyclohexylenes; $A^4$ is 1,4-cyclohexylene; and $Z^1$, $Z^2$ and $Z^3$ are single bonds.

(6) A difluorovinyl compound as described in the above item (1), wherein $A^1$ is 1,3-dioxane-2,5-diyl; $A^2$ is 1,4-cyclohexylene; $Z^1$ is —(CH$_2$)$_2$— or —(CH$_2$)$_4$—; and $A^3$, $A^4$, $Z^2$ and $Z^3$ are single bonds.

(7) A difluorovinyl compound as described in the above item (1), wherein either one of $A^1$ and $A^2$ is 1,3-dioxane-2,5-diyl, and the other is 1,4-cyclohexylene; $A^3$ is 1,4-cyclohexylene; either one of $Z^1$ and $Z^2$ is —(CH$_2$)$_2$— or —(CH$_2$) 4-, and the other is a single bond; and $A^4$, $Z^1$, $Z^2$ and $Z^3$ are single bonds.

(8) A difluorovinyl compound as described in the above item (1), wherein either one of $A^1$, $A^2$ and $A^3$ is 1,3-dioxane-2,5-diyl, and the remaining two are 1,4-cyclohexylenes; $A^4$ is 1,4-cyclohexylene; and either one of $Z^1$, $Z^2$ and $Z^3$ is —(CH$_2$)$_2$— or —(CH$_2$)$_4$—, and the remaining two are single bonds.

(9) A liquid crystal composition comprising at least one difluorovinyl compound as described in any of the above items (1) to (8).

(10) A liquid crystal composition comprising at least one difluorovinyl compound as described in any of the above items (1) to (8) as a first component and at least one compound selected from the group consisting of compounds represented by Formulas (2), (3) and (4) as a second component:

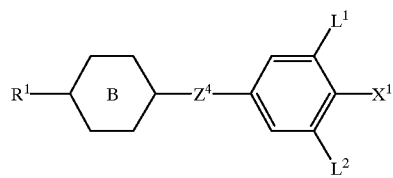

(2)

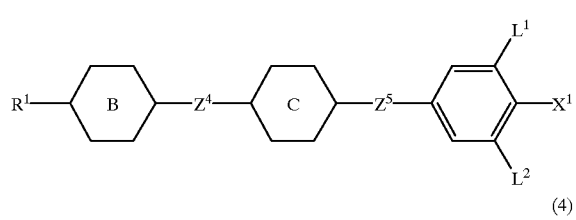

(3)

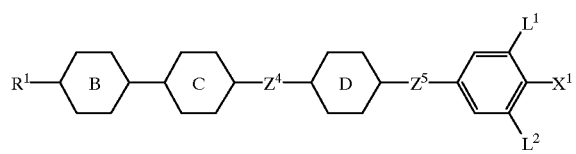

(4)

wherein $R^1$ represents an alkyl group having 1 to 10 carbon atoms, in which optional —C$_2$— in this alkyl group may be replaced by —O— or —C=CH—, but —O— is not adjacent to each other and in which optional H in this group may be substituted with F; $X^1$ represents F, Cl, —OCF$_3$, —OCF$_2$H, —CF$_3$, —CF$_2$H, —CFH$_2$, —OCF$_2$CF$_2$H or —OCF$_2$CF=CF$_3$; $L^1$ and $L^2$ each independently represent H or F; $Z^4$ and $Z^5$ each independently represent —(CH$_2$)$_2$—, —(CH$_2$)$_4$—, —COO—, —CF$_2$O—, —OCF$_2$—, —C=CH— or a single bond; a ring B and a ring C each independently represent 1,4-cyclohexylene, 1,3-dioxane-2,5-diyl or 1,4-phenylene in which H may be substituted with F; and a ring D represents 1,4-cyclohexylene or 1,4-phenylene in which H may be substituted with F.

(11) A liquid crystal composition comprising at least one difluorovinyl compound as described in any of the above items (1) to (8) as the first component and at least one compound selected from the group consisting of compounds represented by Formulas (5) and (6) as a second component:

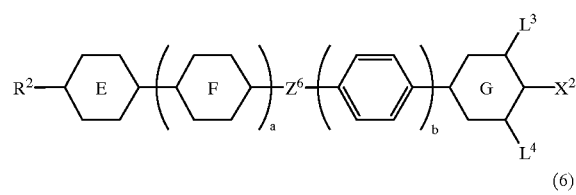

(5)

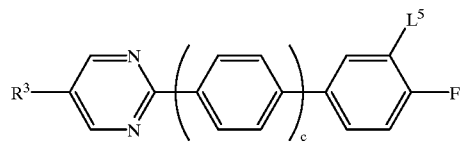

(6)

wherein $R^2$ and $R^3$ each independently represent an alkyl group having 1 to 10 carbon atoms, in which optional —C$_2$— in these alkyl groups may be replaced by —O— or —C=CH—, but —O— is not adjacent to each other and in which optional H in these alkyl groups may be substituted with F; $X^2$ represents —CN or —C≡C— CN; a ring E represents 1,4-cyclohexylene, 1,4-phenylene, 1,3-dioxane-2,5-diyl or pyrimidine-2,5-diyl; a ring F represents 1,4-cyclohexylene, 1,4-phenylene in which H may be substituted with F or pyrimidine-2,5-diyl; a ring G represents 1,4-cyclohexylene or 1,4-phenylene; $Z^6$ represents —(CH$_2$)$_2$—, —COO—, —CF$_2$O—, —OCF$_2$— or a single bond; $L^3$, $L^4$ and $L^5$ each independently represent H or F; and a, b and c each independently represent 0 or 1.

(12) A liquid crystal composition comprising at least one difluorovinyl compound as described in any of the above items (1) to (8) as the first component and at least one compound selected from the group consisting of compounds represented by Formulas (7), (8) and (9) as a second component:

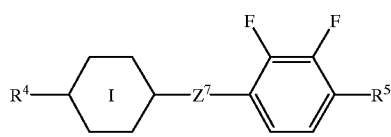

(7)

-continued (8)

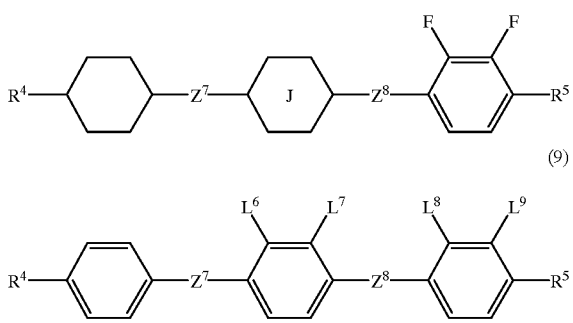

(9)

wherein $R^4$ and $R^5$ each independently represent an alkyl group having 1 to 10 carbon atoms, in which optional —$C_2$— in this alkyl group may be replaced by —O— or —C=CH—, but —O— is not adjacent to each other and in which optional H in this alkyl group may be substituted with F; a ring I and a ring J each independently represent 1,4-cyclohexylene or 1,4-phenylene; $L^6$, $L^7$, $L^8$ and $L^9$ each independently represent H or F, but all are not H at the same time; and $Z^7$ and $Z^8$ each independently represent —($CH_2)_2$—, —COO— or a single bond.

(13) A liquid crystal composition comprising at least one difluorovinyl compound as described in any of the above items (1) to (8) as the first component, at least one compound selected from the group consisting of the compounds represented by Formulas (2), (3) and (4) as the second component and at least one compound selected from the group consisting of compounds represented by Formulas (10), (11) and (12) as a third component:

(10)

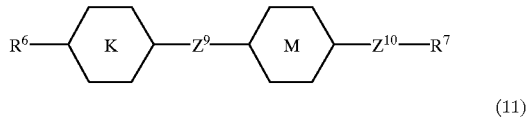

(11)

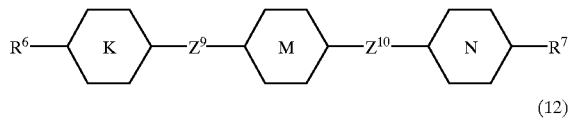

(12)

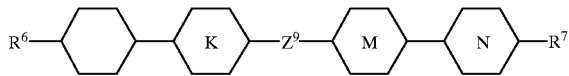

wherein $R^6$ and $R^7$ each independently represent an alkyl group having 1 to 10 carbon atoms, in which optional —$C_2$— in this alkyl group may be replaced by —O— or —C=CH—, but —O— is not adjacent to each other and in which optional H in this alkyl group may be substituted with F; a ring K, a ring M and a ring N each independently represent 1,4-cyclohexylene, pyrimidine-2,5-diyl or 1,4-phenylene in which H may be substituted with F; and $Z^9$ and $Z^{10}$ each independently represent —C≡C—, —COO—, —($CH_2)_2$—, —C—C— or a single bond.

(14) A liquid crystal composition comprising at least one difluorovinyl compound as described in any of the above items (1) to (8) as the first component, at least one compound selected from the group consisting of the compounds represented by Formulas (5) and (6) as the second component and at least one compound selected from the group consisting of the compounds represented by Formulas (10), (11) and (12) as the third component.

(15) A liquid crystal composition comprising at least one difluorovinyl compound as described in any of the above items (1) to (8) as the first component, at least one compound selected from the group consisting of the compounds represented by Formulas (7), (8) and (9) as the second component and at least one compound selected from the group consisting of the compounds represented by Formulas (10), (11) and (12) as the third component.

(16) A liquid crystal composition comprising at least one difluorovinyl compound as described in any of the above items (1) to (8) as the first component, at least one compound selected from the group consisting of the compounds represented by Formulas (2), (3) and (4) as the second component, at least one compound selected from the group consisting of the compounds represented by Formulas (5) and (6) as the third component and at least one compound selected from the group consisting of the compounds represented by Formulas (10), (11) and (12) as a fourth component.

(17) A liquid crystal composition comprising at least one liquid crystal composition as described in any of the items (9) to (16) and further comprising at least one optically active compound.

(18) A liquid crystal display constituted with the liquid crystal composition as described in any of the items (9) to (17).

(19) A difluorovinyl compound represented by Formula (13):

(13)

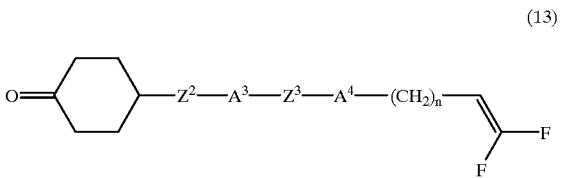

wherein $A^3$ and $A^4$ each independently represent 1,4-cyclohexylene in which optional —$CH_2$— may be replaced by —O—, 1,4-phenylene in which optional H may be substituted with halogen, and a single bond; $Z^2$ and $Z^3$ each independently represent a single bond, —($CH_2)_2$—, —CH=CH—, ($CH_2)_4$—, —O($CH_2)_3$— or ($CH_2)_3O$; and n represents 0 or an integer of 1 to 10.

The compound of the present invention represented by Formula (1) is a dicyclic to tetracyclic compound that has a hetero ring having an oxygen atom and a difluorovinyl group together in a skeleton.

A compound having a difluorovinyl group is disclosed in, for example, Japanese Patent Application Laid-Open No. 308239/1989. However, a compound having a skeleton containing a hetero ring such as a dioxane ring and a difluorovinyl group at the same time as is the case with the present invention is not described therein. Also, a compound formed from a dioxane ring and a difluorovinyloxy group is described in, for example, U.S. Pat. No. 5,997,766. However, reference to description in which the characteristics of the above compound are introduced in Abstract in Freiburger Arbeitstagung Flussigkristalle held in Mar. 25 through 27, 1998 shows that a problem is involved in a chemical stability thereof. Further, a compound having a dioxane ring and a difluorovinyloxy group at the same time is described in EP 593997, but it is shown merely as a synthetic intermediate, and usefulness thereof as a liquid crystalline compound as is the case with the present invention is not shown.

The liquid crystalline compound of the present invention is characterized not only by that it is physically and chemically very stable under conditions on which a display is used but also that it has a wide liquid crystal phase temperature range, good solubility in a liquid crystal composition even at low temperature, low viscosity, suitable dielectric anisotropy and a large elastic constant ratio $K_{33}/K_{11}$. Among the molecule-structural elements, the ring structure and the structure of the bonding group or the side chain are suitably selected, whereby the desired physical values can optionally be controlled. The preferred compounds shall be shown below.

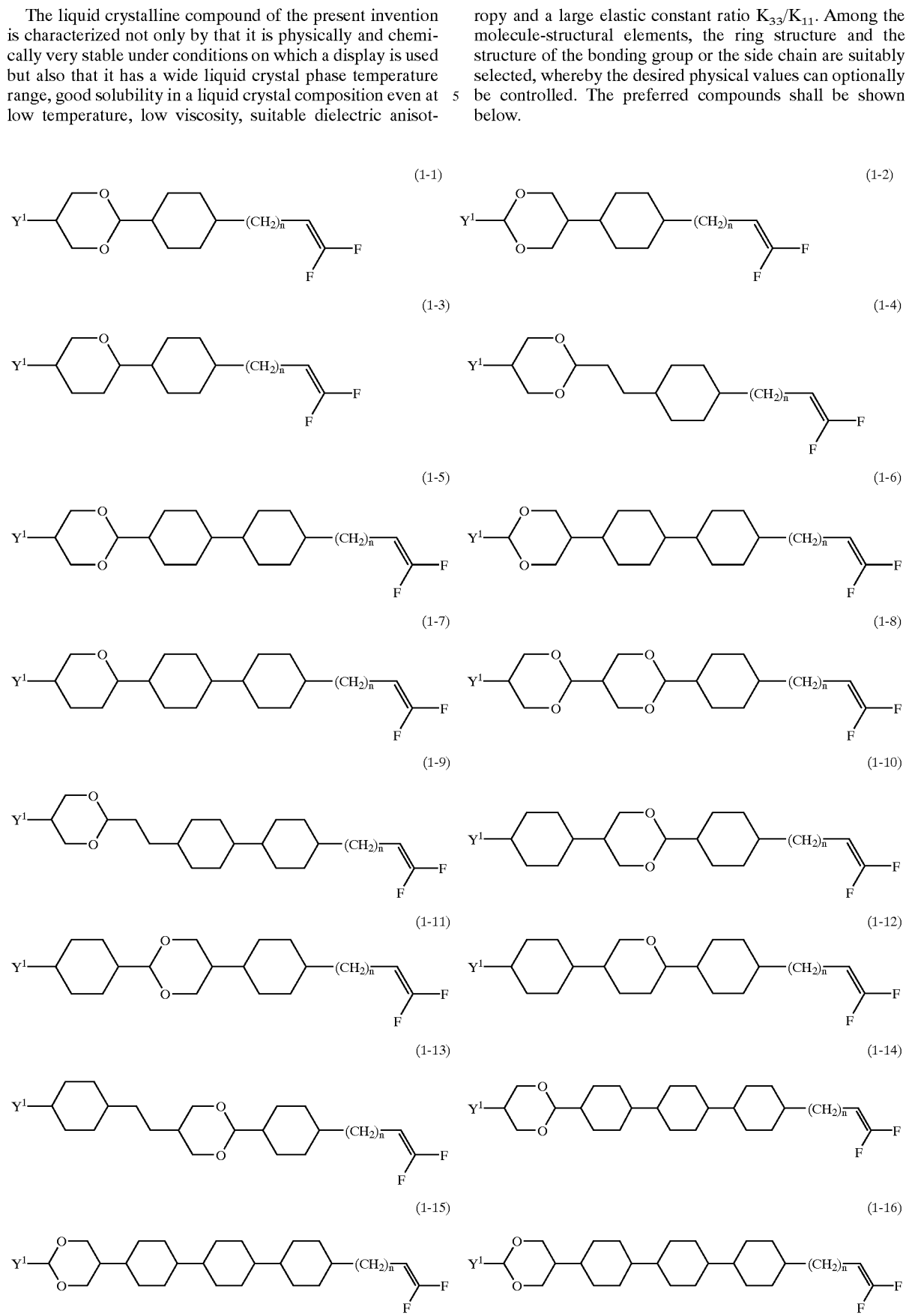

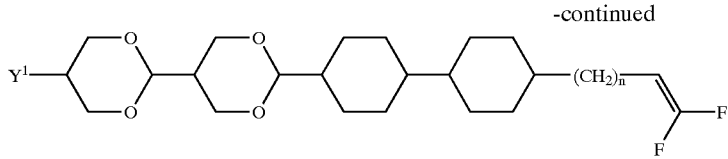

(1-17)

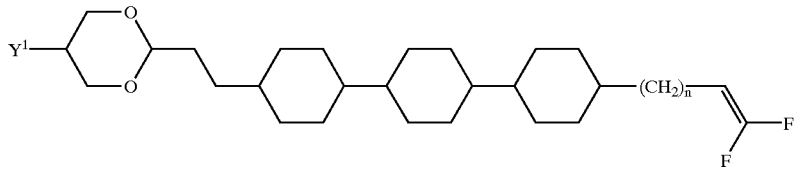

(1-18)

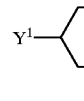

(1-19)

(1-20)

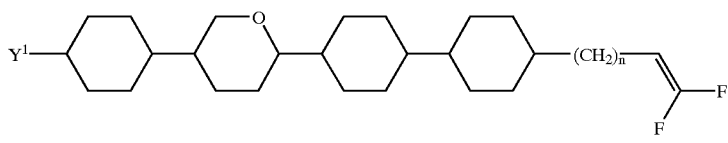

(1-21)

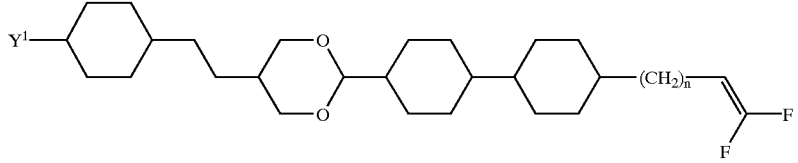

(1-22)

($Y^1$ and n are the same as those described above).

Among the compounds described above, the dicyclic compounds of (1-1) to (1-4) have positive dielectric anisotropy and show a large elastic constant ratio $K_{33}/K_1$ and low viscosity. When used for a liquid crystal composition, these characteristics are reflected on the characteristics of the liquid crystal composition, and it has the advantage that only the viscosity is reduced without particularly lowering the clearing point. The tricyclic compounds of (1-5) to (1-13) have the same characteristics as those of the dicyclic compounds, and when used for a liquid crystal composition, the clearing point can be set up high. Further, the tetracyclic compounds of (1-14) to (1-22) have a high clearing point and a positive dielectric anisotropy and show a large elastic constant ratio $K_{33}/K_{11}$. They have a relatively low viscosity though they are tetracyclic compounds and can be increased in a clearing point while maintaining the viscosity of the liquid crystal composition.

Further, the following ones can be given as preferred $Y^1$ in the compounds described above.

It includes an alkyl group having 1 to 10 carbon atoms, an alkoxy group, an alkoxyalkyl group, an alkenyl group, an alkenyloxy group, an alkenyloxyalkyl group and an alkyloxyalkenyl group. Among them, the particularly preferred groups include methyl, ethyl, propyl, butyl, pentyl, hexyl, heptyl, octyl, methoxy, ethoxy, propoxy, butoxy, pentyloxy, hexyloxy, heptyloxy, octyloxy, methoxymethyl, ethoxymethyl, propoxymethyl, butoxymethyl, methoxyethyl, ethoxyethyl, propoxyethyl, methoxypropyl, ethoxypropyl, propoxypropyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 4-pentenyloxy, methoxy-1-propenyl, methoxy-1-pentenyl methoxy-3-pentenyl and so on. The compounds in which $Y^1$ is an optically active group are particularly useful as a chiral dopant. Use thereof can prevent reverse twist domains from being produced.

Further, the compounds of the present invention show the same characteristics also when they are substituted in structural atoms thereof with isotopes, and therefore they are preferred as well.

The liquid crystal composition of the present invention shall be explained below. The liquid crystal composition of the present invention preferably contains 0.1 to 99.9% by weight of at least one compound represented by Formula (1) in order to allow excellent characteristics to be revealed, and a content thereof is more preferably 1 to 80% by weight and further preferably 1 to 60% by weight.

The liquid crystal composition provided by the present invention may comprise only the first component containing at least one liquid crystalline compound represented by Formula (1), and preferred is the compound comprising as the second component, in addition thereto, at least one compound (hereinafter referred to as a second A component) selected from the group consisting of the compounds represented by Formulas (2), (3) and (4) described above and/or at least one compound (hereinafter referred to as a second B component) selected from the group consisting of the compounds represented by Formulas (5) and (6). Further, the composition can contain as well at least one compound selected from the group consisting of the compounds represented by Formulas (10), (11) and (12) as the third component for the purpose of controlling a threshold voltage, a liquid crystal temperature range, optical anisotropy, dielectric anisotropy and viscosity.

Further, the respective components of the liquid crystal composition used for the present invention have no large difference between the physical characteristics, and therefore they may be analogues comprising isotopic elements of the respective elements.

In the second A component described above, capable of being given respectively are the compounds of formulas (2-1) to (2-9) as suitable examples of the compound represented by Formula (2), the compounds of formulas (3-1) to (3-97) as suitable examples of the compound represented by Formula (3) and the compounds of formulas (4-1) to (4-33) as suitable examples of the compound represented by Formula (4).

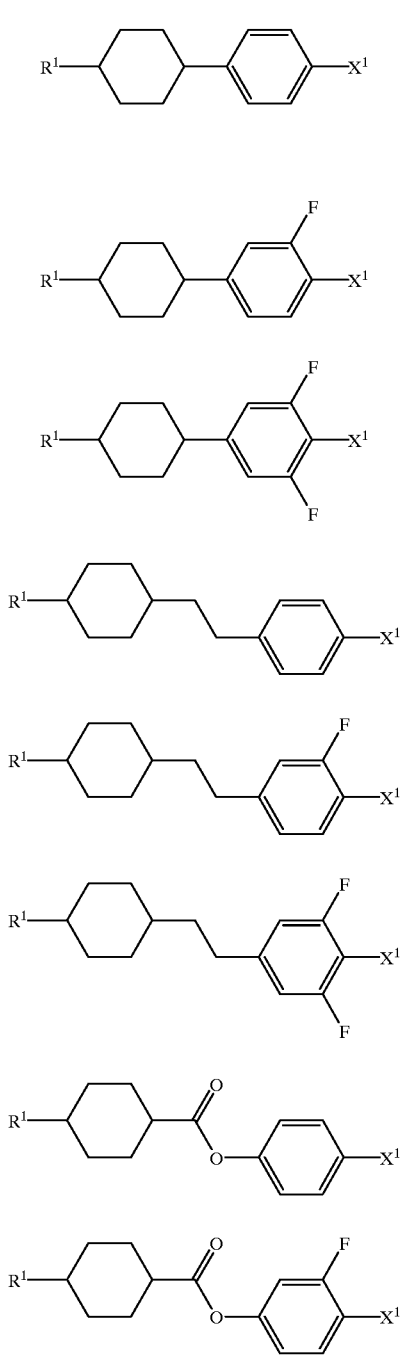

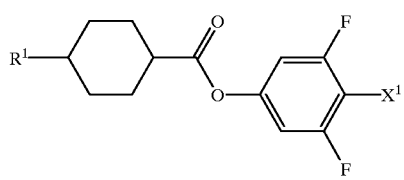

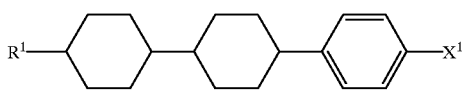

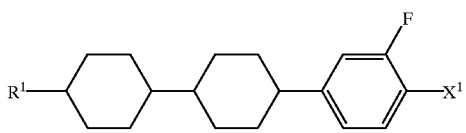

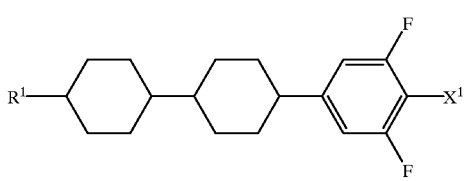

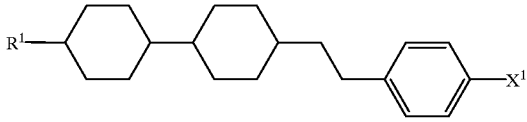

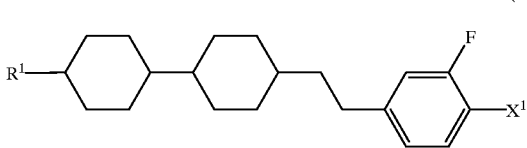

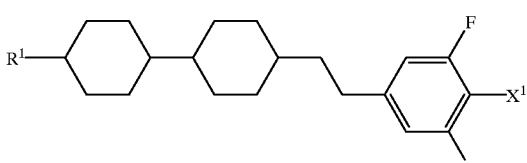

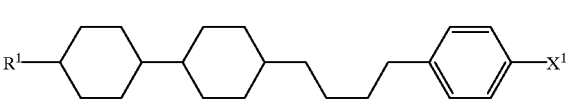

(3-8)
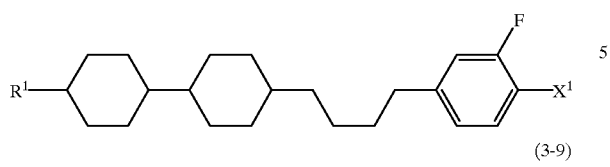
(3-9)
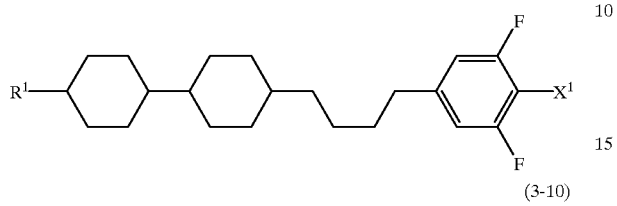
(3-10)
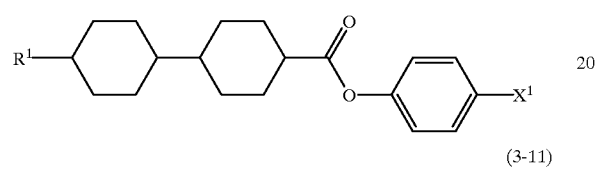
(3-11)
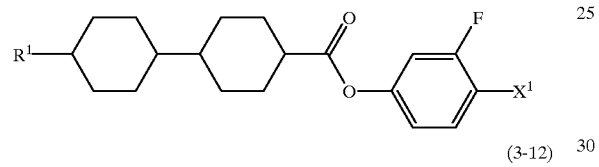
(3-12)
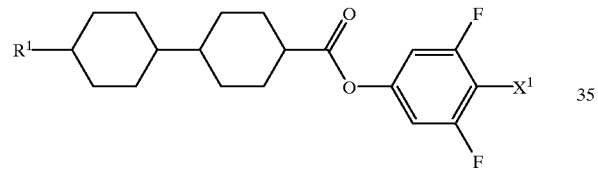
(3-13)
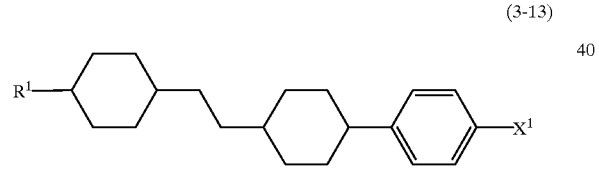
(3-14)
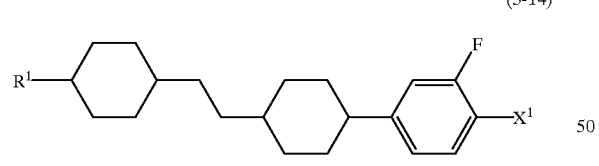
(3-15)
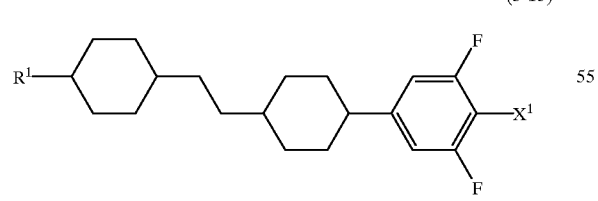
(3-16)
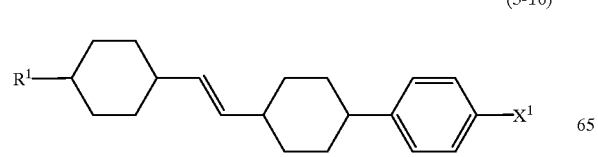
(3-17)
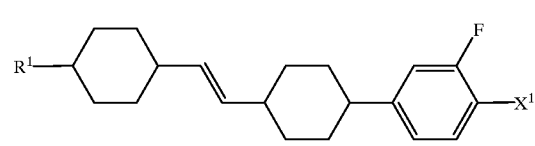
(3-18)
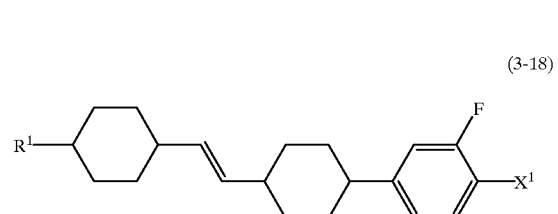
(3-19)
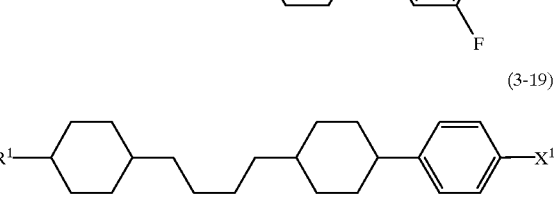
(3-20)
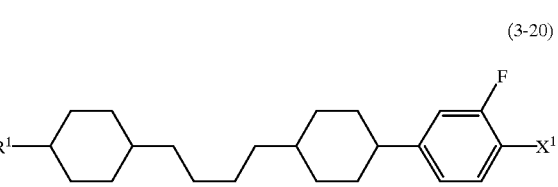
(3-21)
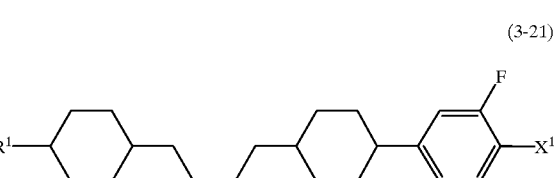
(3-22)
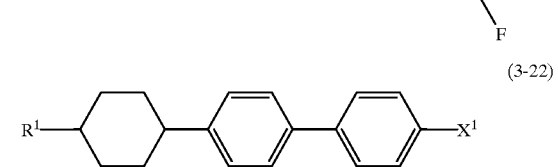
(3-23)
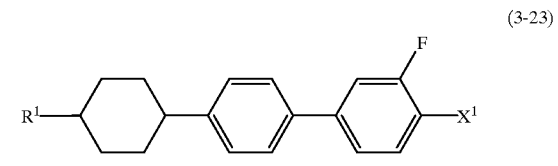
(3-24)
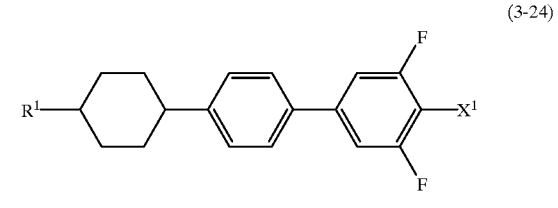
(3-25)
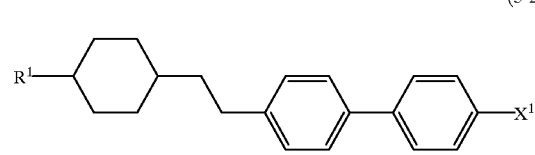

(3-26) 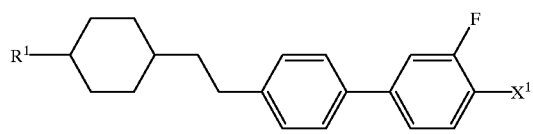
(3-27) 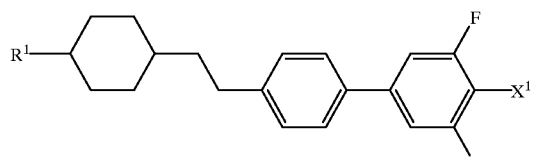
(3-28) 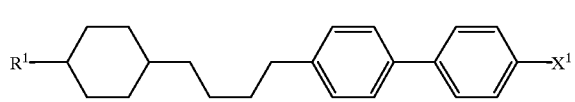
(3-29) 
(3-30) 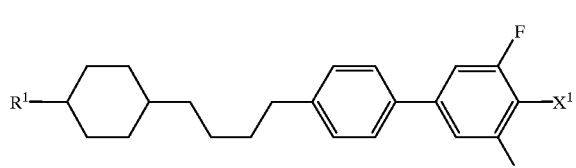
(3-31) 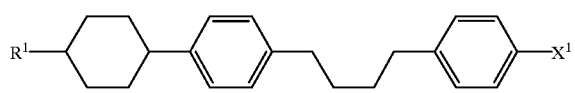
(3-32) 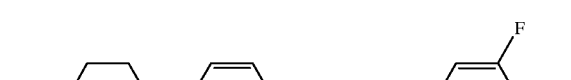
(3-33) 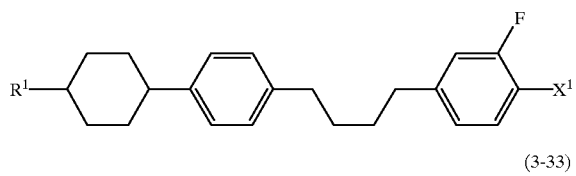
(3-34) 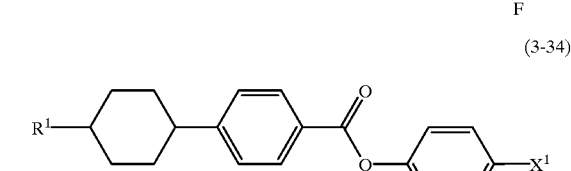
(3-35) 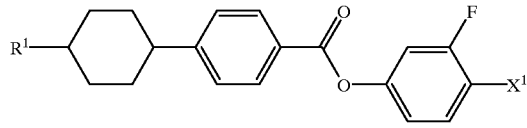
(3-36) 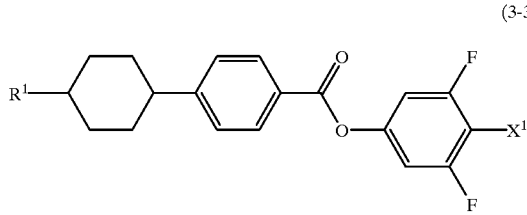
(3-37) 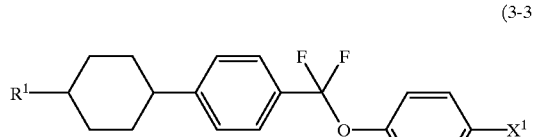
(3-38) 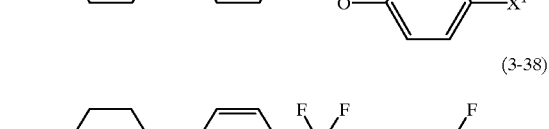
(3-39) 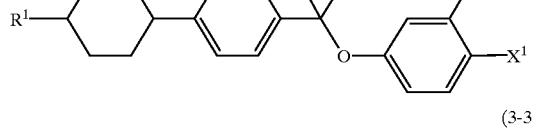
(3-40) 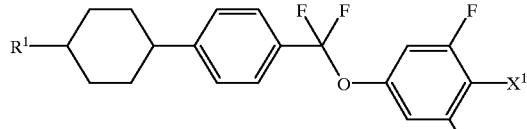
(3-41) 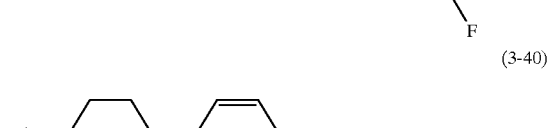
(3-42) 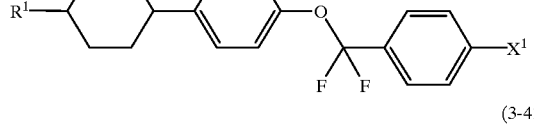
(3-43) 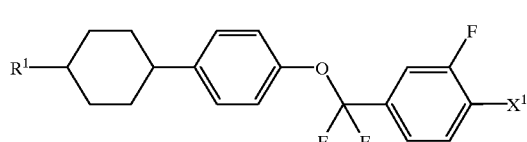

(3-44) 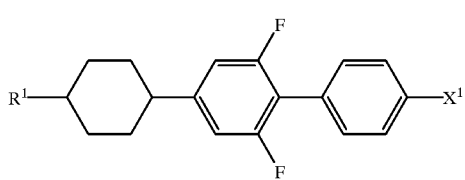
(3-45) 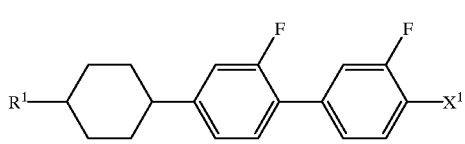
(3-46) 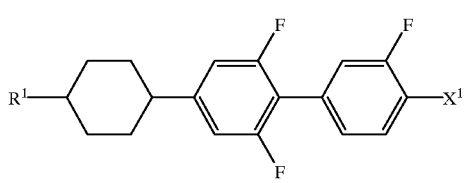
(3-47) 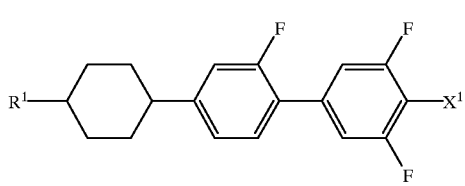
(3-48) 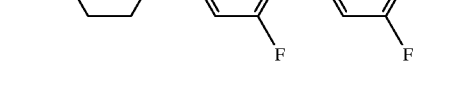
(3-49) 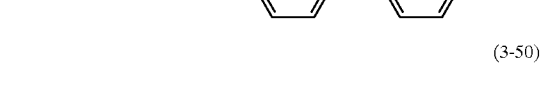
(3-50) 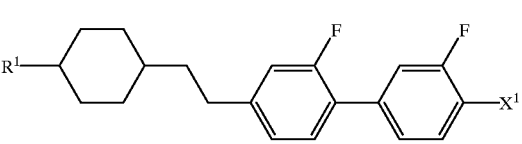
(3-51)
(3-52) 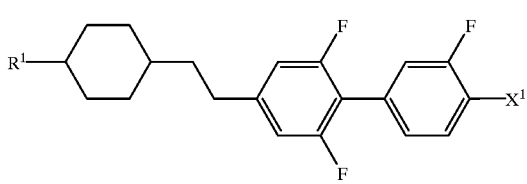
(3-53) 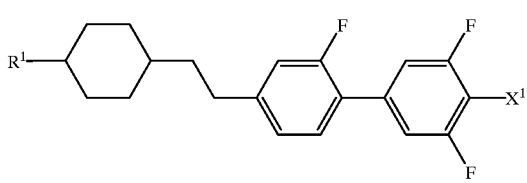
(3-54) 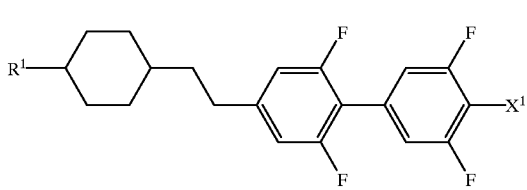
(3-55) 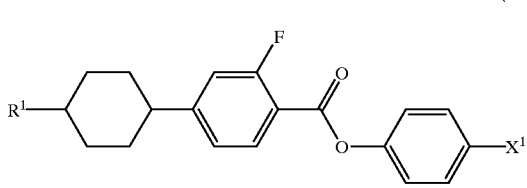
(3-56) 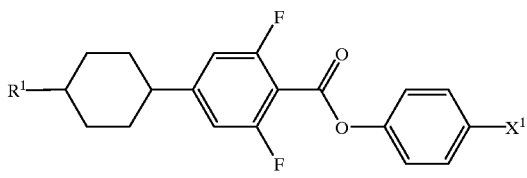
(3-57) 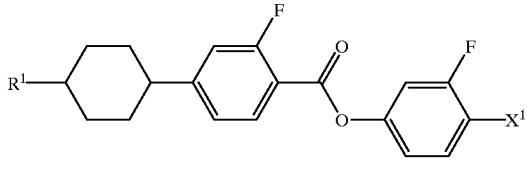
(3-58) 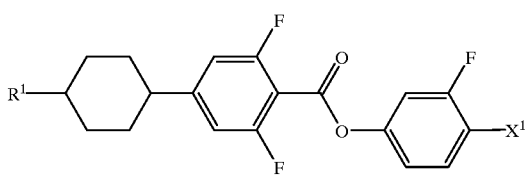

(3-59) 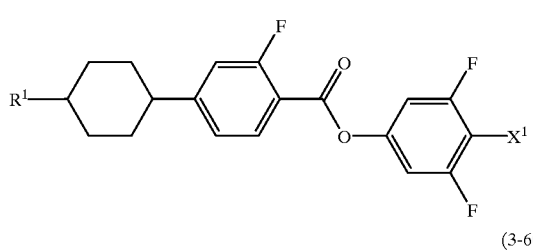
(3-60) 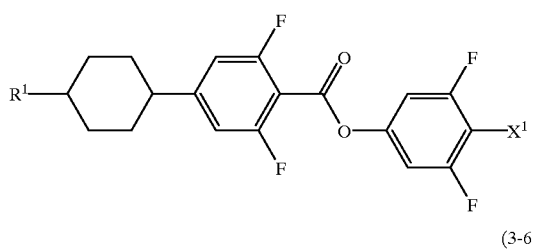
(3-61) 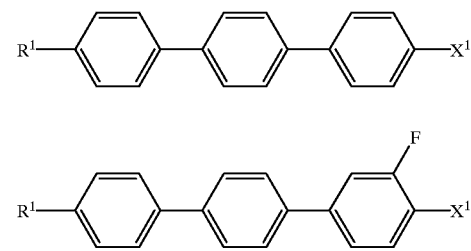
(3-62) 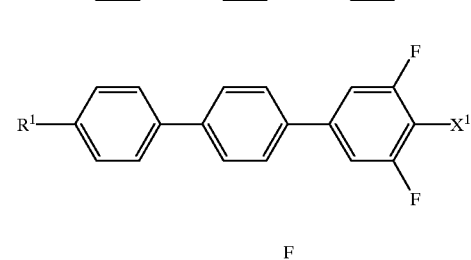
(3-63) 
(3-64) 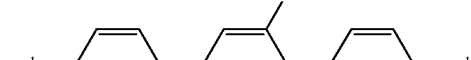
(3-65) 
(3-66) 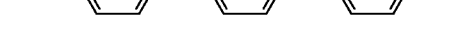
(3-67) 
(3-68) 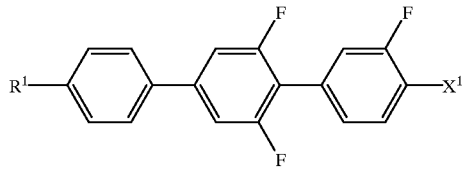
(3-68) 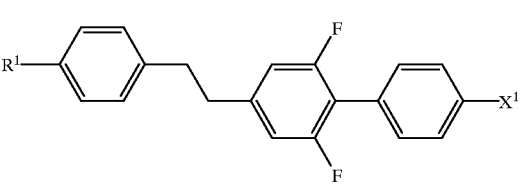
(3-70) 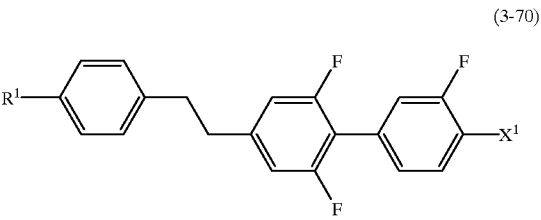
(3-71) 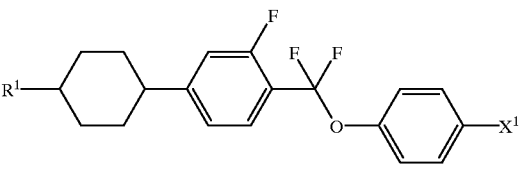
(3-72) 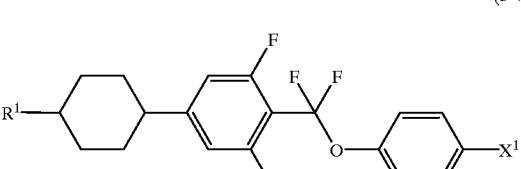
(3-73) 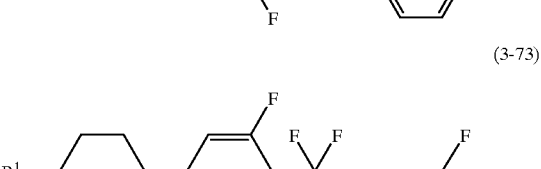
(3-74) 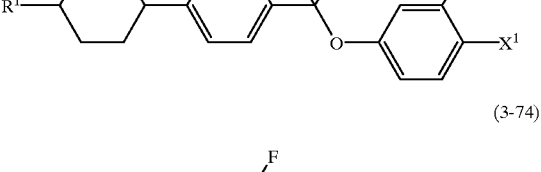

(3-75)
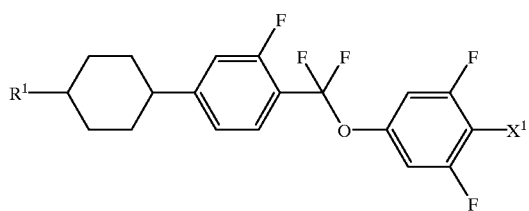
(3-76)
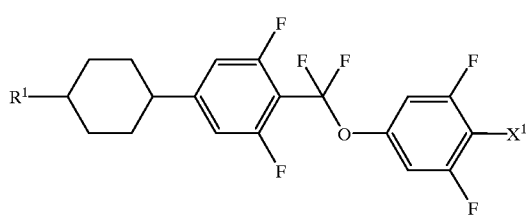
(3-77)
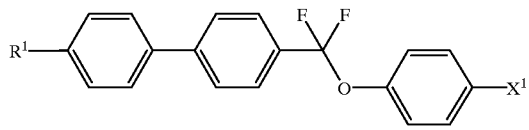
(3-78)
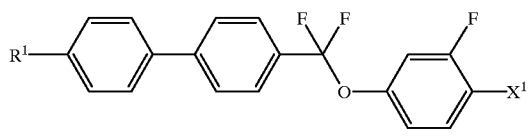
(3-79)
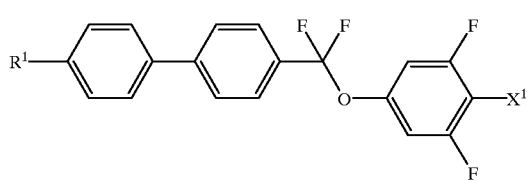
(3-80)
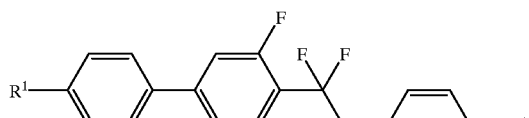
(3-81)
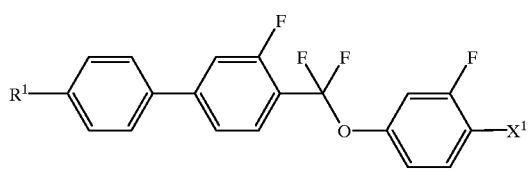
(3-82)
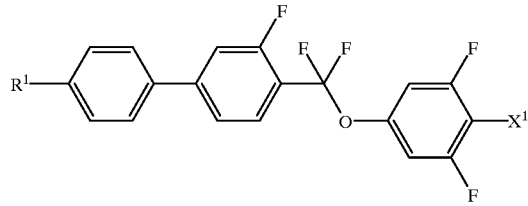
(3-83)
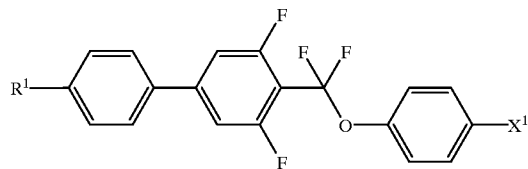
(3-84)
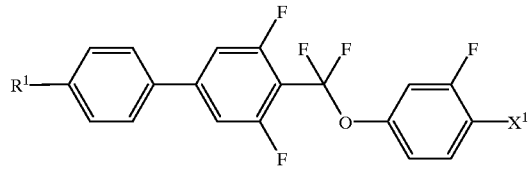
(3-85)
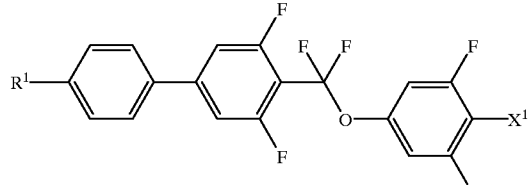
(3-86)
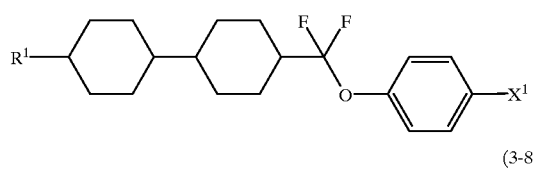
(3-87)
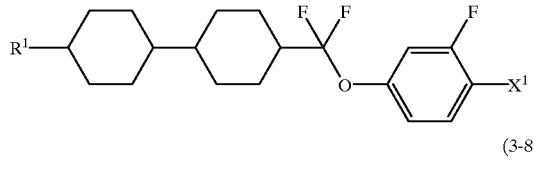
(3-88)
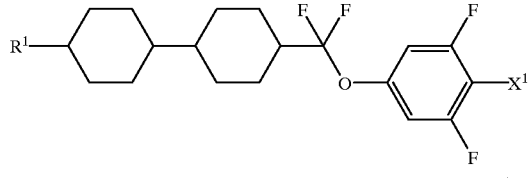
(3-89)
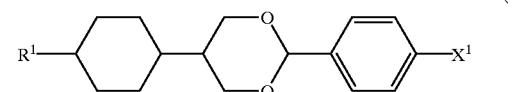

(3-90)
(3-91)
(3-92)
(3-93)
(3-94)
(3-95)
(3-96)
(3-97)
(4-1)
(4-2)
(4-3)
(4-4)
(4-5)
(4-6)
(4-7)
(4-8)
(4-9)
(4-10)

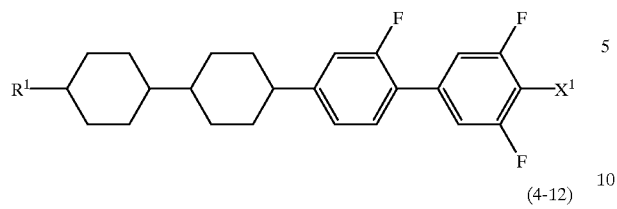 (4-11)
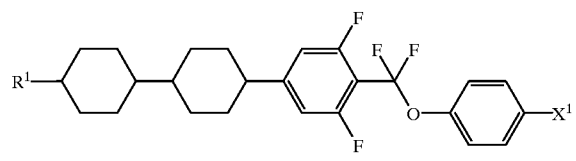 (4-20)
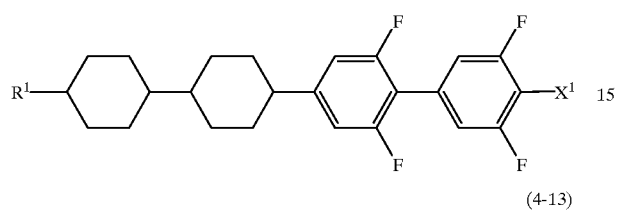 (4-12)
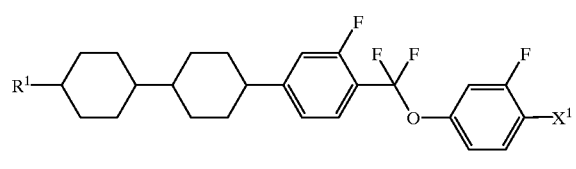 (4-21)
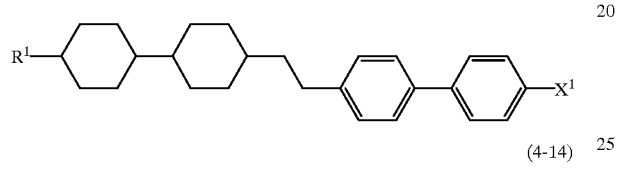 (4-13)
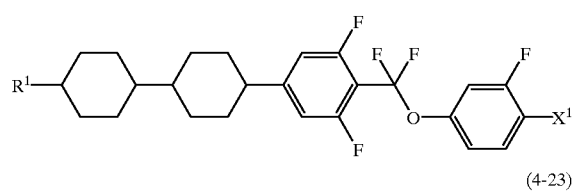 (4-22)
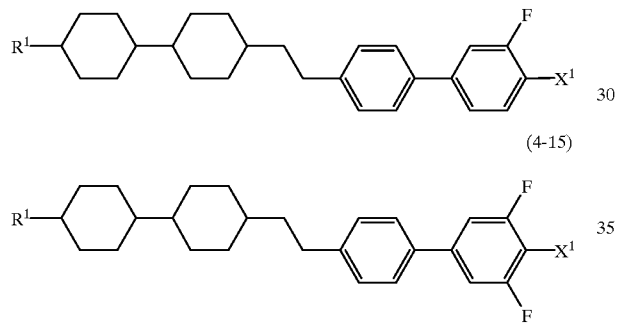 (4-14)
(4-15)
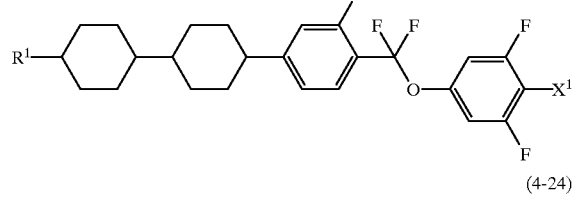 (4-23)
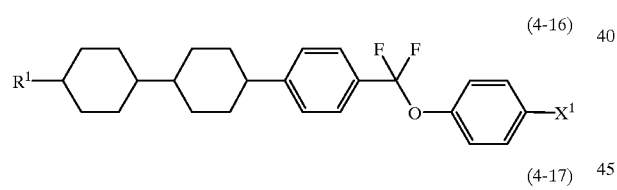 (4-16)
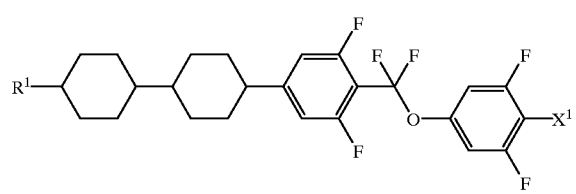 (4-24)
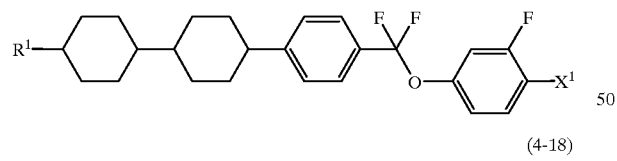 (4-17)
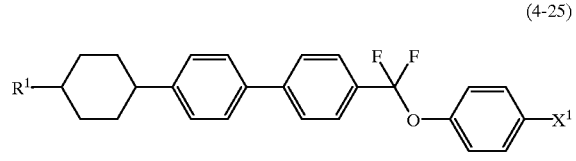 (4-25)
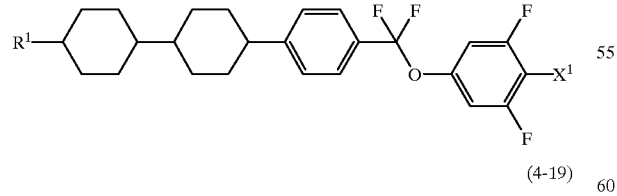 (4-18)
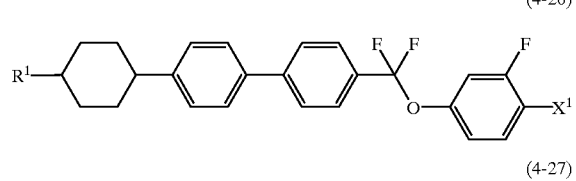 (4-26)
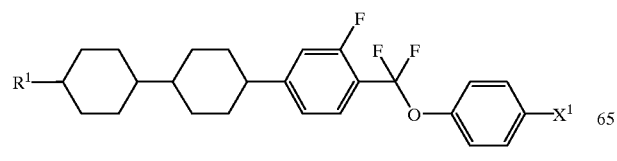 (4-19)
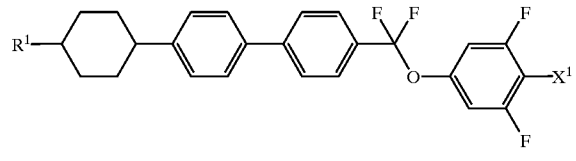 (4-27)

(in the formulas, $R^1$ and $X^1$ are the same as those described above).

The compounds represented by these Formulas (2) to (4) show a positive dielectric anisotorpy and is very excellent in heat stability and chemical stability, sot hat it is used primarily for a liquid crystal composition for TFT. When preparing a liquid crystal composition for TFT, a sue amount of the above compound falls suitably in a range of 0.1 to 99.9% by weight, preferably 10 to 97% by weight and more preferably 40 to 95% by weight based on the whole weight of the liquid crystal composition. The compounds represented by Formulas (10) to (12) may further be added for the purpose of controlling the viscosity.

Next, in the second B component described above, the compound of formulas (5-1) to (5-58) and (6-1) to (6-3) can be given as suitable examples of the compounds represented by Formulas (5) to (6).

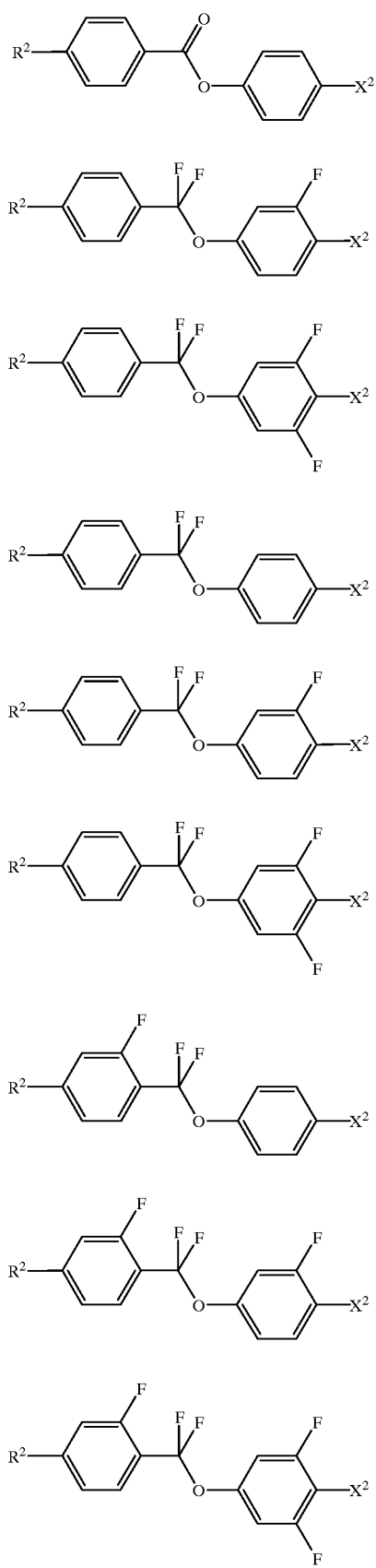
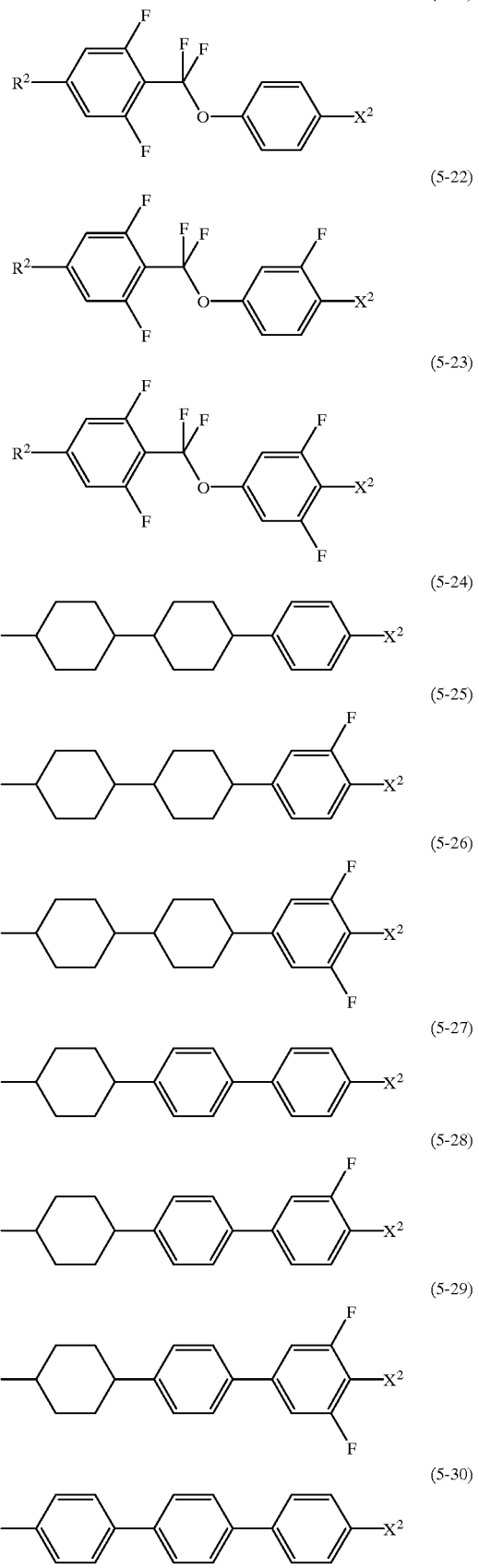

-continued
(5-31)
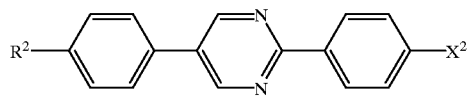
(5-32)
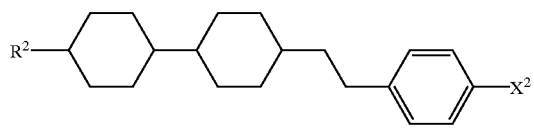
(5-33)
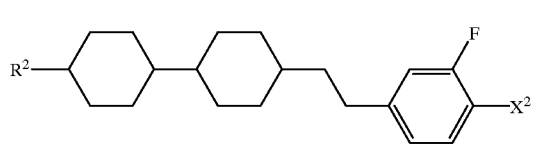
(5-34)
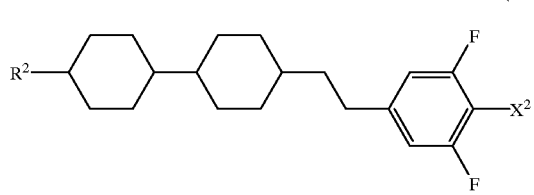
(5-35)
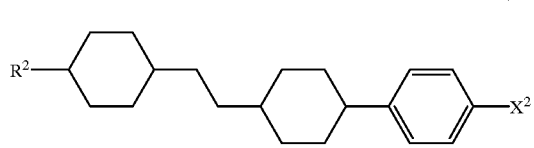
(5-36)
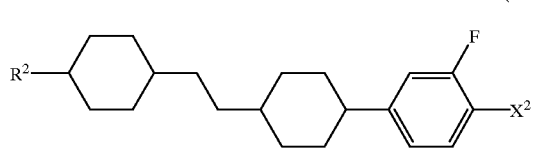
(5-37)
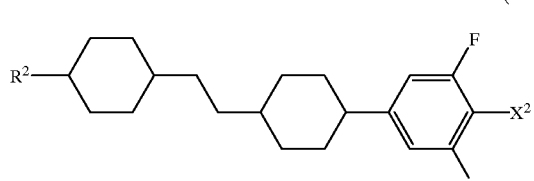
(5-38)
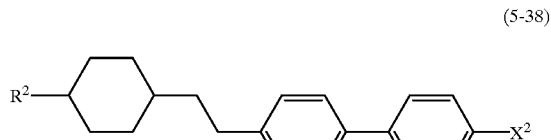
(5-39)
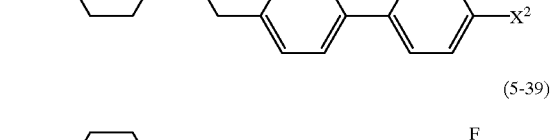
-continued
(5-40)
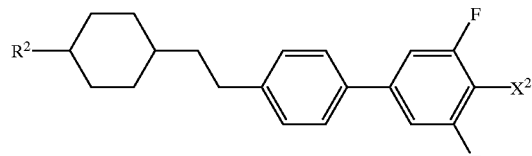
(5-41)
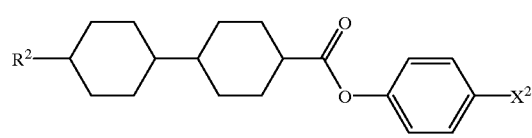
(5-42)
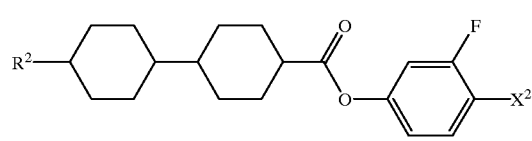
(5-43)
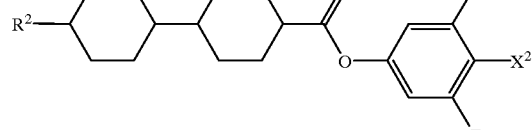
(5-44)
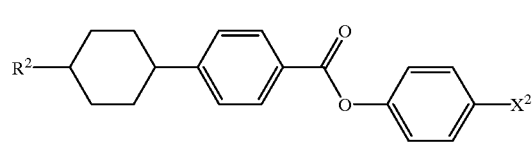
(5-45)
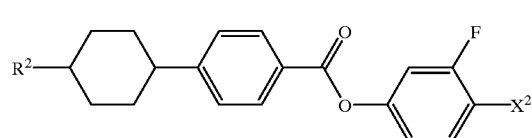
(5-46)
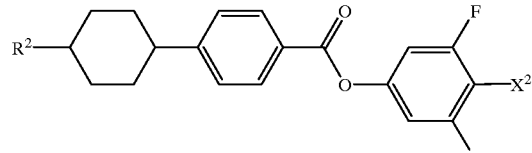
(5-47)
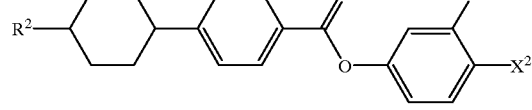

(5-48)
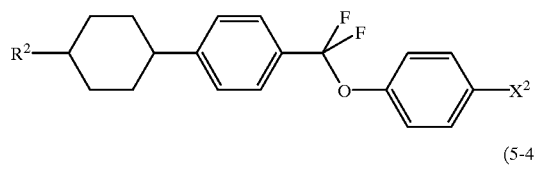

(5-49)
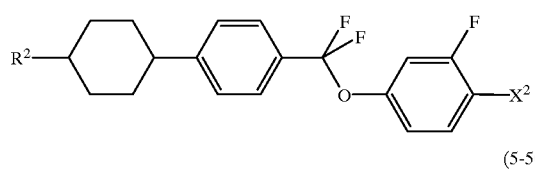

(5-50)
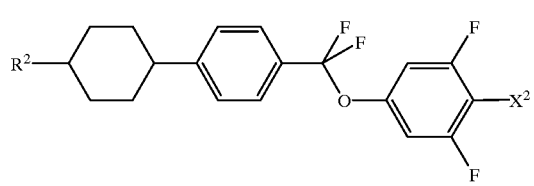

(5-51)
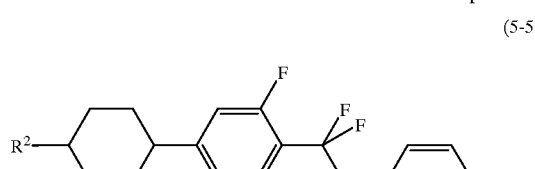

(5-52)
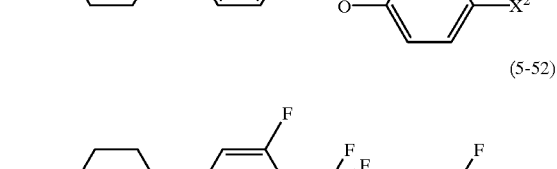

(5-53)
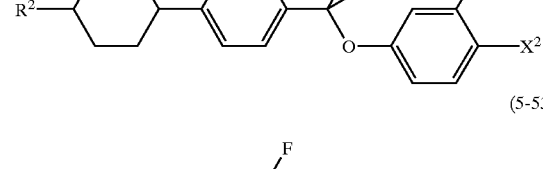

(5-54)
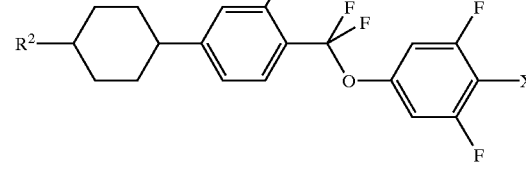

(5-55)
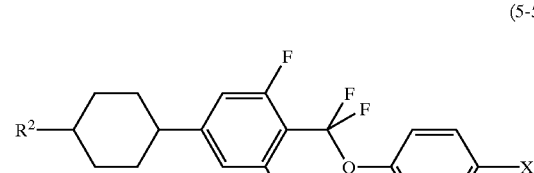

(5-56)
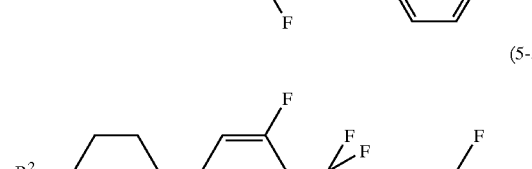

(5-57)
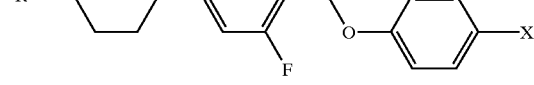

(5-58)
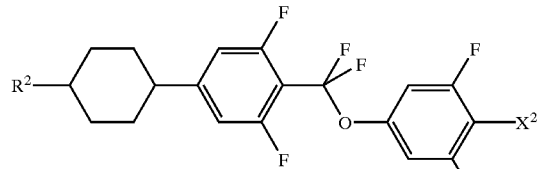

(6-1)
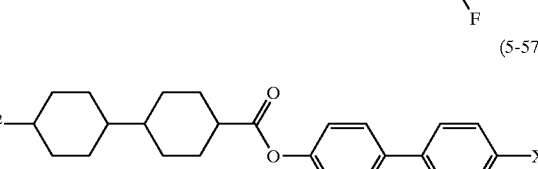

(6-2)
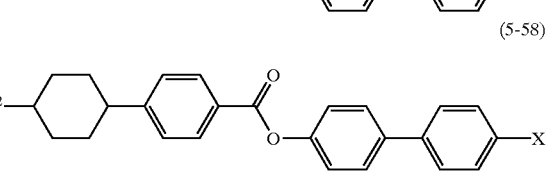

(6-3)
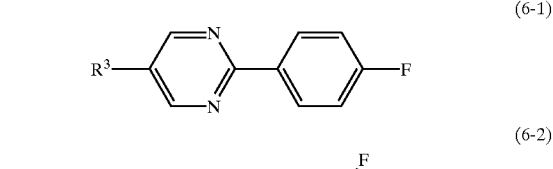

(in the formulas, $R^2$, $R^3$ and $X^2$ are the same as those described above).

The compounds represented by these Formulas (5) and (6) have a positive dielectric anisotropy, and a value thereof is very large, so that they are used mainly for the liquid crystal compositions for STN and TN. These compounds are used as a composition component particularly for the purpose of reducing a threshold voltage. Also, they are used for the purposes of controlling the viscosity and the optical anisotropy and expanding the liquid crystal phase temperature range and also for the purpose of improving the steepness. When preparing a liquid crystal composition for STN or TN, a use amount of the compounds represented by the Formulas (5) and (6) can be applied in a range of 0.1 to 99.9% by weight. A third component described later can be mixed for the purpose of controlling the threshold voltage, the liquid crystal phase temperature range, the optical anisotropy, the dielectric anisotropy and viscosity.

When a liquid crystal composition having a negative dielectric anisotropy which is used for a vertical aligning mode (VA mode) is prepared as the liquid crystal composition of the present invention, preferred is the composition mixed with at least one compound (hereafter referred to as a second C component) selected from the group consisting of the compound represented by Formulas (7) to (9). Compounds of formulas (7-1) to (7-3), (8-1) and (9-1) to (9-3)

can be given respectively as suitable examples of the compounds represented by Formulas (7) to (9) in the second C component.

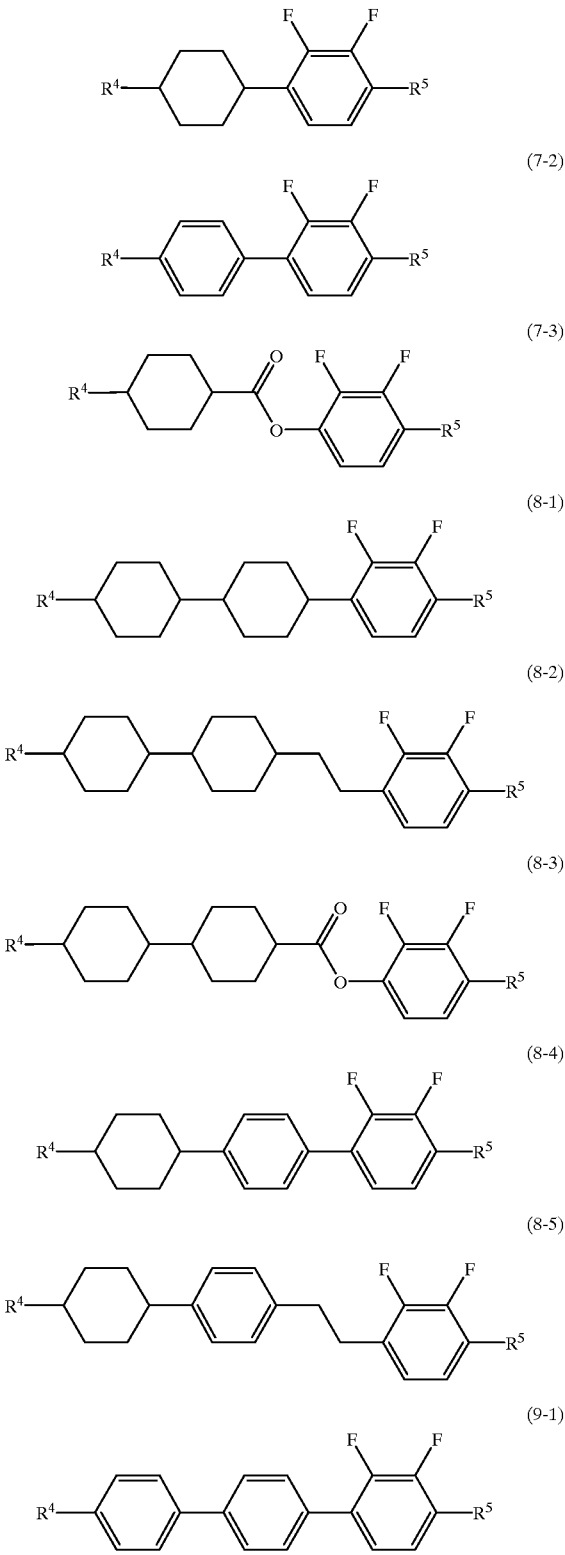

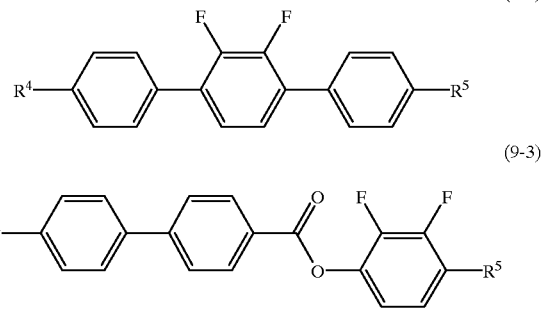

(in the formulas, $R^4$ and $R^5$ are the same as those described above).

The compounds represented by Formulas (7) to (9) are compounds having a negative dielectric anisotropy. The compound represented by Formula (7) is a dicyclic compound and therefore is used mainly for the purpose of controlling the threshold voltage, the viscosity or the dielectric anisotropy. The compound represented by Formula (8) is used not only for the purpose of expanding the nematic range by elevating the clearing point but also for the purpose of reducing the threshold voltage and increasing the optical anisotropy.

The compounds represented by Formulas (7) to (9) are used mainly for the liquid crystal composition for a VA mode having a negative dielectric anisotropy. If the use amount thereof is allowed to grow large, the composition is reduced in a threshold voltage but increased in viscosity, and therefore it; is preferably used in a smaller amount as long as a required value of the threshold voltage is satisfied. However, an absolute value of the dielectric anisotropy is 5 or less, and therefore the use amount of smaller than 40% by weight makes it impossible in a certain case to carry out voltage driving. A use amount of the compounds represented by Formulas (7) to (9) is preferably 40% by weight or more, more preferably 50 to 95% by weight when preparing the composition for a VA mode.

Further, the compounds represented by Formulas (7) to (9) are mixed in a certain case with the liquid crystal composition having a positive dielectric anisotropy for the purpose of controlling the elastic constant and a voltage transmission curve of the composition. In this case, a use amount of the compounds represented by Formulas (7) to (9) is preferably 30% by weight or less.

In the third component for the liquid crystal composition of the present invention, compounds of formulas (10-1) to (10-11), (11-1) to (11-12) and (12-1) to (12-6) can be given respectively as suitable examples of the compounds represented by Formulas (10) to (12).

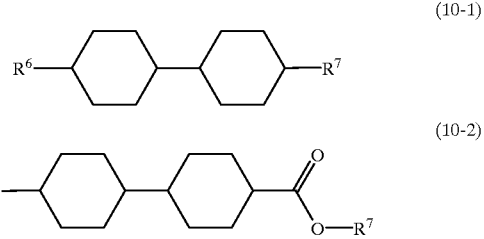

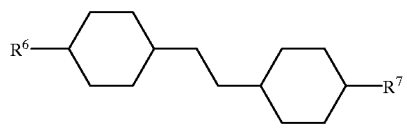
(10-3)
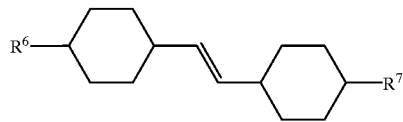
(10-4)
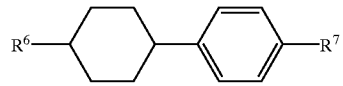
(10-5)
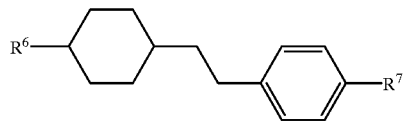
(10-6)
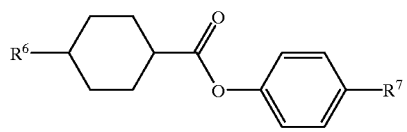
(10-7)
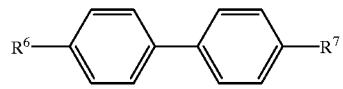
(10-8)
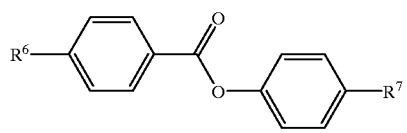
(10-9)
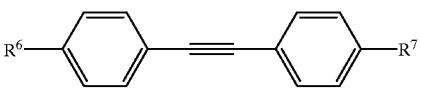
(10-10)
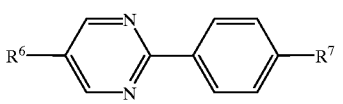
(10-11)
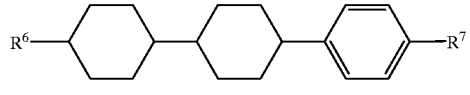
(11-1)
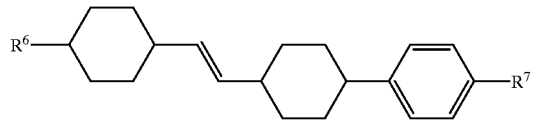
(11-2)
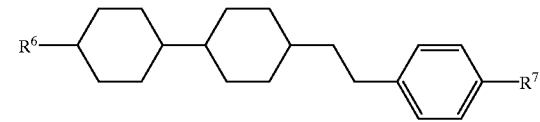
(11-3)
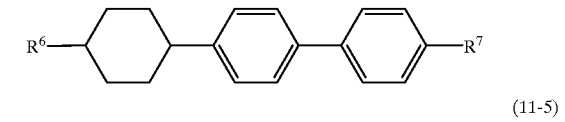
(11-4)
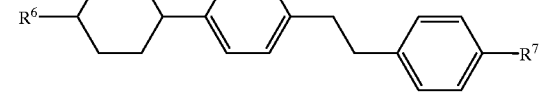
(11-5)
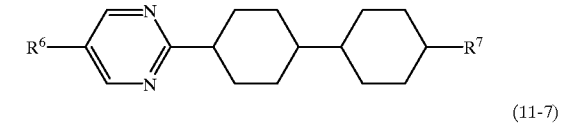
(11-6)
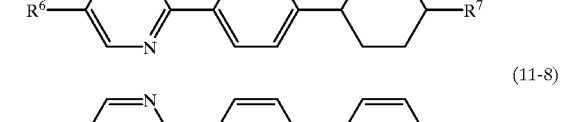
(11-7)
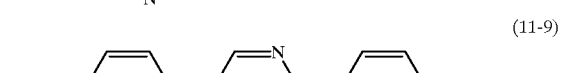
(11-8)
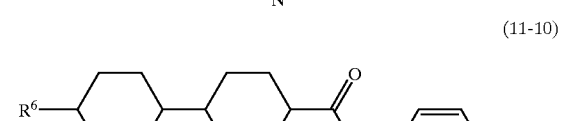
(11-9)
(11-10)
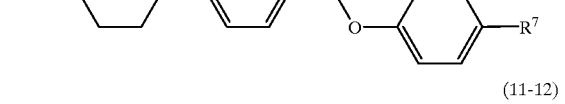
(11-11)
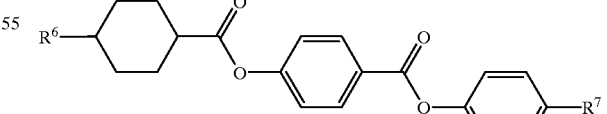
(11-12)
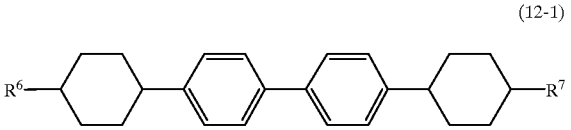
(12-1)

-continued (12-2)
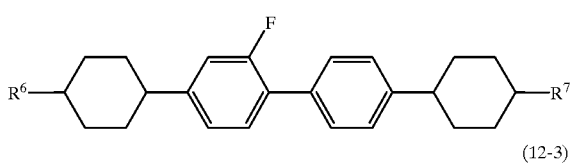

(12-3)
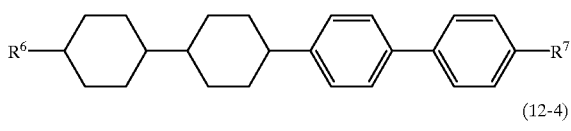

(12-4)
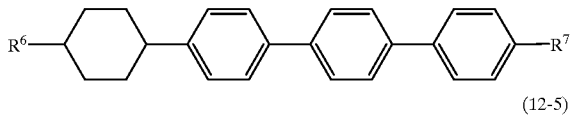

(12-5)
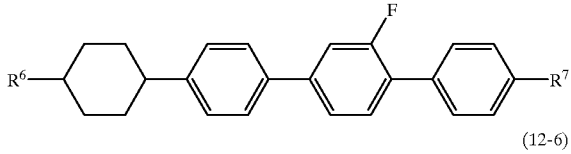

(12-6)
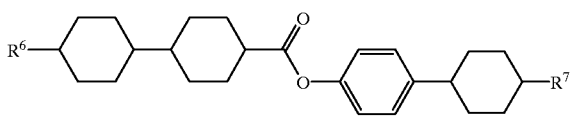

(in the formulas, $R^6$ and $R^7$ are the same as those described above).

The compounds represented by Formulas (10) to (12) are compounds which have a small absolute value of dielectric anisotropy and which are close to neutrality. The compound represented by Formula (10) is used mainly for the purpose of controlling the viscosity or the optical anisotropy. Further, the compounds represented by Formulas (11) and (12) are used for the purpose of broadening the nematic range by elevating the clearing point or the purpose of controlling the optical anisotropy.

If a use amount of the compounds represented by the Formulas (10) to (12) is increased, the liquid crystal composition is elevated in a threshold voltage and reduced in viscosity, and therefore it is used preferably in a large amount as long as a required value of a threshold voltage of the liquid crystal composition is satisfied. When preparing the liquid crystal composition for TFT, a use amount of the compounds represented by Formulas (10) to (12) is preferably 40% by weight or less, more preferably 35% by weight or less. Further, when preparing the liquid crystal composition for STN or TN, a use amount of the compounds represented by Formulas (10) to (12) is preferably 70% by weight or less, more preferably 60% by weight or less.

The liquid crystal composition provided according to the present invention preferably contains at least one of the liquid crystalline compounds represented by Formula (1) in a proportion of 0.1 to 99% by weight in order to allow excellent characteristics to be revealed.

The above liquid crystal composition is usually prepared by a publicly known method, for example, a method in which various components are dissolved at high temperatures. Further, suitable additives are added if necessary, whereby the liquid crystal composition is improved according to intended uses and is optimized. Such additives are well known by a person averagely skilled in the art and described in detail in literatures. Usually, added is a chiral dopant having an effect of inducing a spiral structure of liquid crystal to control a required distortion angle and prevent inverse distortion. The following optically active compounds can be given as examples of the chiral dopant used in this case.

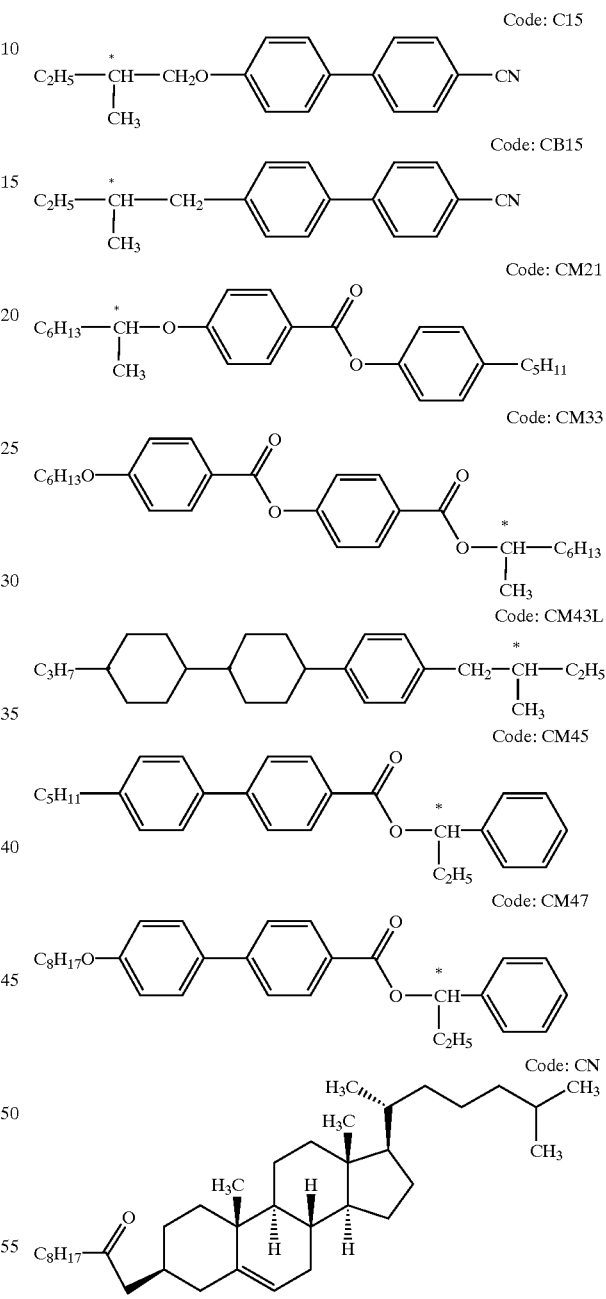

Usually, in the liquid crystal composition of the present invention, these optically active compounds are added to control a pitch in distortion. The pitch in distortion is preferably controlled in a range of 40 to 200 μm in the case of the liquid crystal compositions for TFT and TN. In the case of the liquid crystal composition for STN, it is preferably controlled in a range of 6 to 20 μm. Further, in the case of the liquid crystal composition for a bistable TN mode, it is preferably controlled in a range of 1.5 to 4 μm. Two or more kinds of the optically active compound may be added for the purpose of controlling a temperature dependency of the pitch.

The liquid crystal composition of the present invention can also be used as a liquid crystal composition for a G–H mode by adding a dichromatic dye such as a merocyanine base, a styryl base, an azo base, an azomethine base, an azoxy base, a quinophthalone base, an anthraquinone base and tetrazine base. The liquid crystal composition according to the present invention can also be used as a liquid crystal composition for a birefrigence-controlling (ECB) mode and a DS mode as well as NCAP prepared by micro-capsulizing nematic liquid crystal and polymer dispersion mode liquid crystal display (PDLCD) prepared by forming a three-dimensional network polymer in the liquid crystal, for example, a polymer network liquid crystal display (PNLCD).

The compounds (1) and (13) of the present invention can easily be produced by using conventional organic synthetic chemical method. They can readily be synthesized by suitably selecting and combing known reactions described in publications and magazines such as, for example, Organic Synthesis (John Wiley & Sons), Organic Reactions (John Wiley & Sons), Comprehensive Organic Synthesis (Pergamon Press) and New Experimental Chemistry Course (Maruzen).

To be specific, a difluorovinyl group can be introduced through a route shown below. That is, an aldehyde derivative (21) is reacted with sodium chlorodifluoroacetate and triphenyl phosphine in N,N-dimethylformamide (hereinafter abbreviated as DMF) and diethylene glycol dimethyl ether, whereby the compound (1) can be obtained:

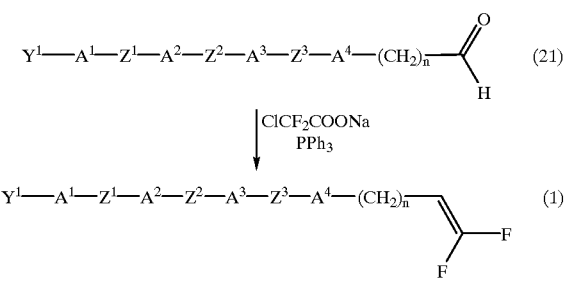

(in the formulas, $A^1$, $A^2$, $A^3$, $A^4$, $Z^1$, $Z^2$, $Z^3$ and n are the same as those described above).

Further, the synthetic intermediate (13) can be synthesized as well through a route which is similar to that shown above. That is, an aldehyde derivative (31) is reacted with sodium chlorodifluoroacetate and triphenyl phosphine in DMF and diethylene glycol dimethyl ether, whereby the compound (13) can be obtained:

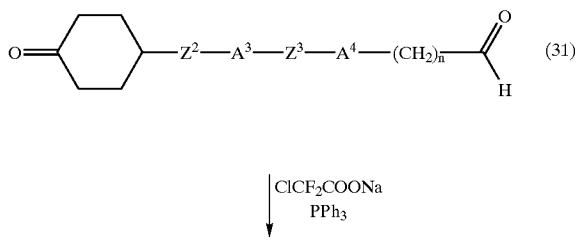

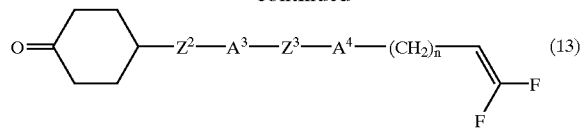

(in the formulas, $A^3$, $A^4$, $Z^2$ and $Z^3$ are the same as those described above).

The synthetic intermediate (13) is reacted with triphenylphophonium halide (32) in the same manner as described above in an ether base solvent such as THF and diethyl ether in the presence of a base such as sodium methylate, potassium t-butoxide (t-BuOK) and butyl lithium and then dehydrated by virtue of an action of a mineral acid such as hydrochloric acid and sulfuric acid or an organic acid such as formic acid and p-toluenesulfonic acid, whereby an aldehyde compound (34) is obtained. The compound (34) is reacted with a diol compound (35) by virtue of an action of a mineral acid such as hydrochloric acid and sulfuric acid or an organic acid such as formic acid and p-toluenesulfonic acid, whereby a dioxane ring can be introduced as shown in a compound (36):

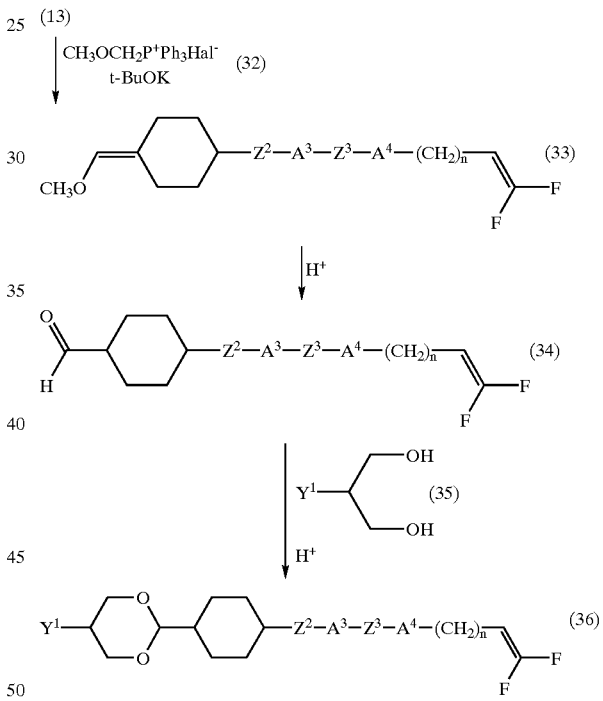

(in the formulas, $A^3$, $A^4$, $Z^2$ and $Z^3$ are the same as those described above, and Hal is Cl, Br or I).

The liquid crystalline compound of the present invention thus obtained is physically and chemically very stable under conditions on which a display is used. Further, it shows such characteristics that it has a wide liquid crystal phase temperature range, a good solubility in a liquid crystal dielectric anisotropy and large elastic constant ratio $K_{33}/K_{11}$, and it is very excellent as a structural component for a liquid crystal composition suited to various display modes. Further, the synthetic intermediate is very useful in synthesizing the liquid crystalline compound of the present invention.

EXAMPLES

The present invention shall be explained below in more details with reference to examples, but the present invention shall by no means be restricted by these examples The structures of the compounds were confirmed by means of a nuclear magnetic resonance spectrum and a mass spectrum (hereinafter abbreviated a MS). In the examples, M+ in MS represents a molecular ion peak. C shows a crystal phase; $S_B$ shows a smectic B phase; N shows a nematic phase; Iso shows an isotropic liquid phase; and a unit of a phase transition temperature is ° C. in all examples.

Example 1

Production of 4-(trans-4-(2,2-difluoroethenyl)-cyclohexyl)cyclohexanone compound (No. 2) in which in Formula (13), $A^3$ is trans-1,4-cyclohexylene; $A^4$, $Z^2$ and $Z^3$ are single bonds; and n is 0)

First stage:

Added to 500 ml of DMF were 4-(4-formylcyclohexyl) cyclohexanone (100 mmol) and triphenyl phosphine (200 ml), and the temperature was elevated while stirring under nitrogen flow. When the temperature reached 100° to 110° C., a solution prepared by dissolving sodium chlorodifluoroacetate (300 mmol) in 400 ml of DMF was dropwise added while maintaining the same temperature. After finishing dropwise adding, the solution was stirred for 30 minutes and left cooling down to a room temperature. 1 L of water and 1 L of heptane were added to the reaction mixture, and the mixture was sufficiently stirred and then filtered through celite. Further, the aqueous layer was extracted with 500 ml of heptane, and the organic layer was washed three times with 700 ml of water and dried on anhydrous magnesium sulfate. The solvent was distilled off under reduced pressure, and the residue was subjected to silica gel chromatography (eluent: toluene) and recrystallized from heptane, whereby obtained was 4-(trans-4-(2,2-difluoroethenyl)-cyclohexyl)cyclohexanone (12 mmol) which was the captioned product.

Phase transition temperature: Cr 42.5 Iso

MS: m/e=242 (M+)

The following compounds can be produced according to the method in Example 1.

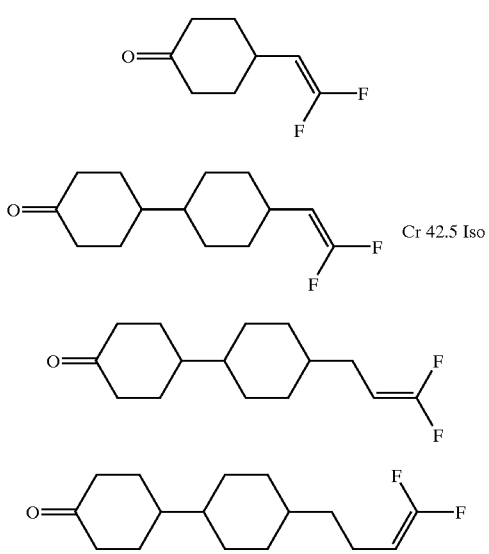

Cr 42.5 Iso

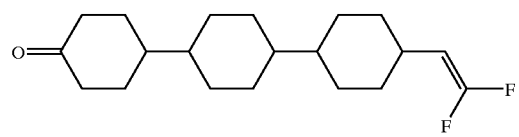
No. 5

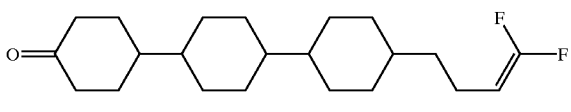
No. 6

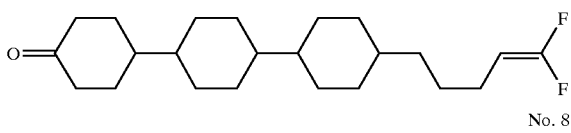
No. 7

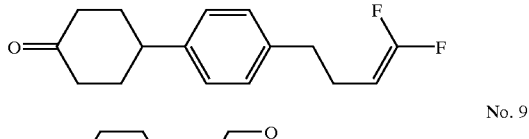
No. 8

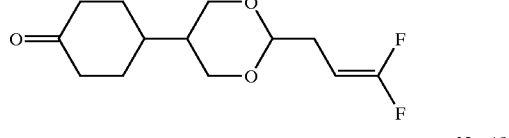
No. 9

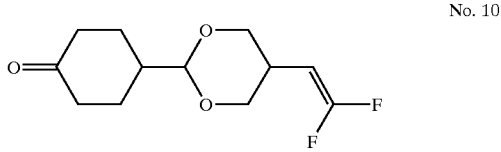
No. 10

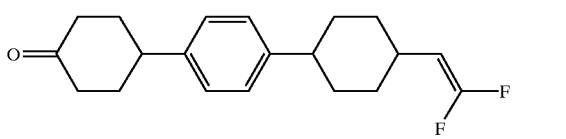
No. 11

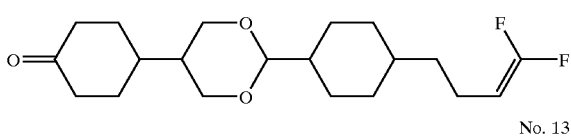
No. 12

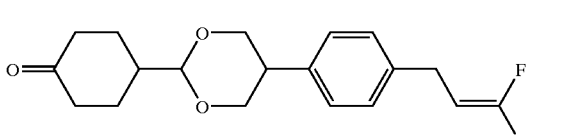
No. 13

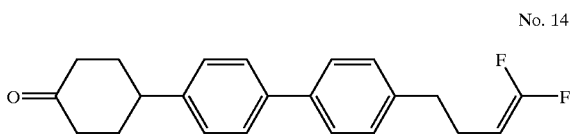
No. 14

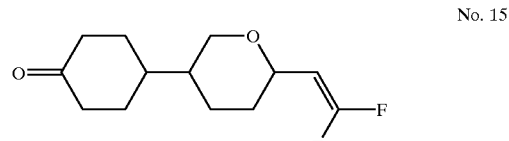
No. 15

-continued
No. 16
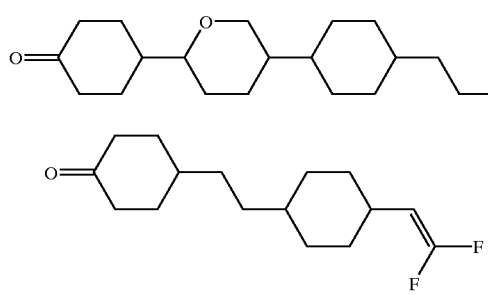
No. 17
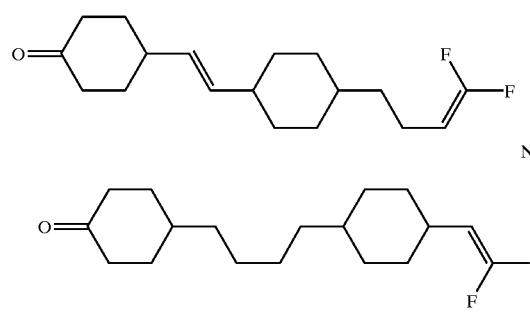
No. 18
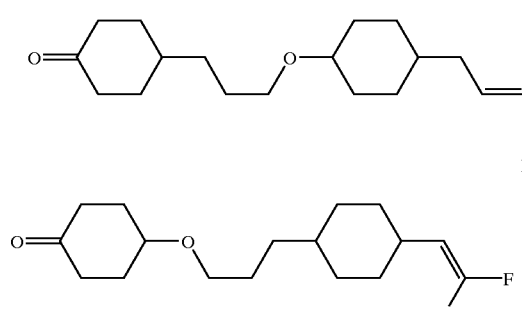
No. 19
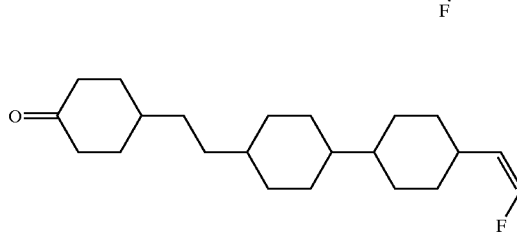
No. 20
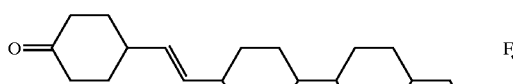
No. 21
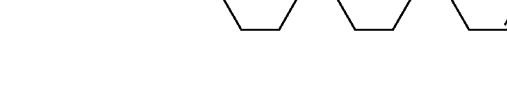
No. 22
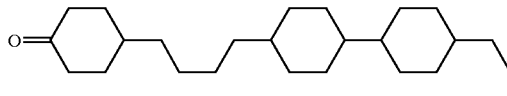
No. 23
No. 24
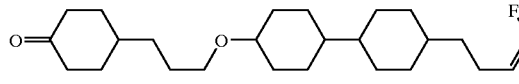
No. 25
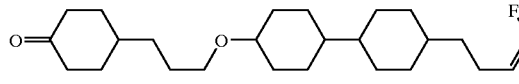
-continued
No. 26
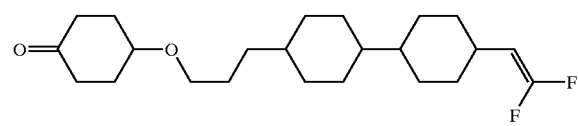
No. 27
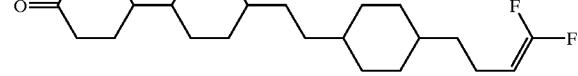
No. 28
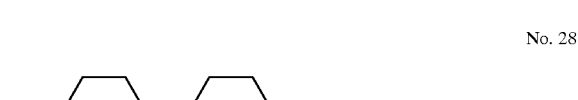
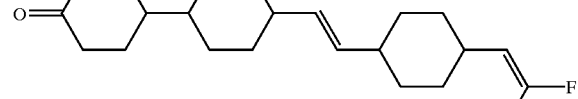
No. 29
No. 30
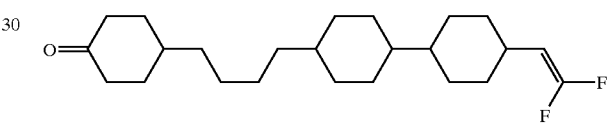
No. 31
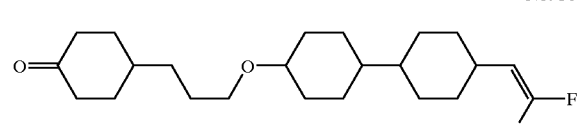
No. 32
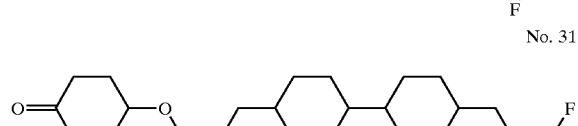
No. 33
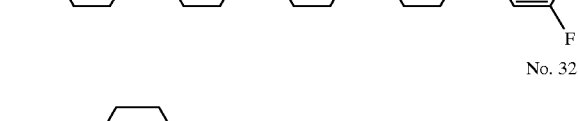
No. 34
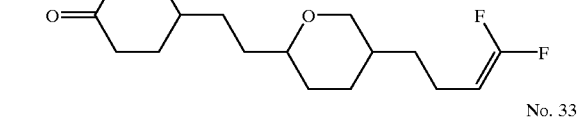

No. 35
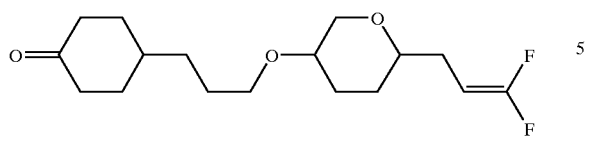

No. 36
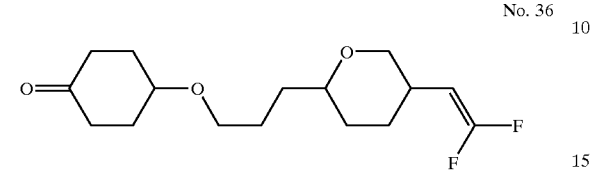

No. 37
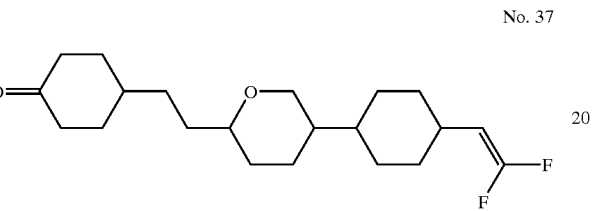

No. 38
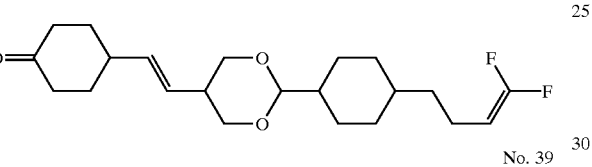

No. 39
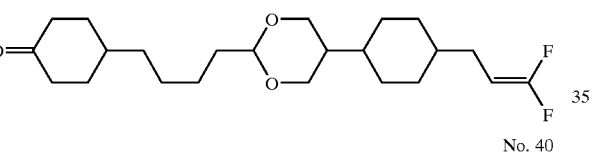

No. 40
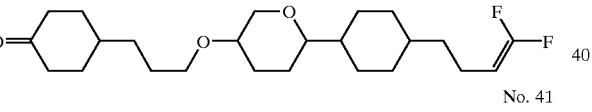

No. 41
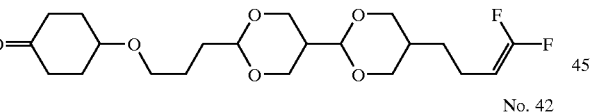

No. 42
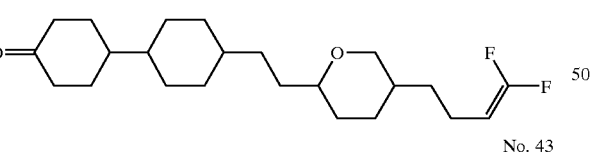

No. 43
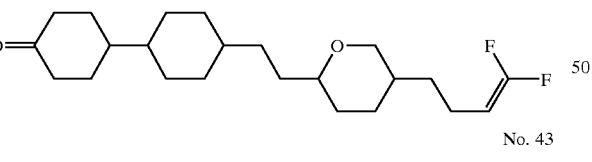

No. 44
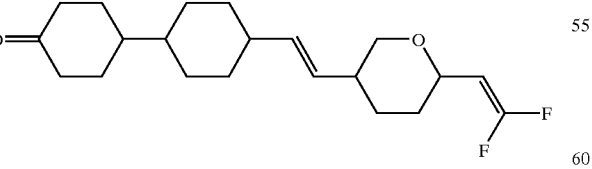

No. 45
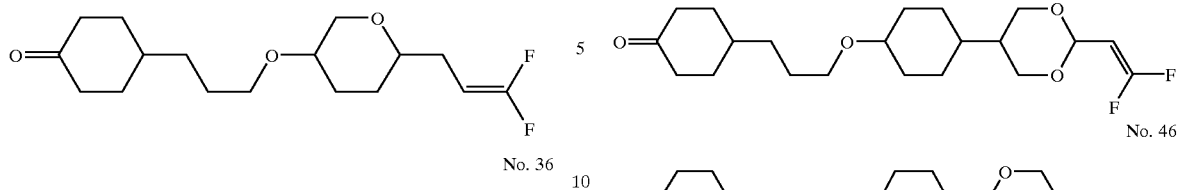

No. 46
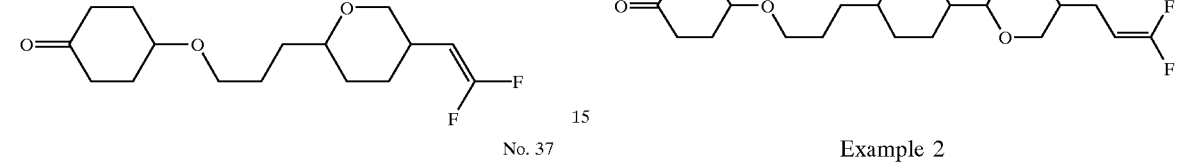

Example 2

Production of trans-1-(2,2-difluoroethenyl)-4-(trans-4-trans-5-propyl-1,3-dioxane-2-yl)cyclohexyl) cyclohexane (compound (No. 95) in which in Formula (1), $Y^1$ is propyl; $A^1$ is trans-1,3-dioxane-2,5-diyl; $A^2$ and $A^3$ are trans-1,4-cyclohexylene; $A^4$, $Z^1$, $A^2$ and $Z^3$ are single bonds; and n is 0)

First stage:

A mixture of methoxymethyltriphenylphosphonium chloride (120 mmol) and 60 ml of THF was cooled down to −30° C. by means of a coolant under nitrogen flow. t-BuOK (120 mol) was added to this mixture and stirred for one hour. A THF 150 ml solution of 4-(trans-4-(2,2-difluoroethenyl)-cyclohexyl)cyclohexanone (100 ml) was dropwise added to this mixture while maintaining −30° C. or lower. After finishing dropwise adding, the reaction temperature was slowly elevated up to room temperature, and the mixture was stirred for further 2 hours. The reaction mixture was filtered through celite, and the solvent was distilled off under reduced pressure. The residue was subjected to silica gel chromatography (spreading solvent: toluene), and the solvent was distilled off under reduced pressure, whereby obtained was crude trans-1-(2,2-difluoroethenyl)-4-(4-methoxymethylene-cyclohexylene)cyclohexane (97 mmol).

Second stage:

Crude trans-1-(2,2-difluoroethenyl)-4-(4-methoxymethylenecyclohexylene)cyclohexanone (97 mmol) obtained by the reaction in the first stage was dissolved in 100 ml of toluene, and 87%-formic acid (970 mmol) was added thereto, followed by heating and refluxing for 4 hours. The reaction mixture was washed twice with 100 ml of a saturated sodium hydrogencarbonate aqueous solution and three times with 100 ml of water and dried on anhydrous magnesium sulfate. The solvent was distilled off under reduced pressure to obtain crude trans-1-(2,2-difluoroethenyl)-4-(4-formylcyclohexyl)cyclohexane (88 mmol).

Third stage:

Crude trans-1-(2,2-difluoroethenyl)-4(4-formylcyclohexyl)cyclohexane (88 mmol) and 2-propyl-1,3-propanediol (132 mmol) were dissolved in 100 ml of foluene, and p-toluenesulfonic acid dihydrate (8.8 mmol) was added thereto, followed by heating and refluxing for 2 hours while discharging resulting water to the outside of the reaction system. The reaction mixture was washed twice with 100 ml of a saturated sodium hydrogencarbonate aqueous solution and three times with 100 ml of water and dried on anhydrous magnesium sulfate. The solvent was distilled off under reduced pressure, and the residue was subjected to silica gel chromatography (eluent: toluene) and recrystallized from heptane, whereby obtained was trans-1-

(2,2-difluoroethenyl)-4-(trans-5-propyl-1,3-dioxane-2-yl)cyclohexyl)cyclohexane (13 mmol) which was the captioned product.
Phase transition temperature: Cr 39.6 $S_B$ 196.5 N 202.3 Iso
Ms: m/e=356 (M+)
The following compounds can be produced according to the method in Example 2.
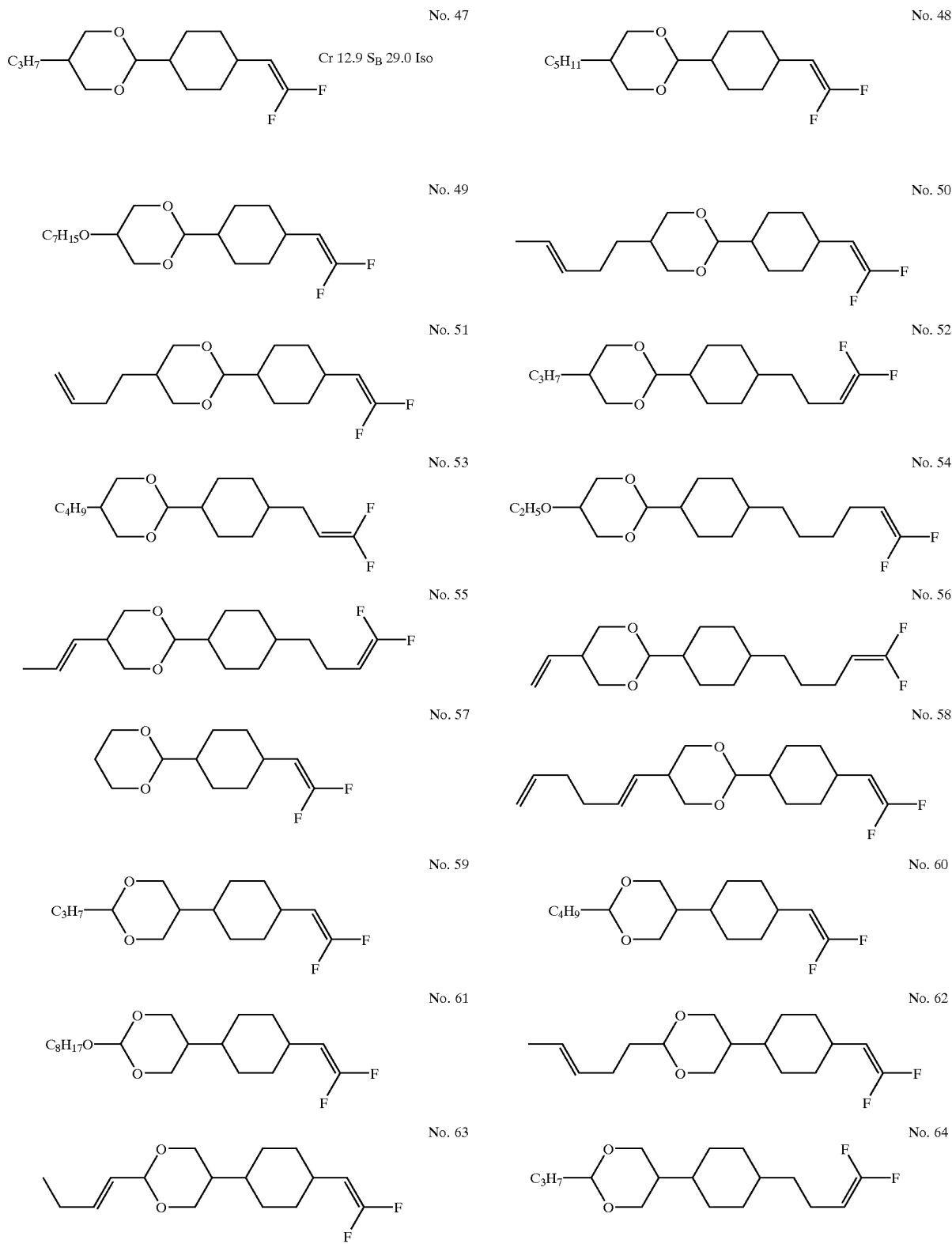

-continued
No. 65
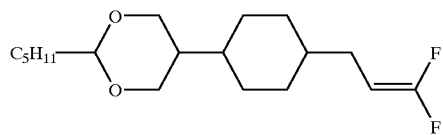
No. 66
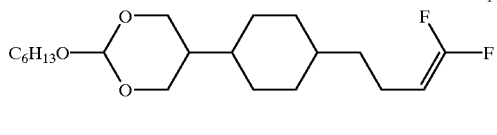
No. 67
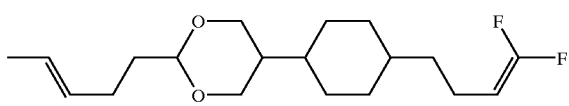
No. 68
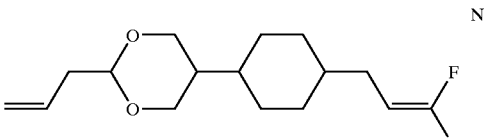
No. 69
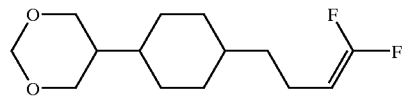
No. 70
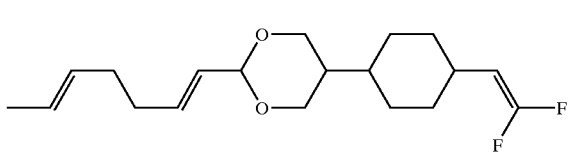
No. 71
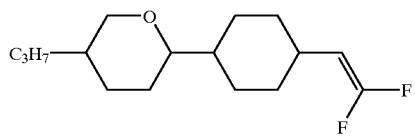
No. 72
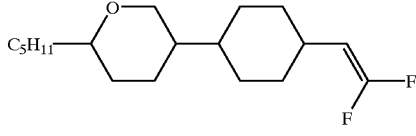
No. 73
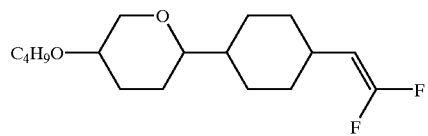
No. 74
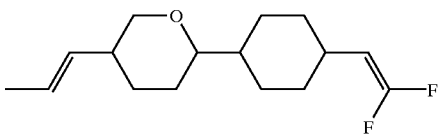
No. 75
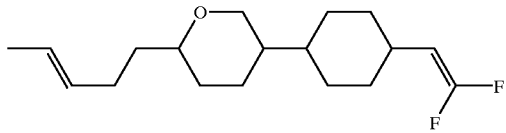
No. 76
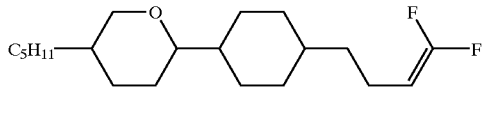
No. 77
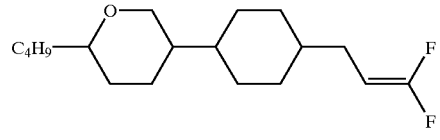
No. 78
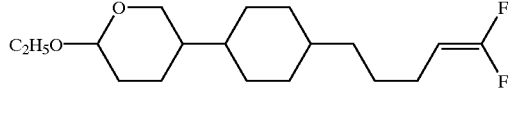
No. 79
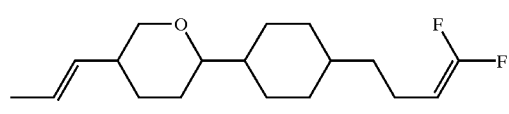
No. 80
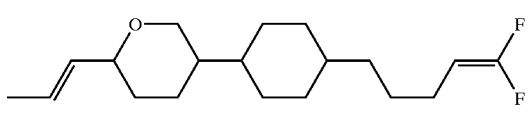
No. 81
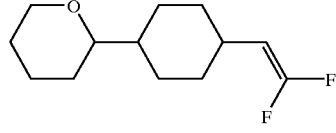
No. 82
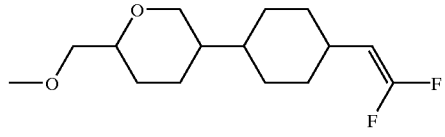
No. 83
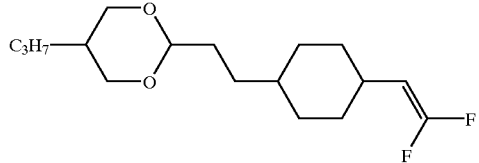
No. 84
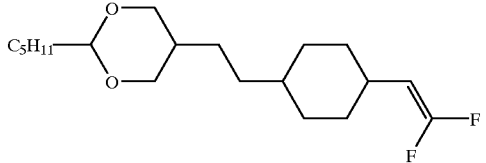

-continued
No. 85
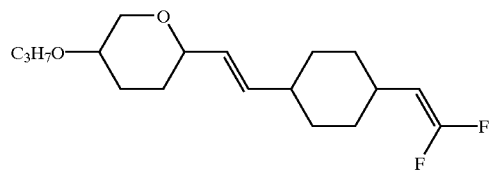
No. 86
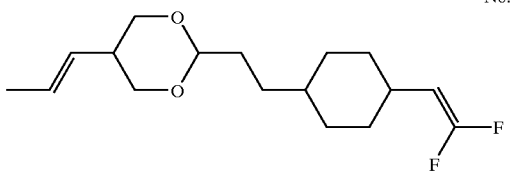
No. 87
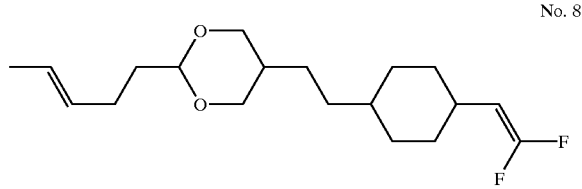
No. 88
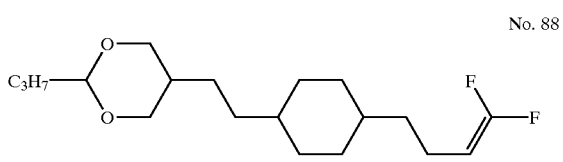
No. 89
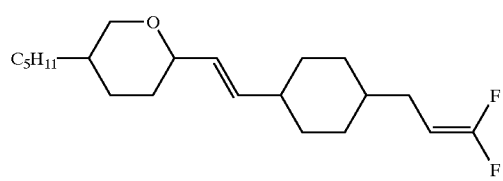
No. 90
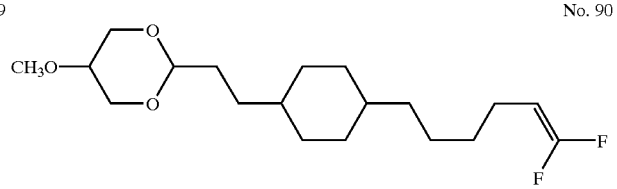
No. 91
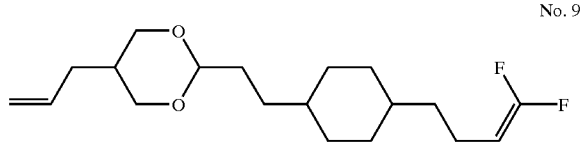
No. 92
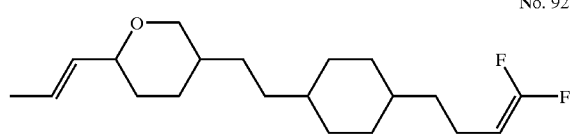
No. 93
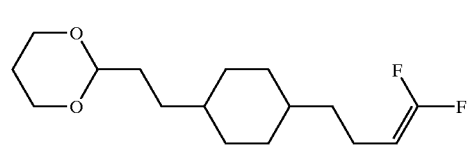
No. 94
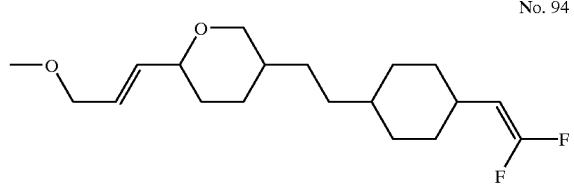
No. 95
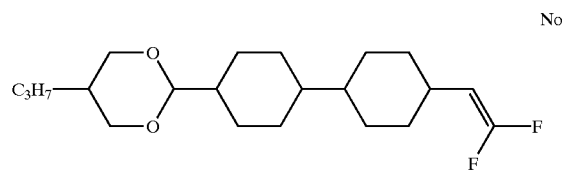
Cr 39.6 S$_B$ 196.5 N 202.3 Iso
No. 96
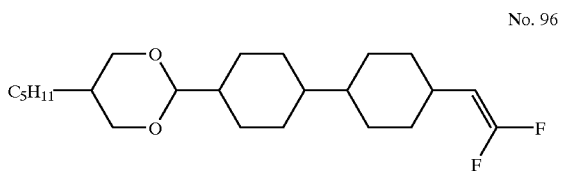
No. 97
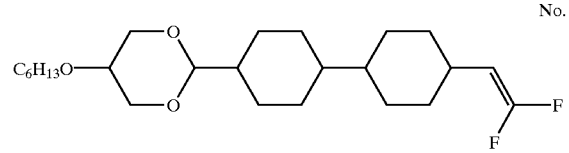
No. 98
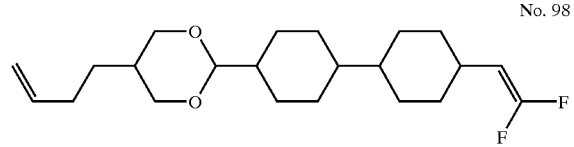
No. 99
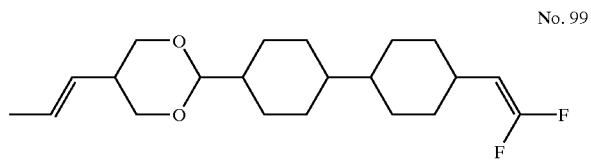
No. 100
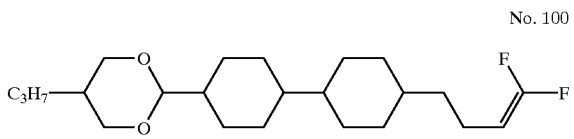
No. 101
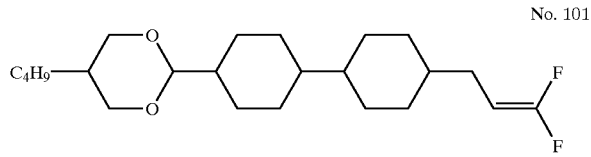
No. 102
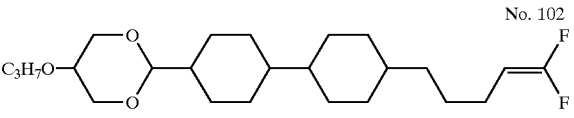

-continued
No. 103
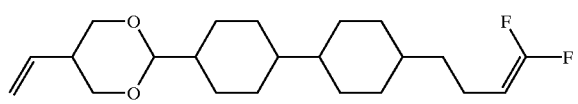
No. 104
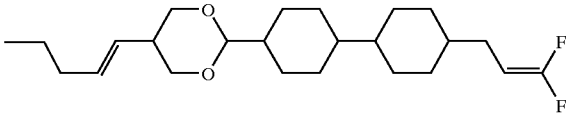
No. 105
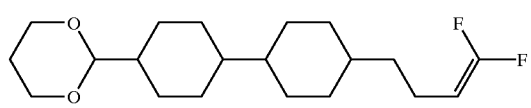
No. 106
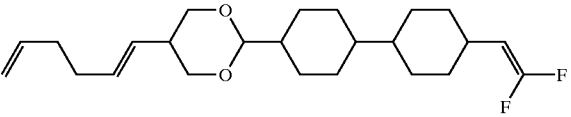
No. 107
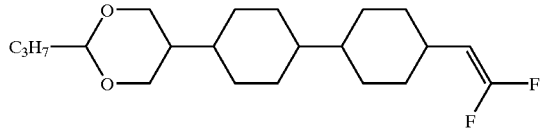
No. 108
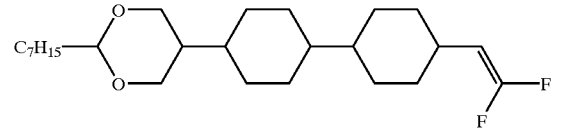
No. 109
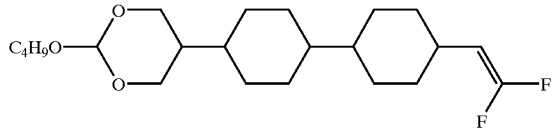
No. 110
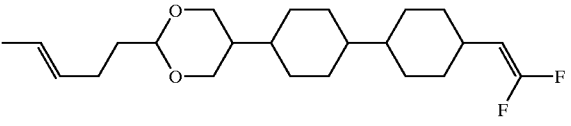
No. 111
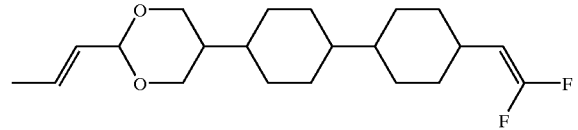
No. 112
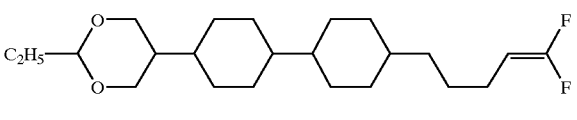
No. 113
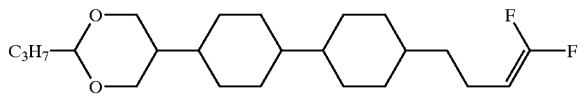
No. 114
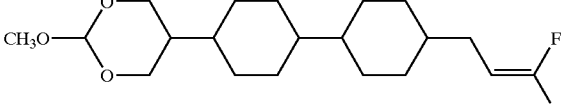
No. 115
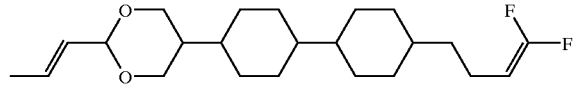
No. 116
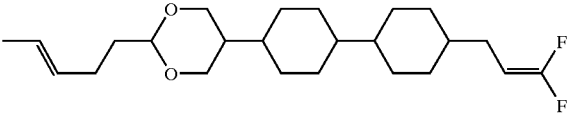
No. 117
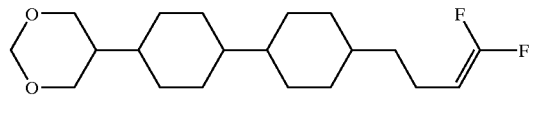
No. 118
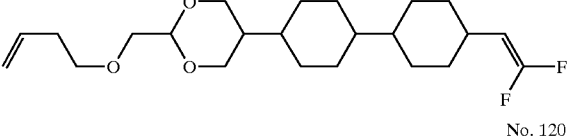
No. 119
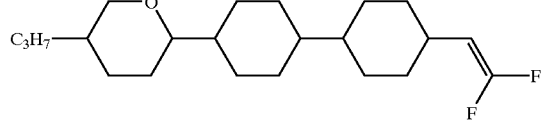
No. 120
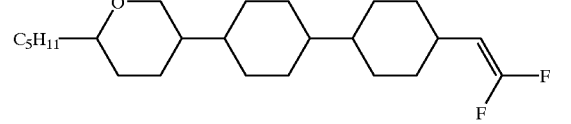
No. 121
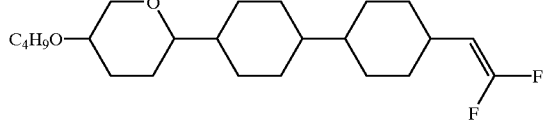
No. 122
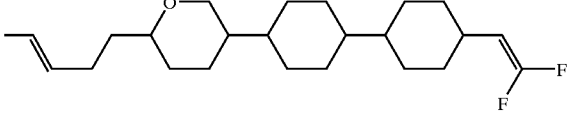
No. 123
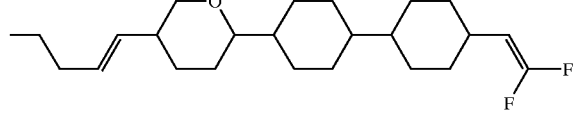
No. 124
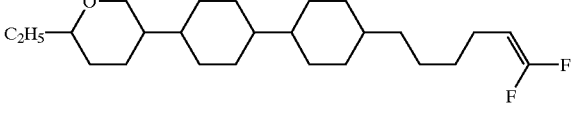

Cr 47.9 S$_B$ 171.4 Iso

-continued

No. 145 / No. 146 / No. 147 / No. 148 / No. 149 / No. 150 / No. 151 / No. 152 / No. 153

Cr 47.7 S_B 124.3 Iso

No. 154 / No. 155 / No. 156 / No. 157 / No. 158 / No. 159 / No. 160 / No. 161 / No. 162 / No. 163 / No. 164

-continued
No. 165
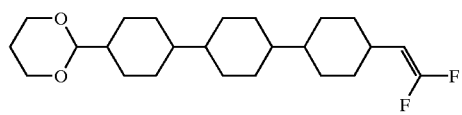
No. 166
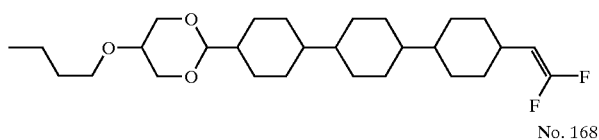
No. 167
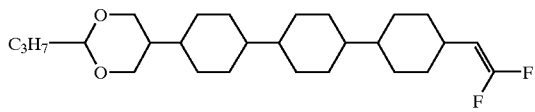
No. 168
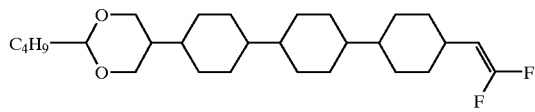
No. 169
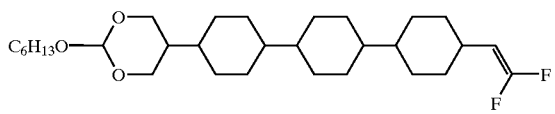
No. 170
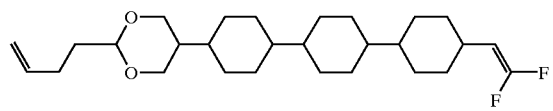
No. 171
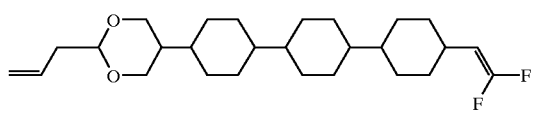
No. 172
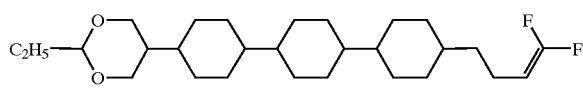
No. 173
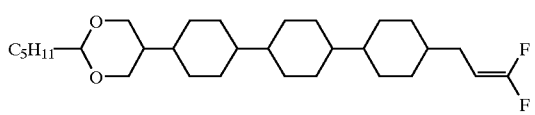
No. 174
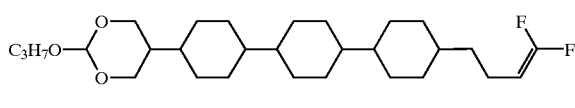
No. 175
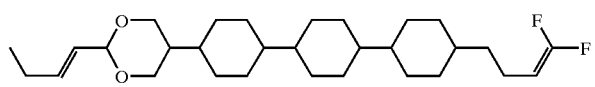
No. 176
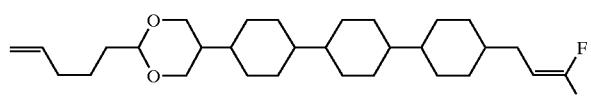
No. 177
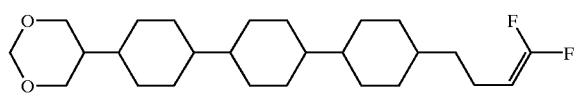
No. 178
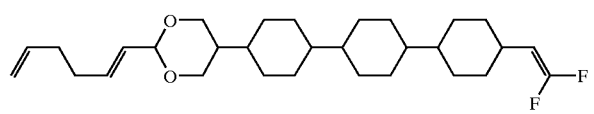
No. 179
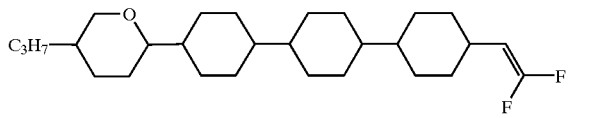
No. 180
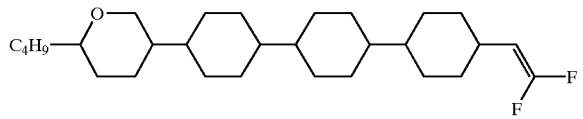
No. 181
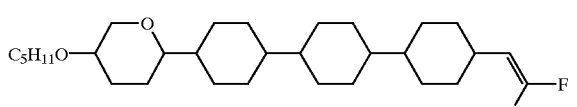
No. 182
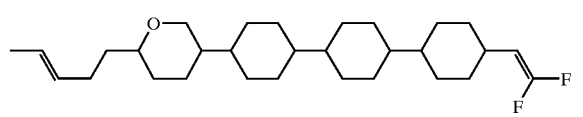
No. 183
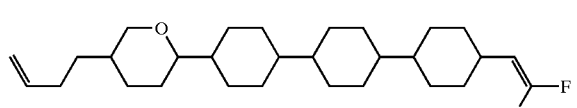
No. 184
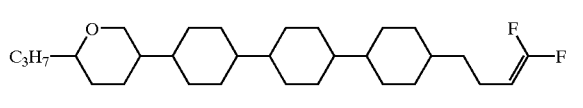

-continued
No. 185
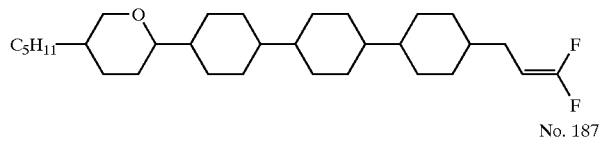
No. 186
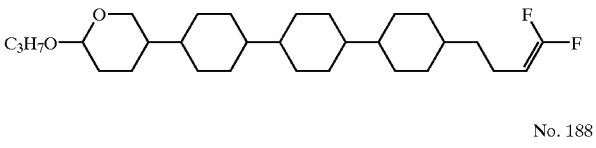
No. 187
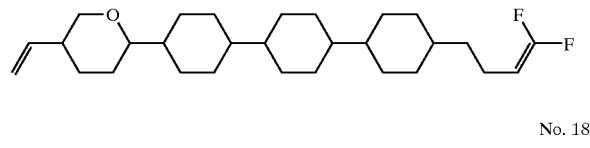
No. 188
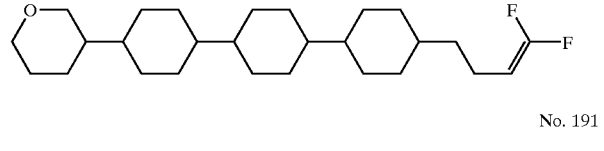
No. 189
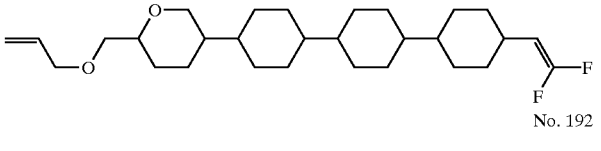
No. 190
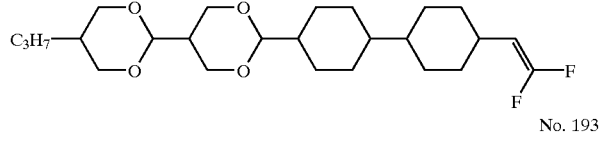
No. 191
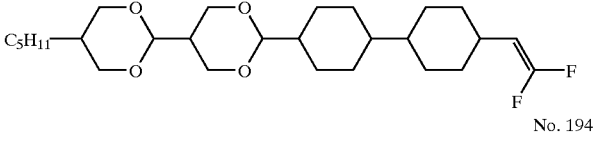
No. 192
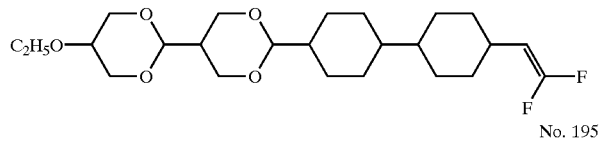
No. 193
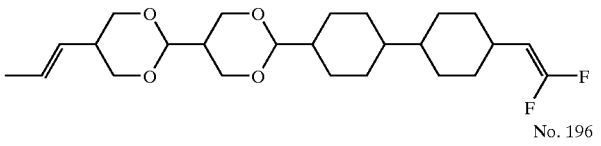
No. 194
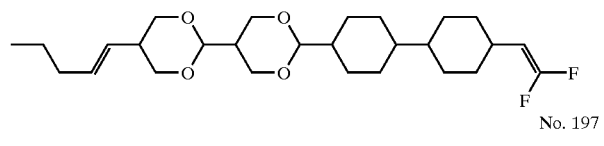
No. 195
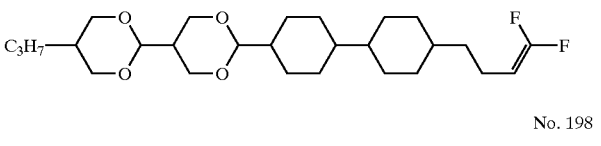
No. 196
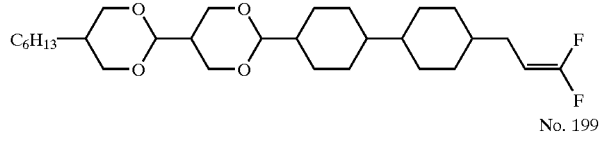
No. 197
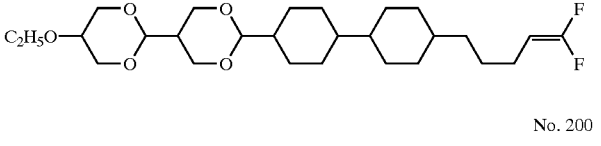
No. 198
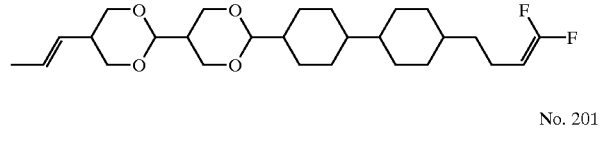
No. 199
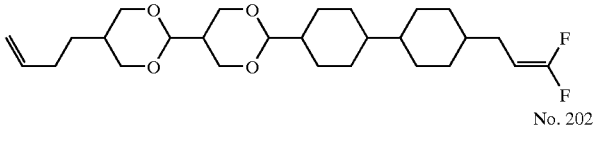
No. 200
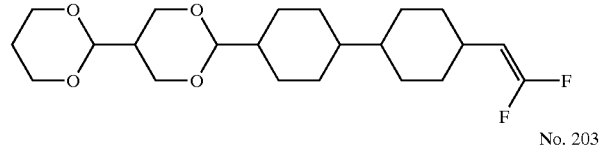
No. 201
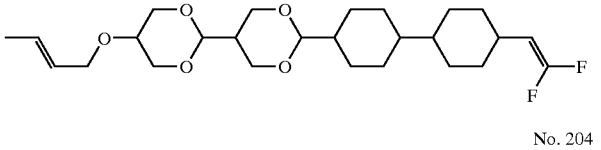
No. 202
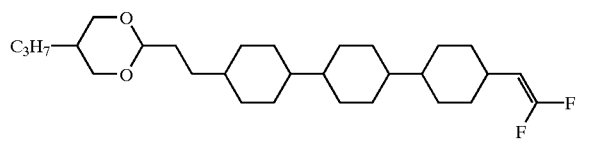
No. 203
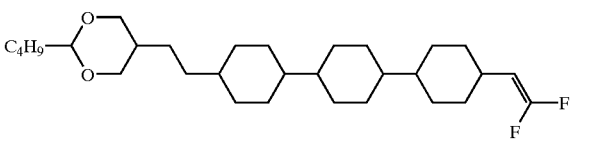
No. 204
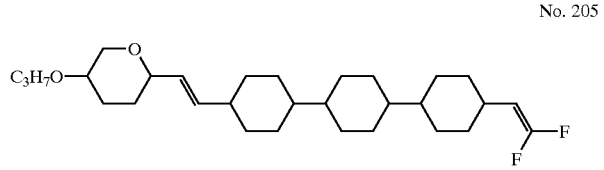
No. 205
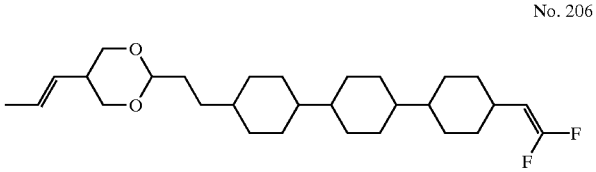
No. 206

-continued
No. 207
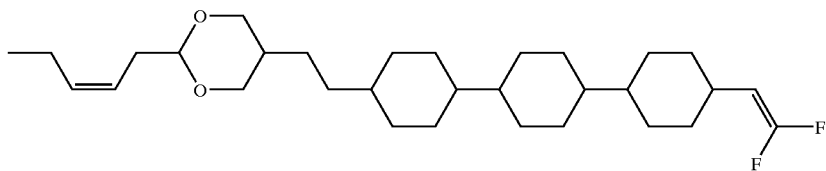
No. 208
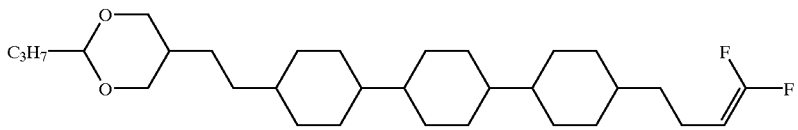
No. 209
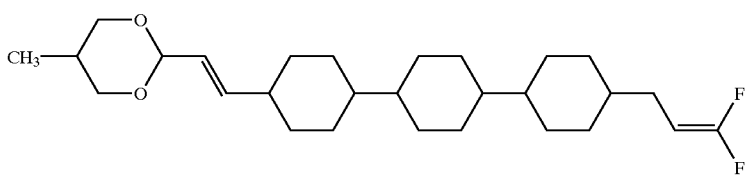
No. 210
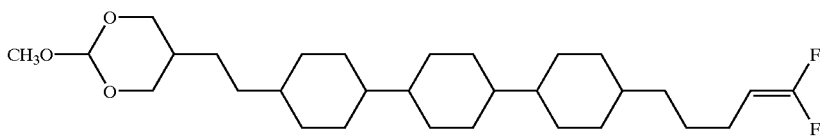
No. 211
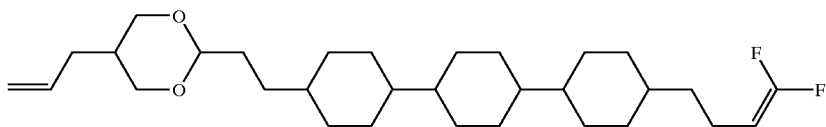
No. 212
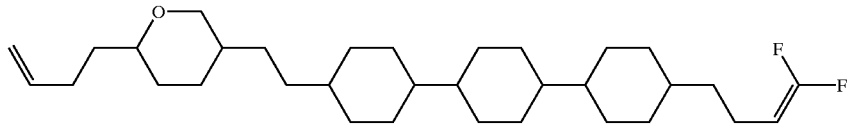
No. 213
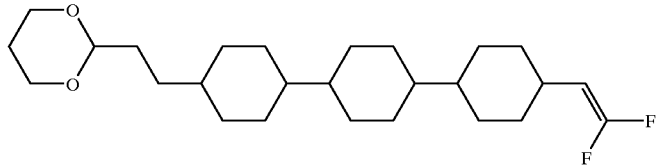
No. 214
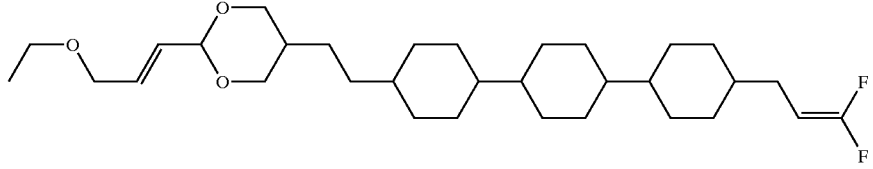
No. 215 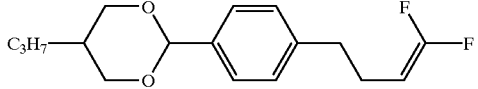 No. 216
No. 217 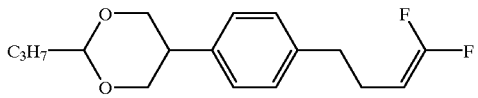 No. 218
No. 219 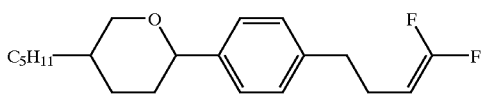 No. 220

-continued
No. 221
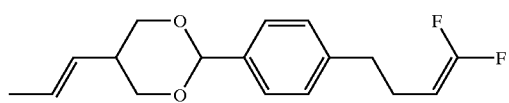
No. 222
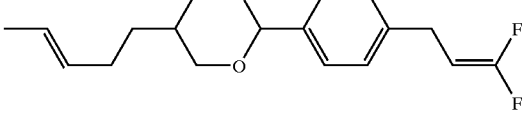
No. 223
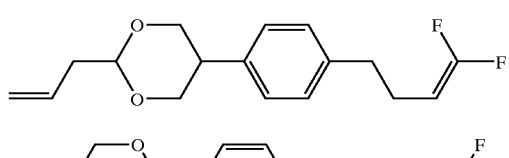
No. 224
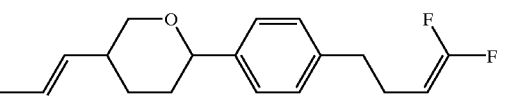
No. 225
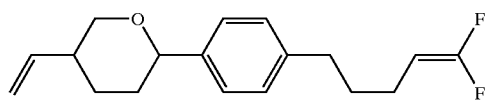
No. 226
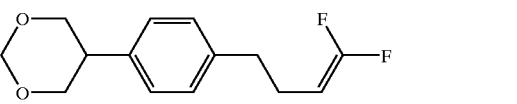
No. 227
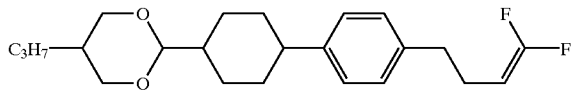
No. 228
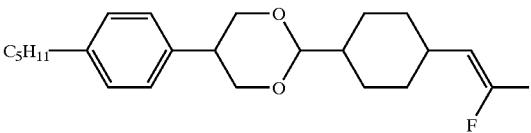
No. 229
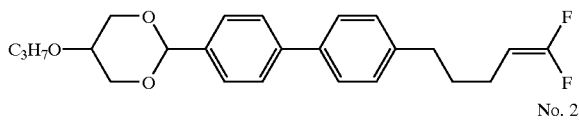
No. 230
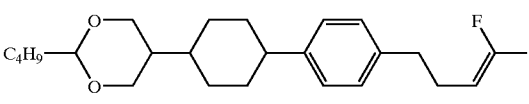
No. 231
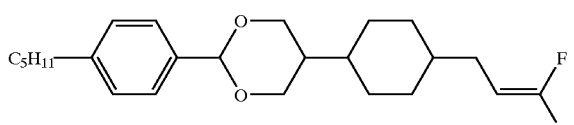
No. 232
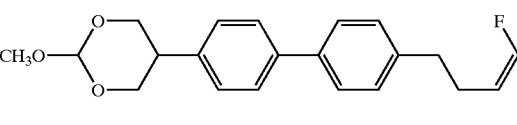
No. 233
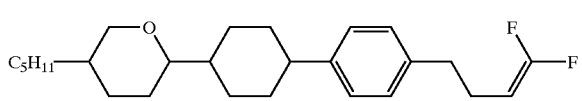
No. 234
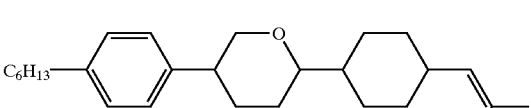
No. 235
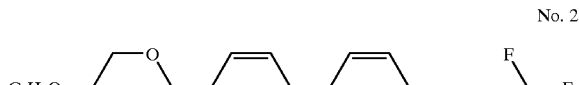
No. 236
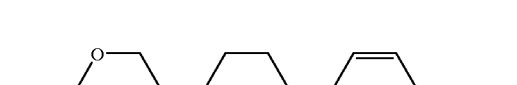
No. 237
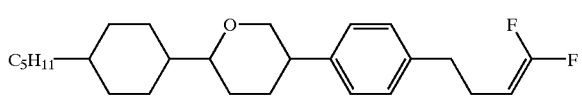
No. 238
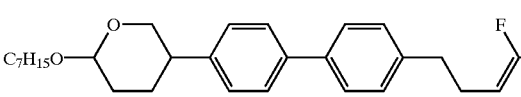
No. 239
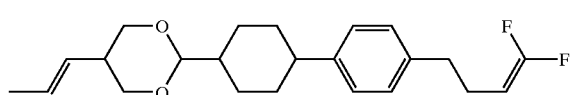
No. 240
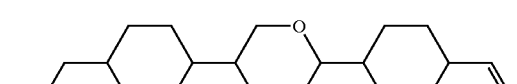
No. 241
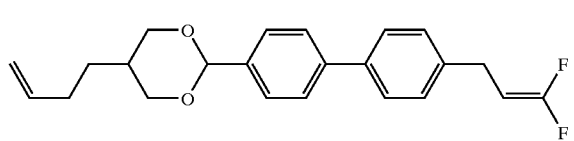
No. 242
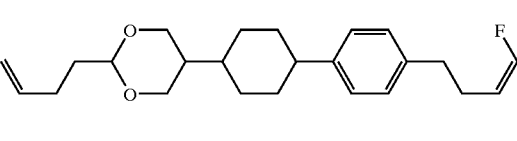

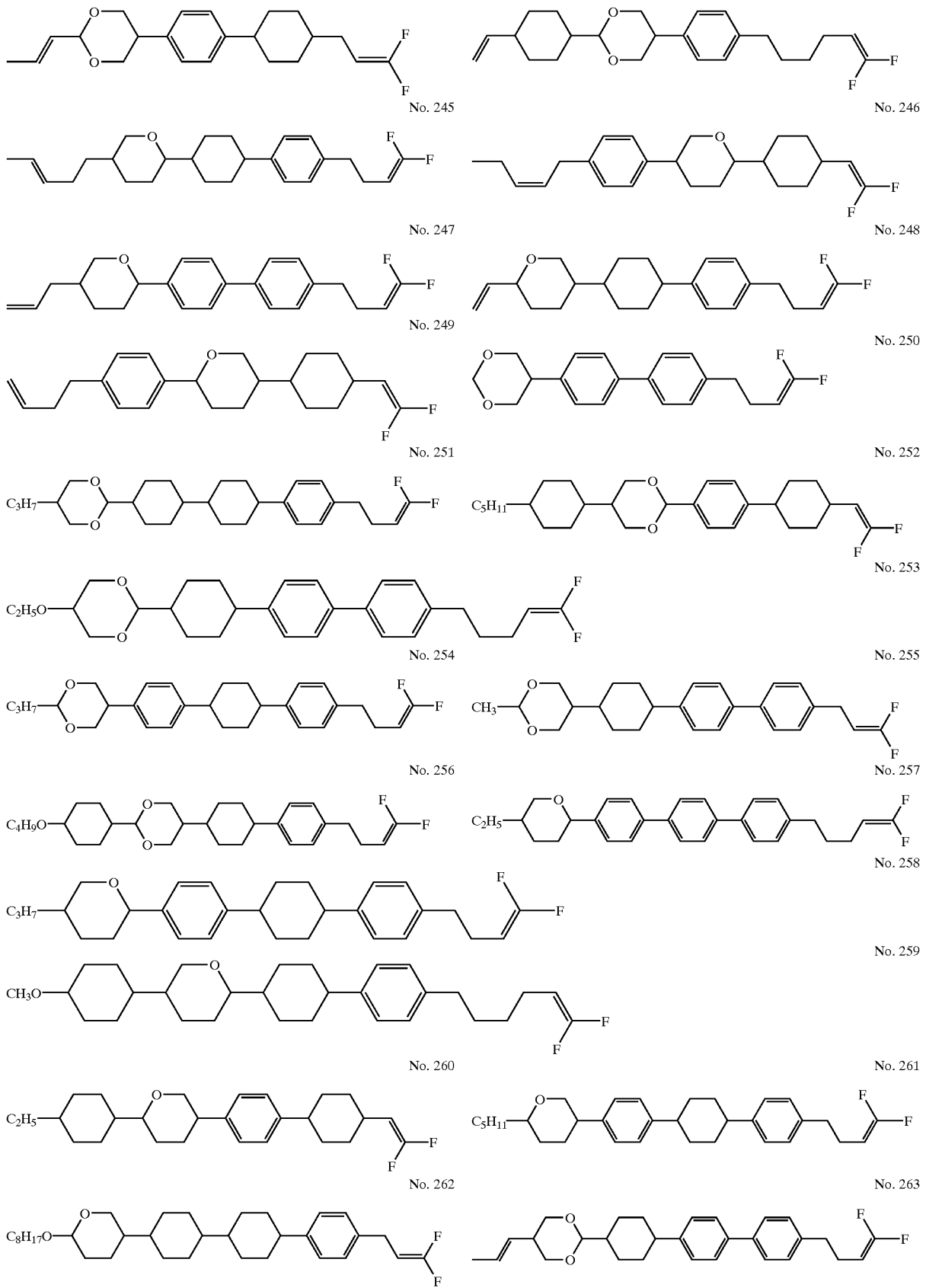

-continued
No. 264
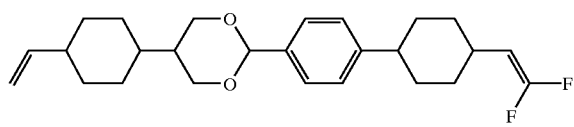
No. 265
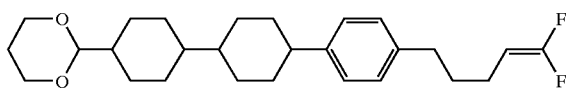
No. 266
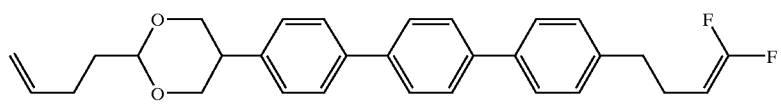
No. 267
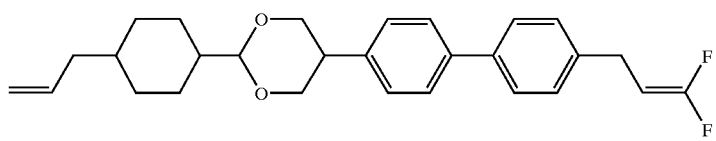
No. 268
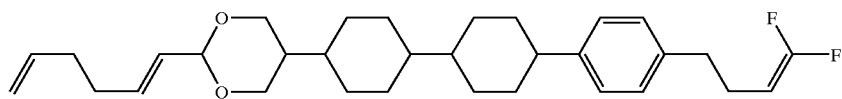
No. 269
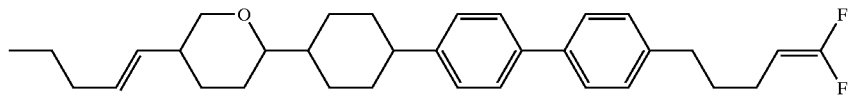
No. 270
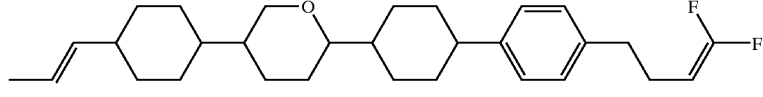
No. 271
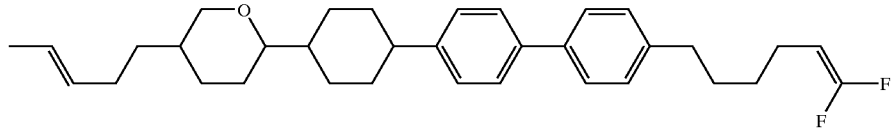
No. 272
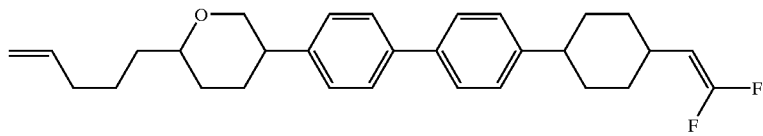
No. 273
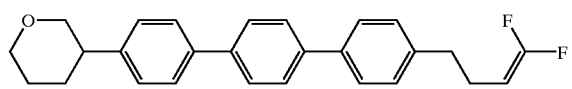
No. 274
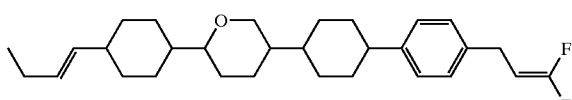
No. 275
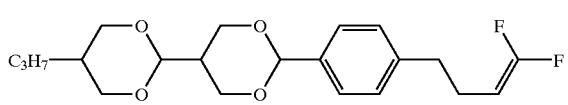
No. 276
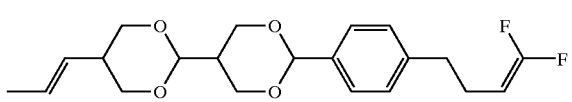
No. 277
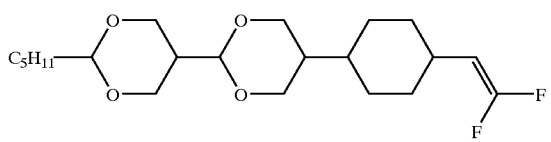
No. 278
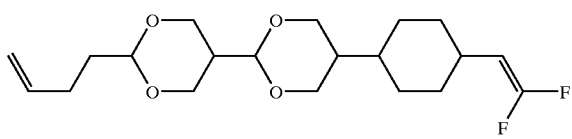
No. 279
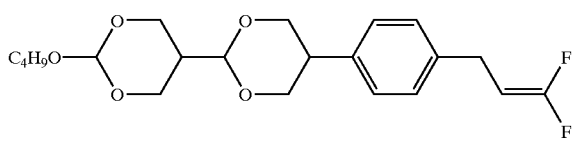
No. 280
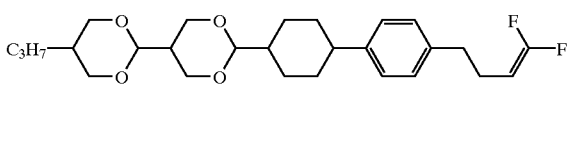

-continued
No. 281
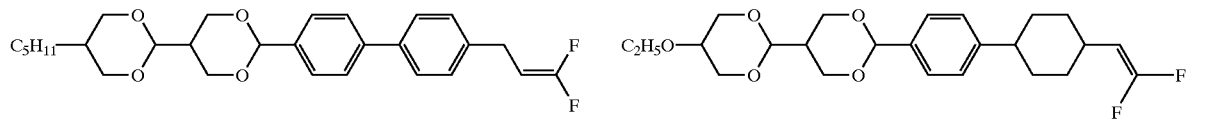
No. 282
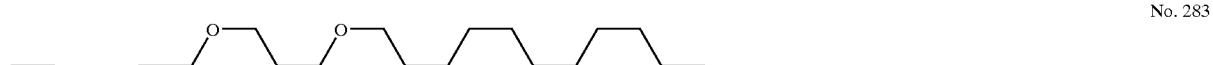
No. 283
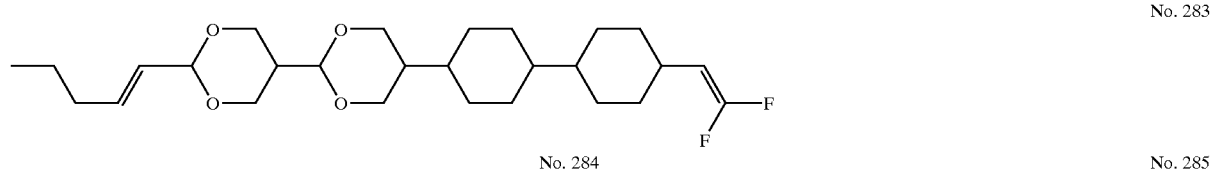
No. 284
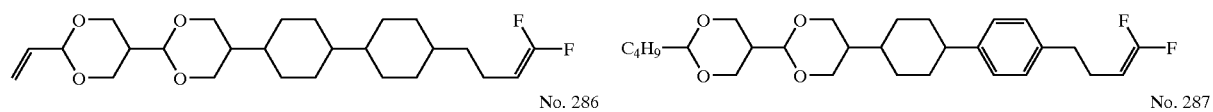
No. 285
No. 286
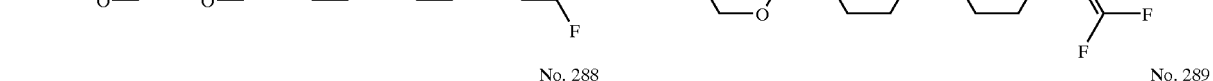
No. 287
No. 288
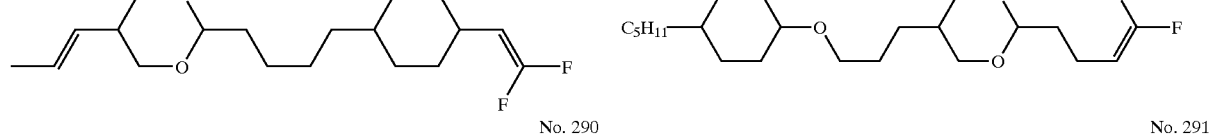
No. 289
No. 290
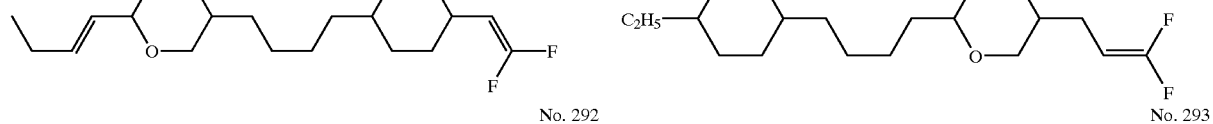
No. 291
No. 292
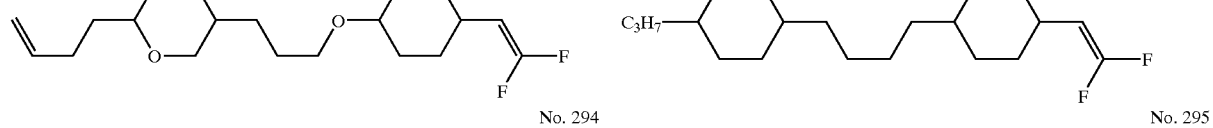
No. 293
No. 294
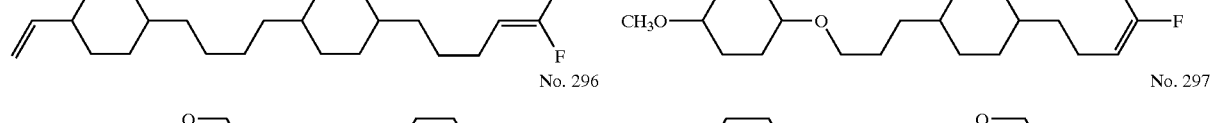
No. 295
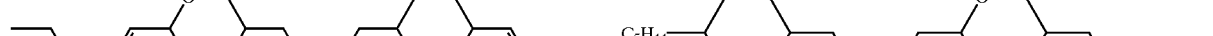
No. 296
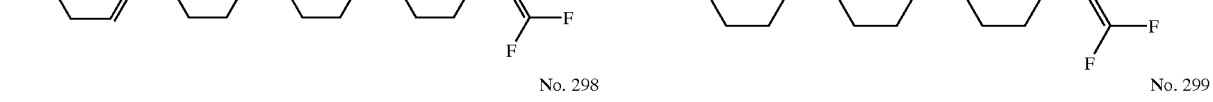
No. 297
No. 298
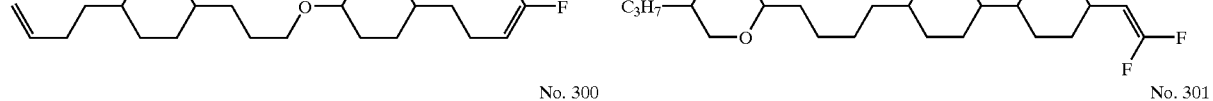
No. 299
No. 300
No. 301
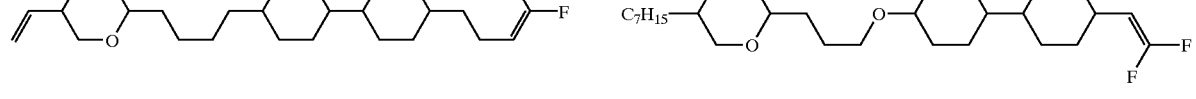

-continued
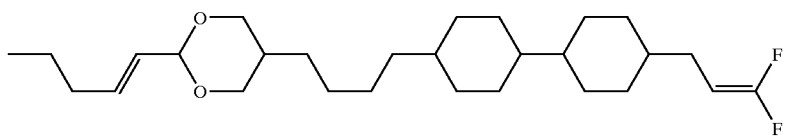
No. 302
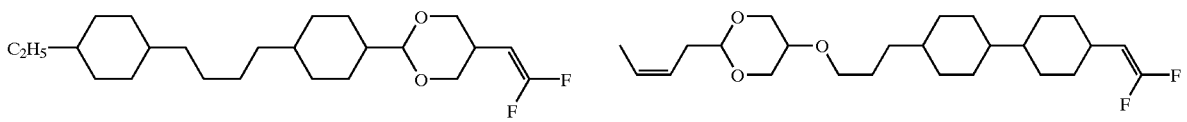
No. 303
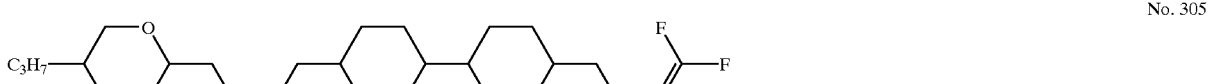
No. 304
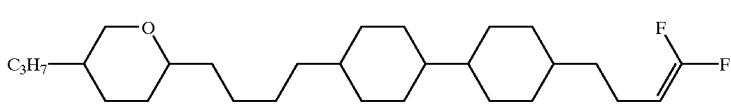
No. 305
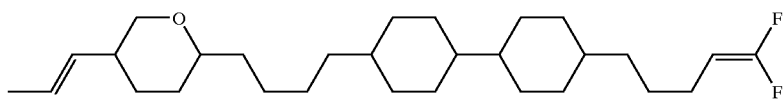
No. 306
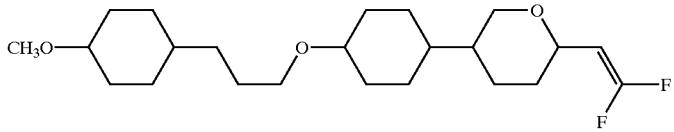
No. 307
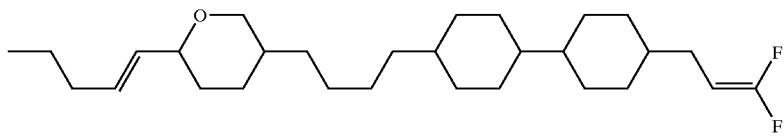
No. 308
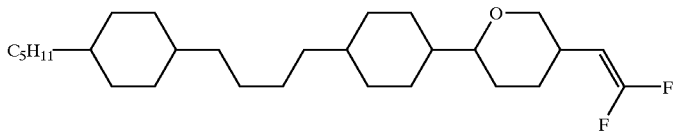
No. 309
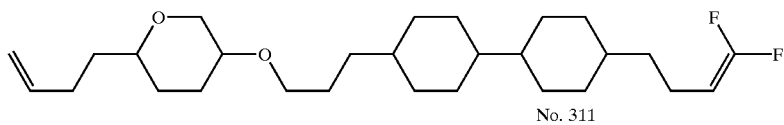
No. 310
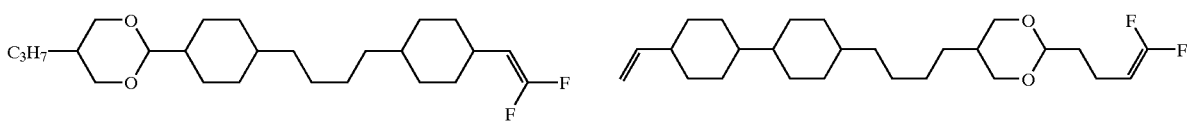
No. 311
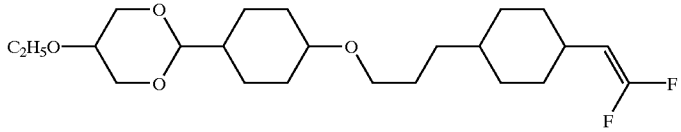
No. 312
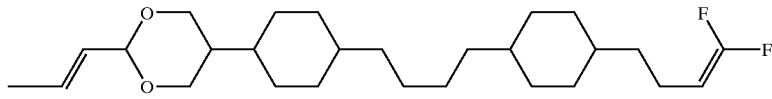
No. 313
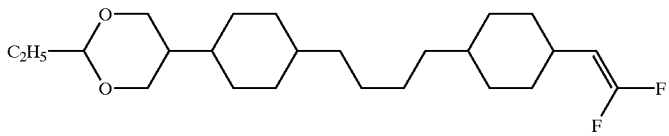
No. 314
No. 315

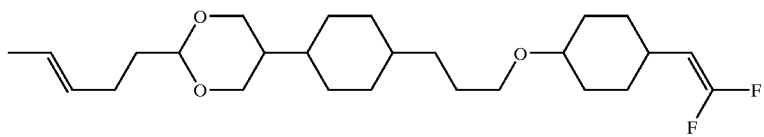
No. 316
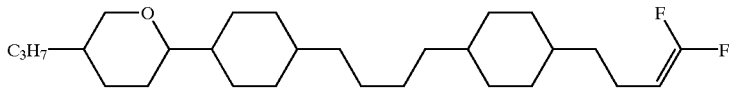
No. 317
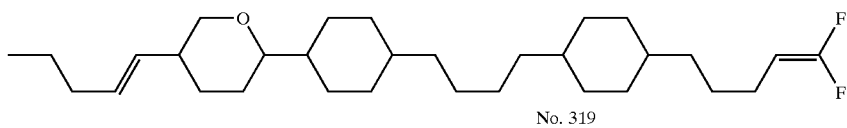
No. 318
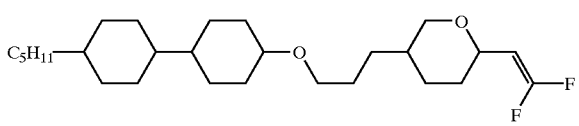
No. 319
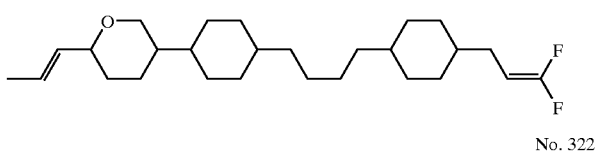
No. 320
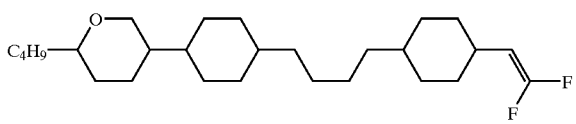
No. 321
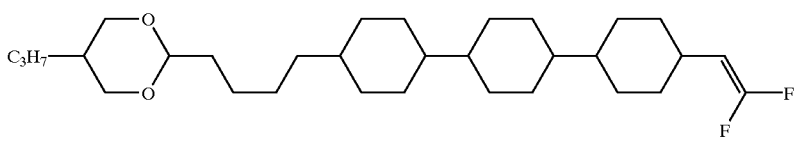
No. 322
No. 323
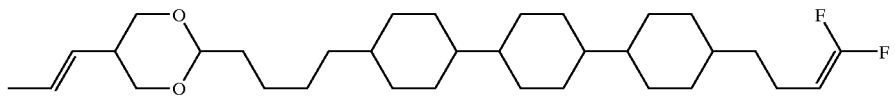
No. 324
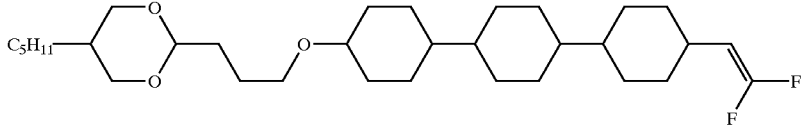
No. 325
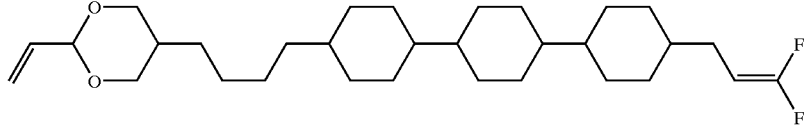
No. 326
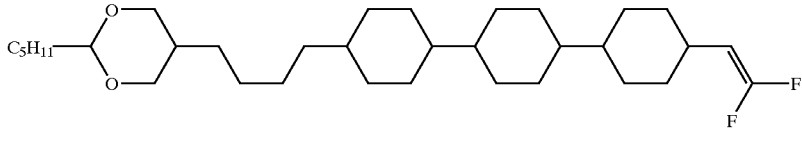
No. 327
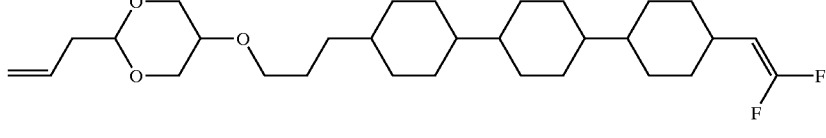
No. 328
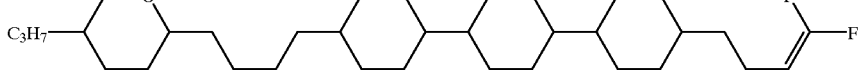
No. 329

-continued
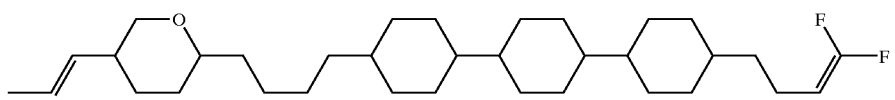
No. 330
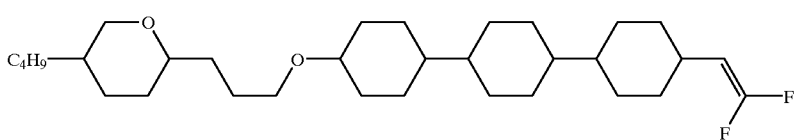
No. 331
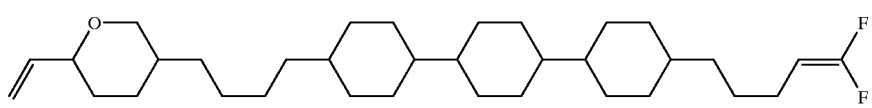
No. 332
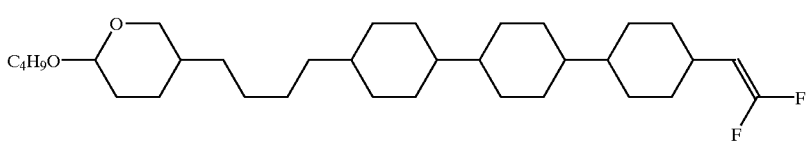
No. 333
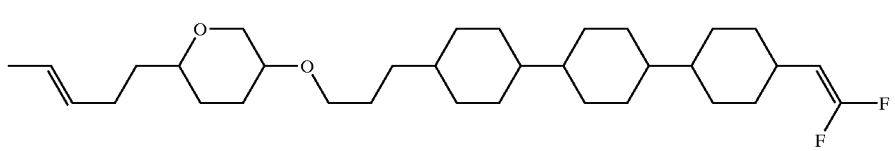
No. 334
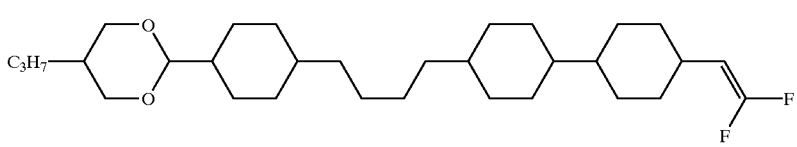
No. 335
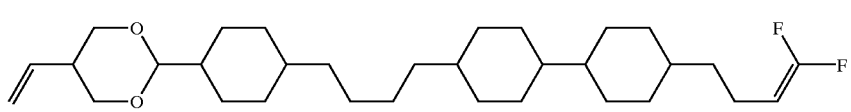
No. 336
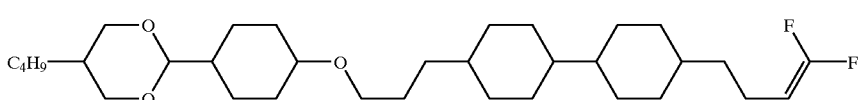
No. 337
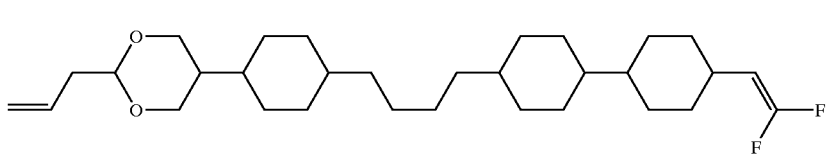
No. 338
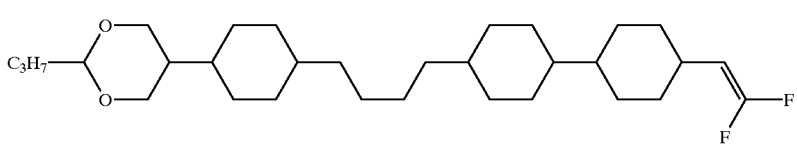
No. 339
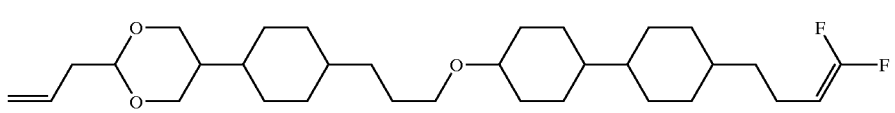
No. 340
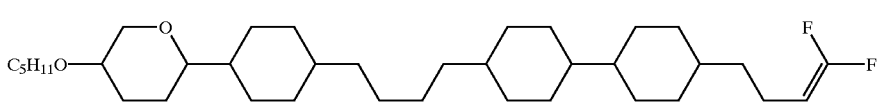
No. 341
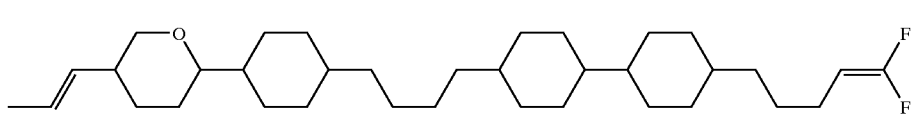
No. 342

-continued
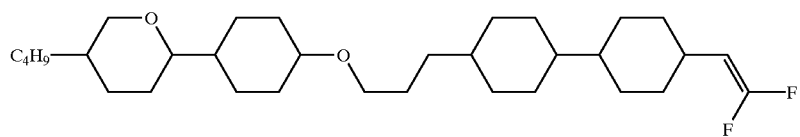 No. 343
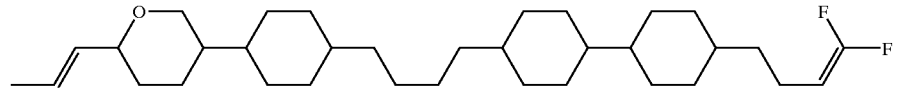 No. 344
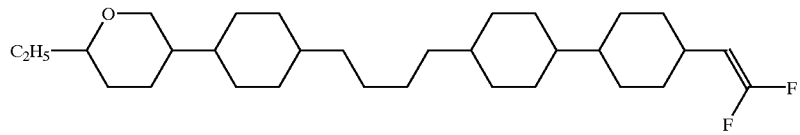 No. 345
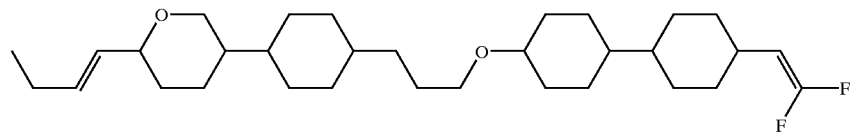 No. 346
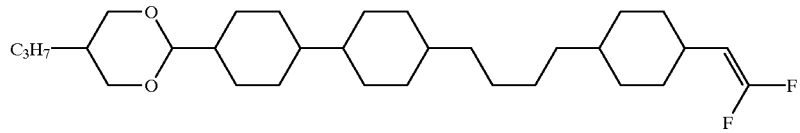 No. 347
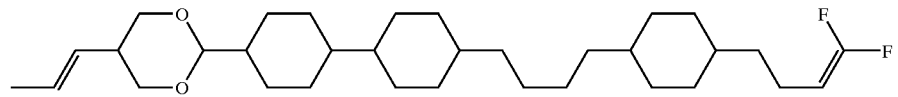 No. 348
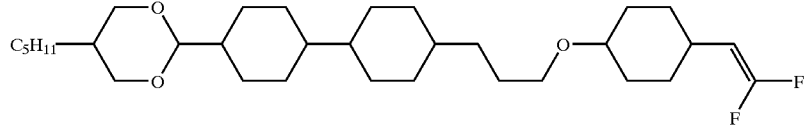 No. 349
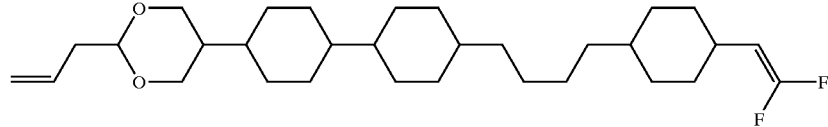 No. 350
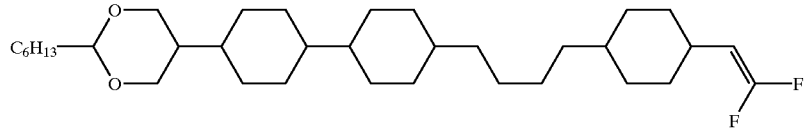 No. 351
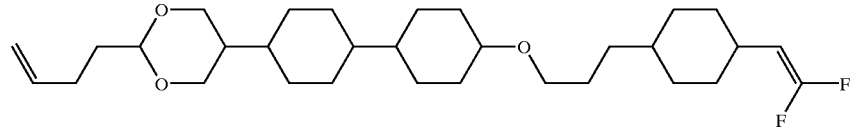 No. 352
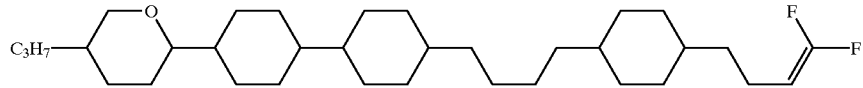 No. 353
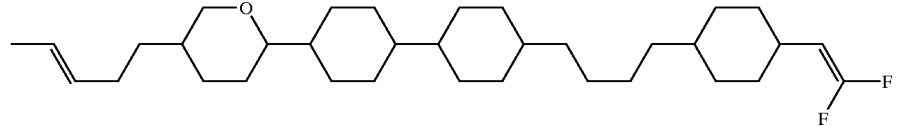 No. 354

-continued

No. 355
No. 356
No. 357
No. 358
No. 359
No. 360
No. 361
No. 362
No. 363
No. 364
No. 365
No. 366
No. 367
No. 368
No. 369
No. 370
No. 371
No. 372

No. 373
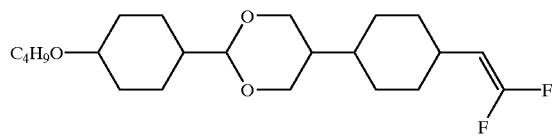
No. 374
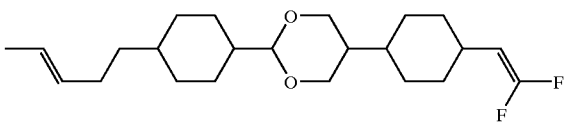
No. 375
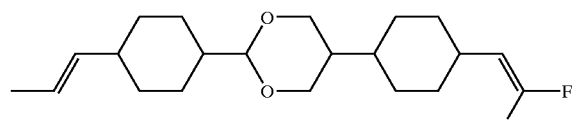
No. 376
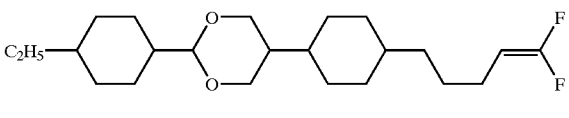
No. 377
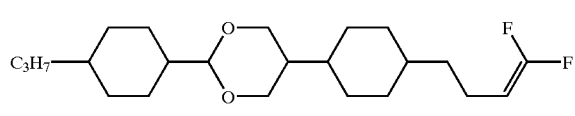
No. 378
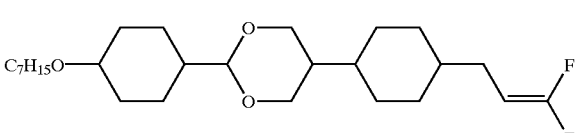
No. 379
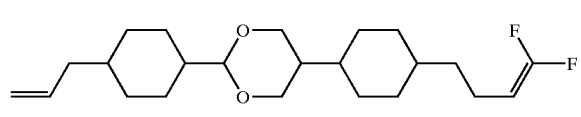
No. 380
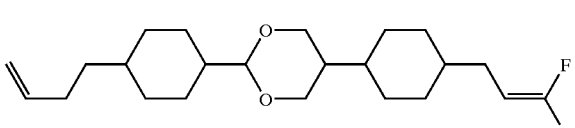
No. 381
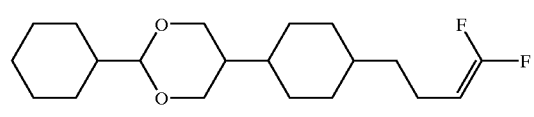
No. 382
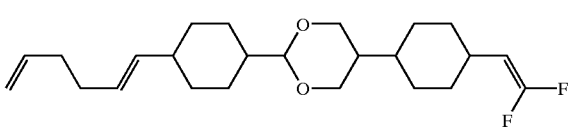
No. 383
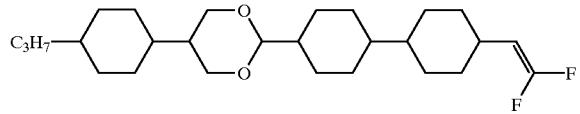
No. 384
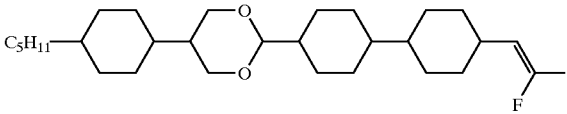
No. 385
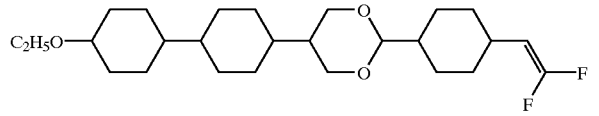
No. 386
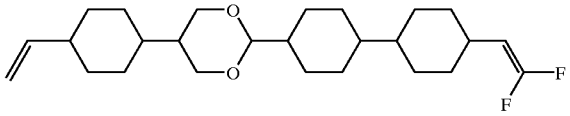
No. 387
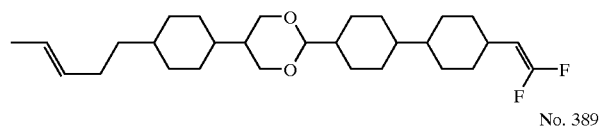
No. 388
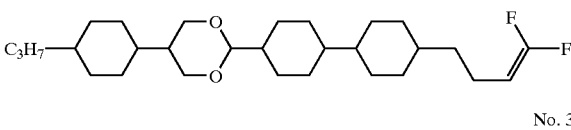
No. 389
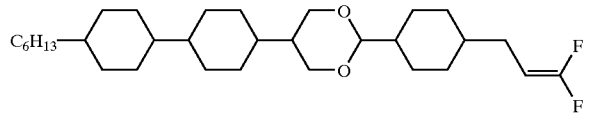
No. 390
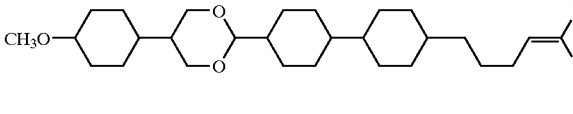
No. 391
No. 392
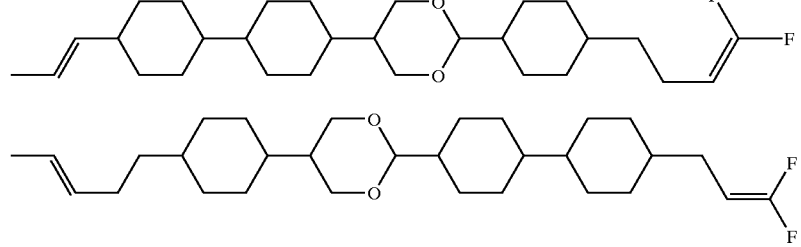

No. 393
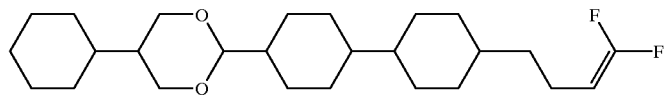
No. 394
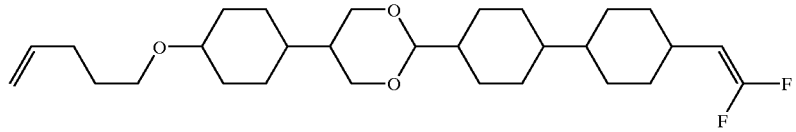
No. 395
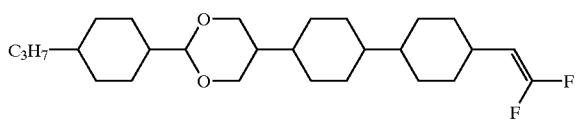
No. 396
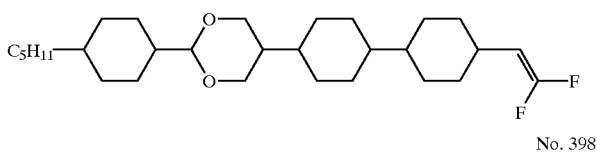
No. 397
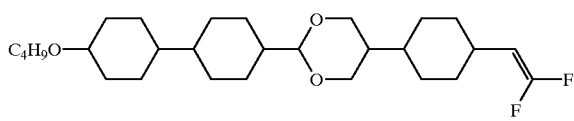
No. 398
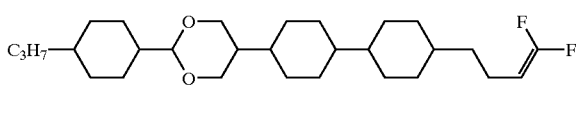
No. 399
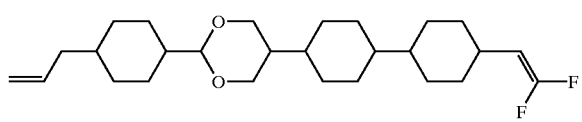
No. 400
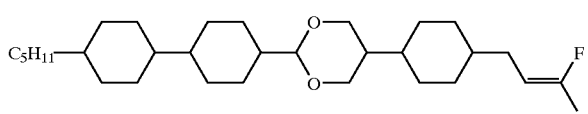
No. 401
No. 402
No. 403
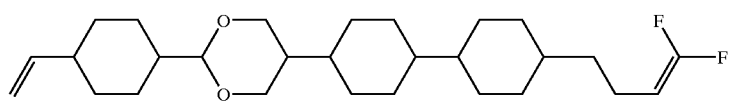
No. 404
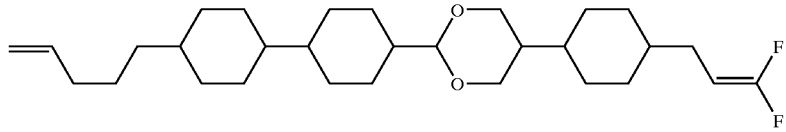
No. 405
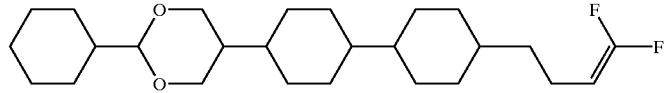
No. 406
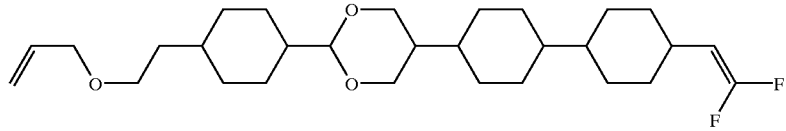
No. 407
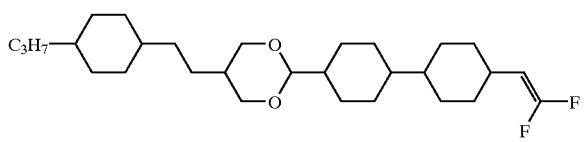
No. 408
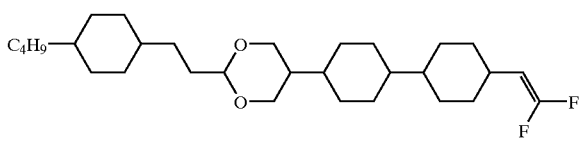

-continued
No. 409
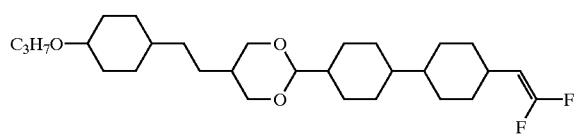
No. 410
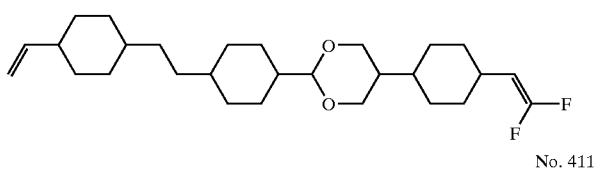
No. 411
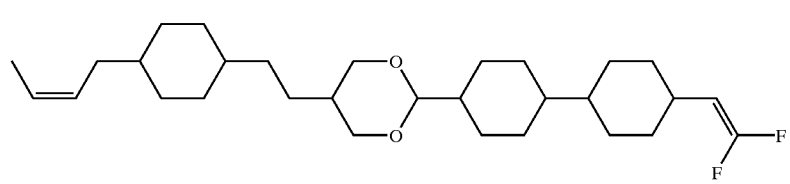
No. 412
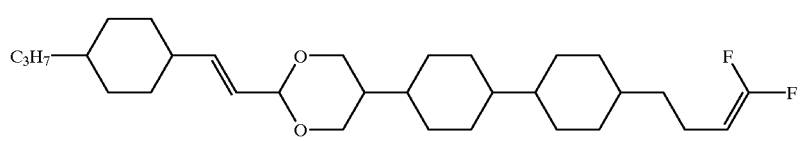
No. 413
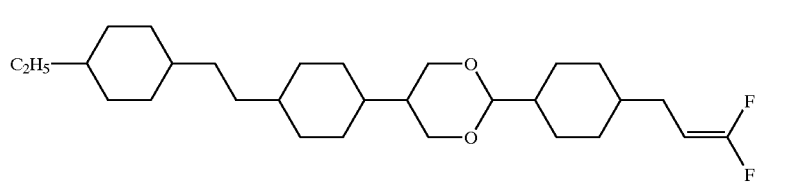
No. 414
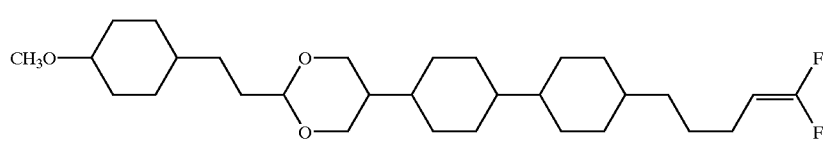
No. 415
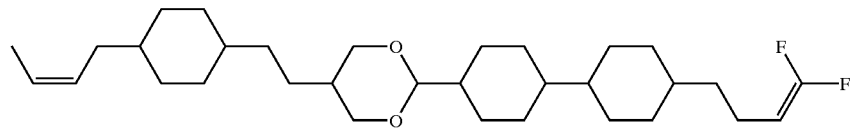
No. 416
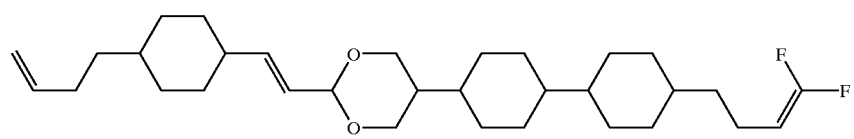
No. 417
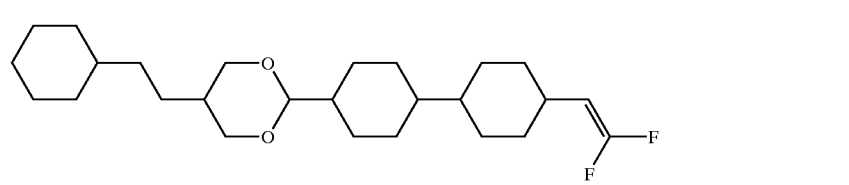
No. 418
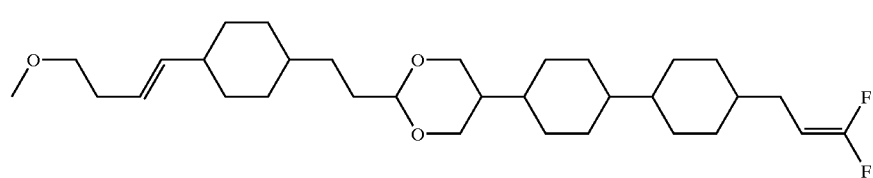
No. 419
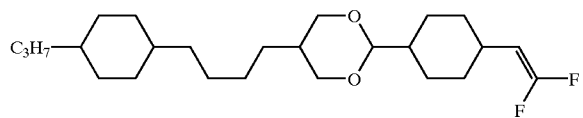
No. 420
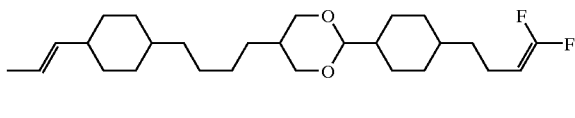

No. 421
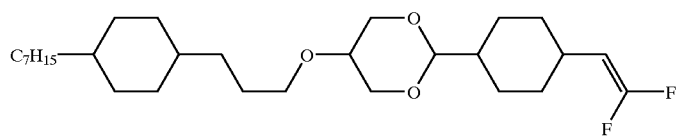
No. 422
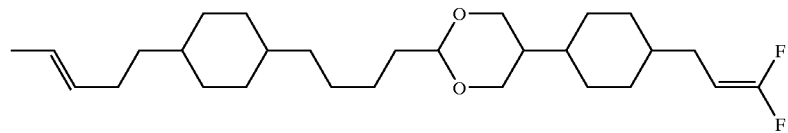
No. 423
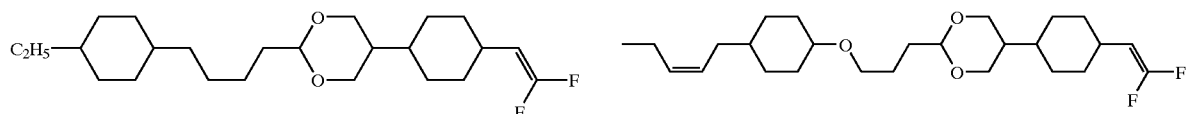
No. 425
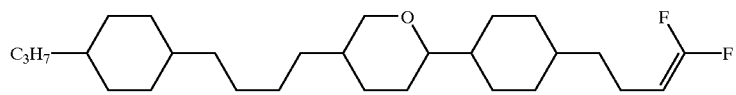
No. 426
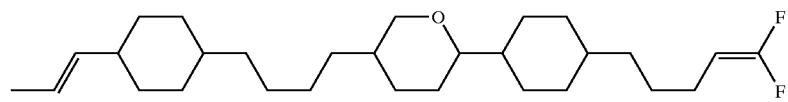
No. 427
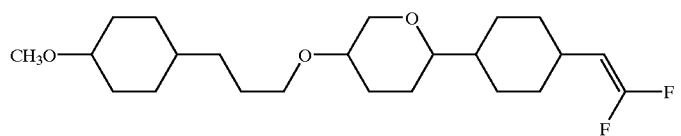
No. 428
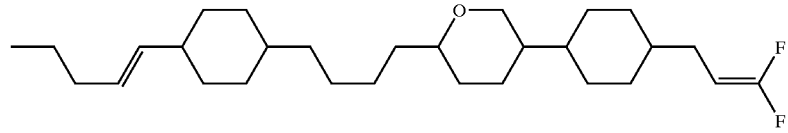
No. 429
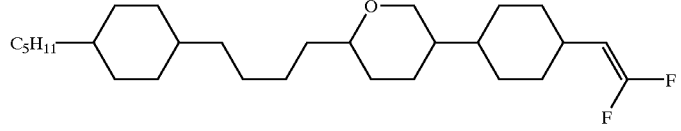
No. 430
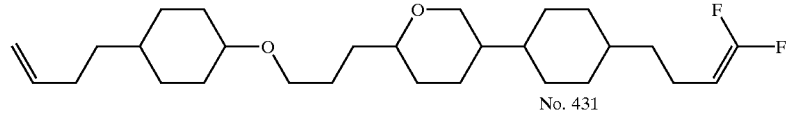
No. 431 No. 432
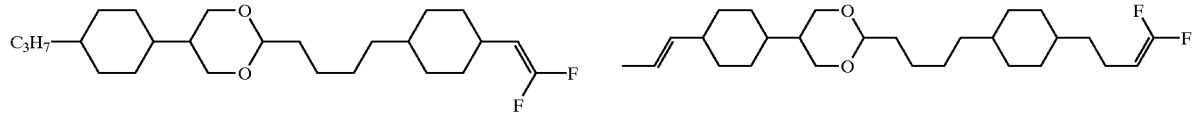
No. 433 No. 434
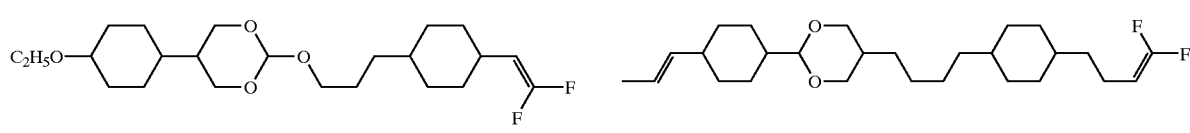
No. 435 No. 436
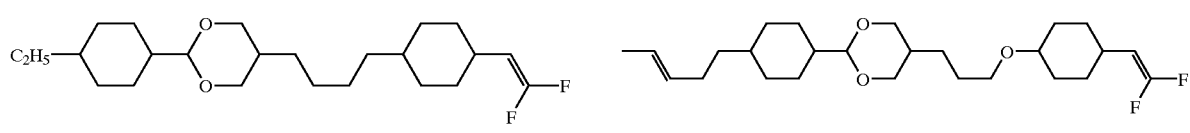

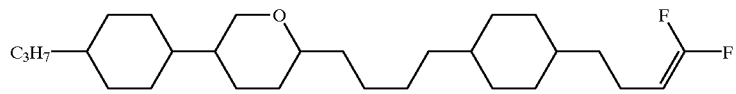
No. 437
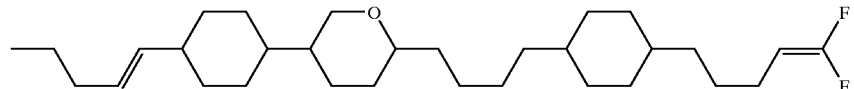
No. 438
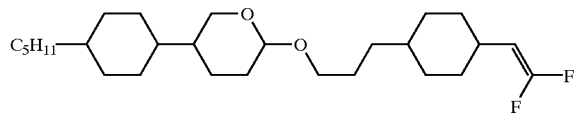
No. 439
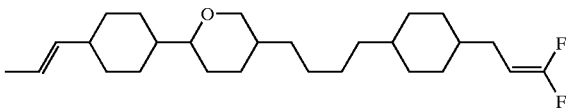
No. 440
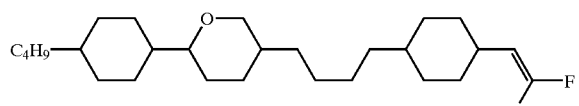
No. 441
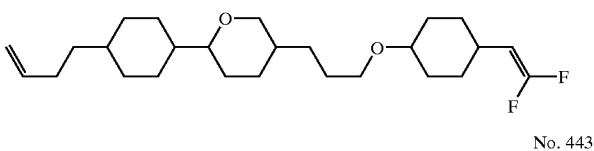
No. 442
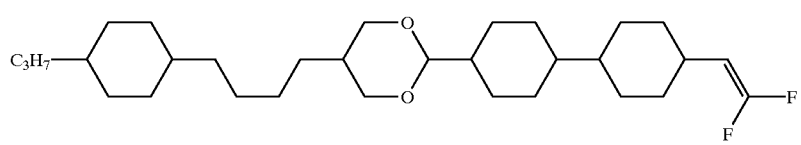
No. 443
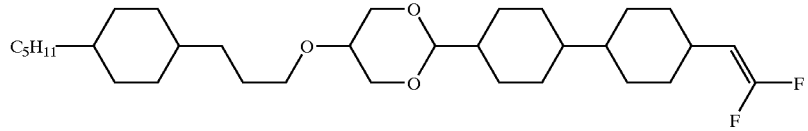
No. 444
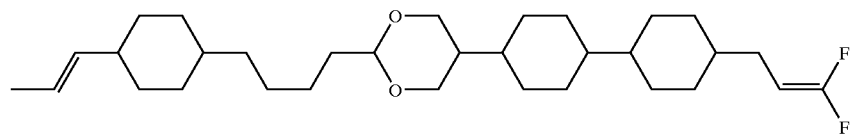
No. 445
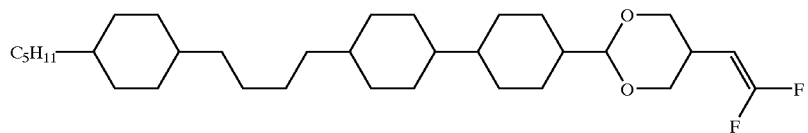
No. 446
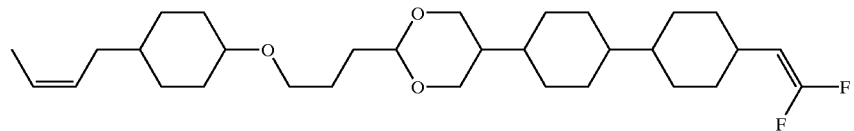
No. 447
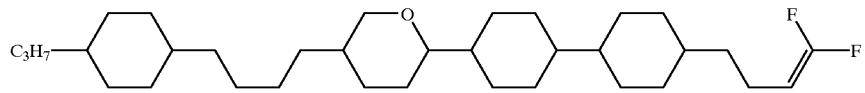
No. 448
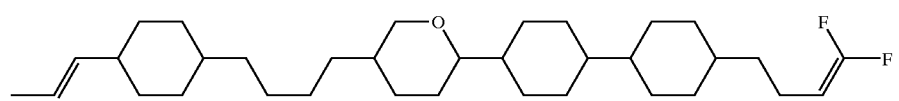
No. 449
No. 450

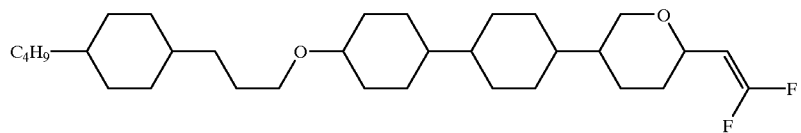
No. 451
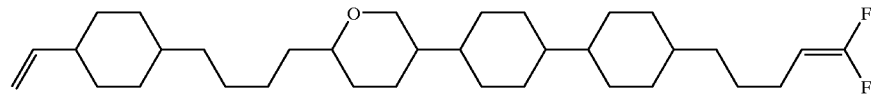
No. 452
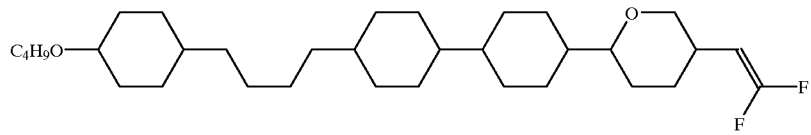
No. 453
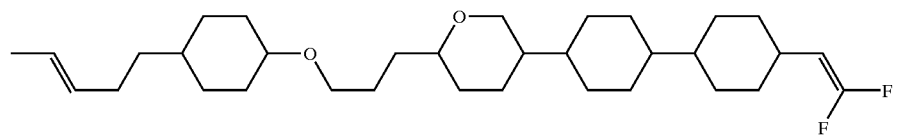
No. 454
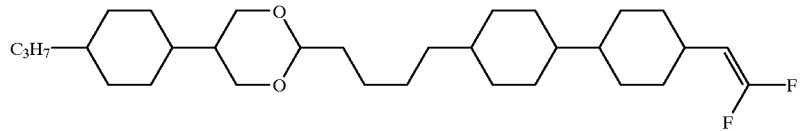
No. 455
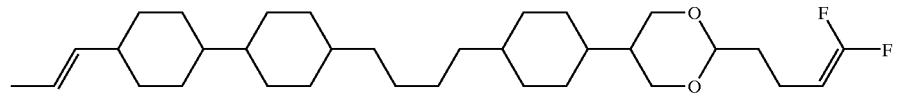
No. 456
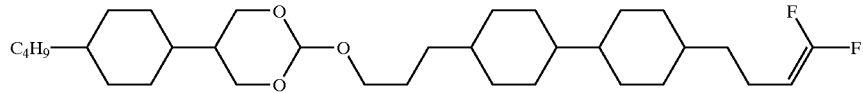
No. 457
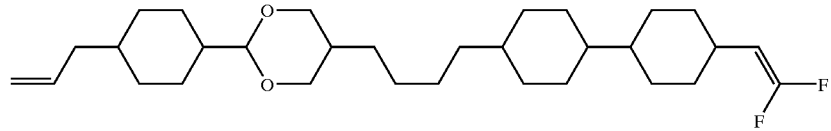
No. 458
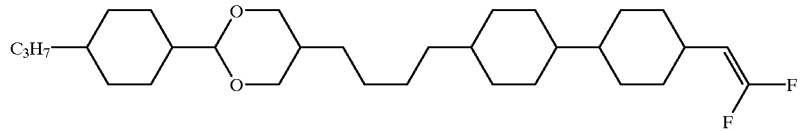
No. 459
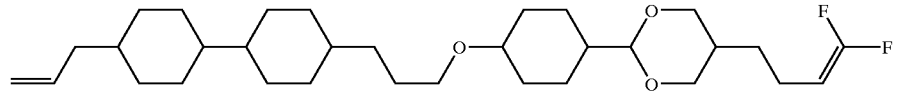
No. 460
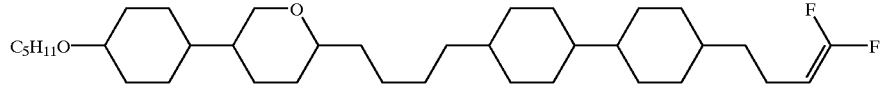
No. 461
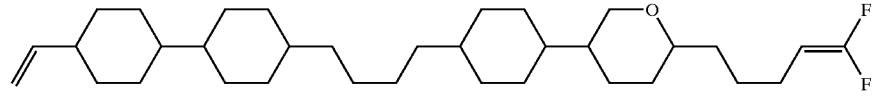
No. 462

-continued
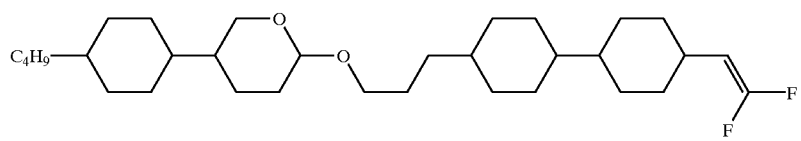
No. 463
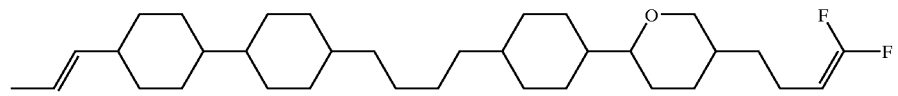
No. 464
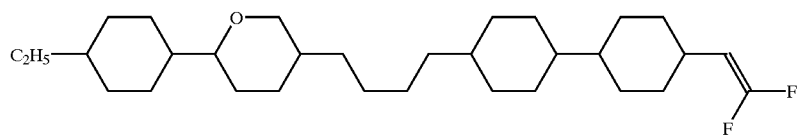
No. 465
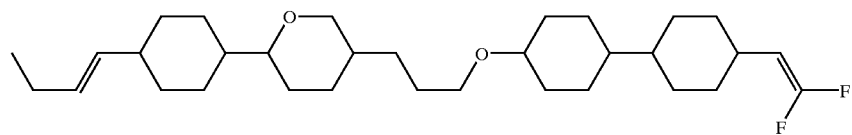
No. 466
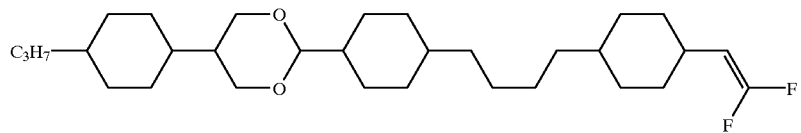
No. 467
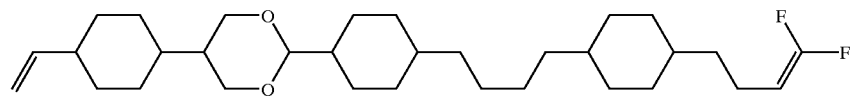
No. 468
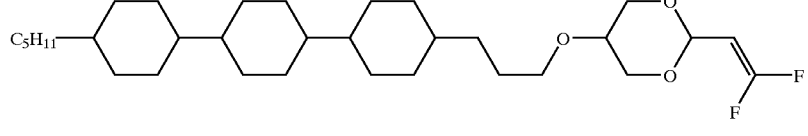
No. 469
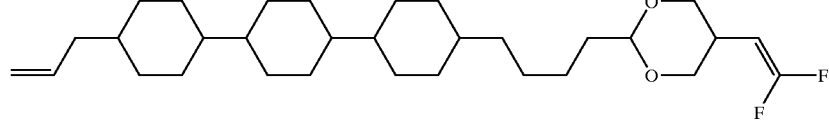
No. 470
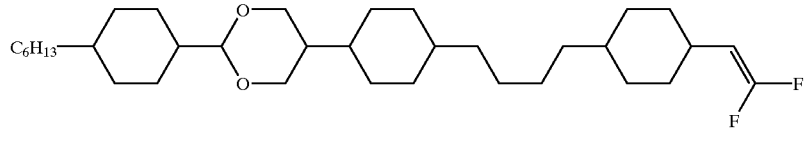
No. 471
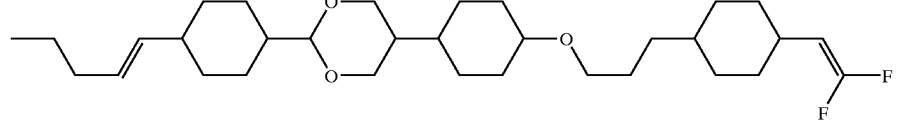
No. 472
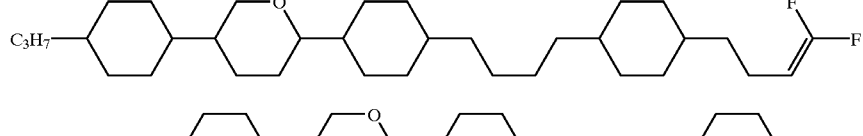
No. 473
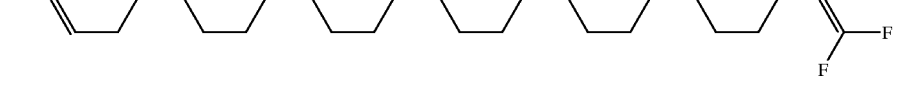
No. 474

-continued

-continued
No. 493
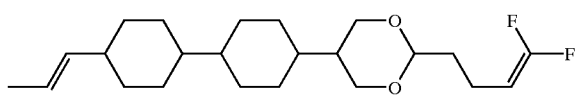
No. 494
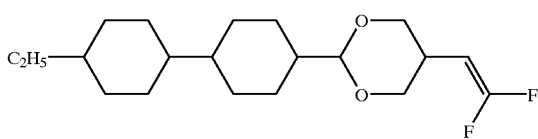
No. 495
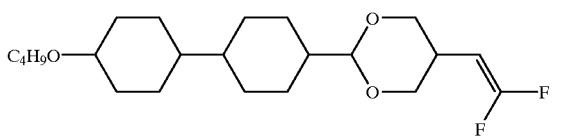
No. 496
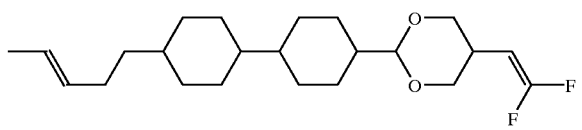
No. 497
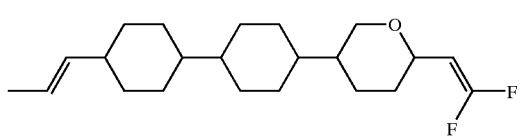
No. 498
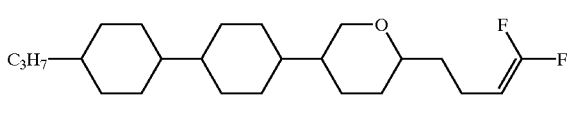
No. 499
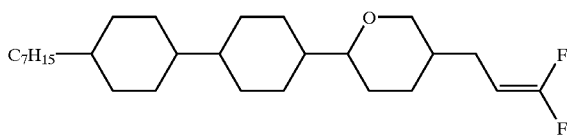
No. 500
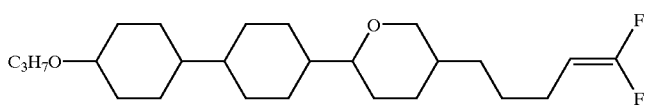
No. 501
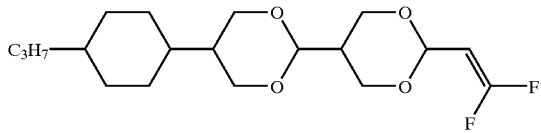
No. 502
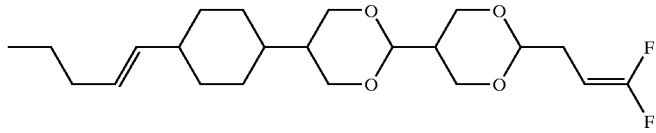
No. 503
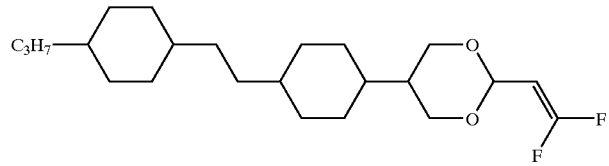
No. 504
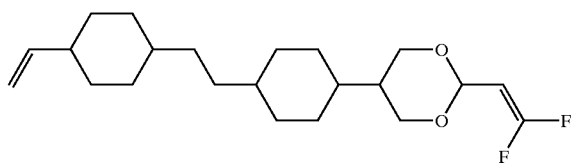
No. 505
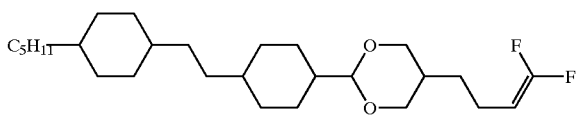

-continued
No. 506
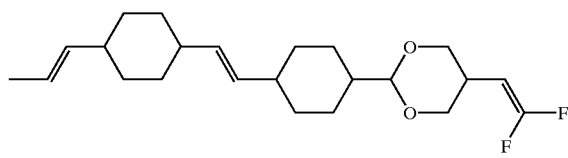
No. 507
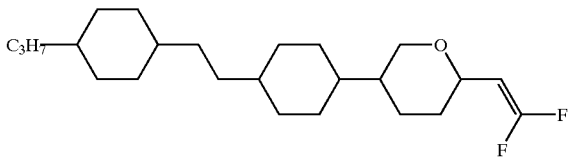
No. 508
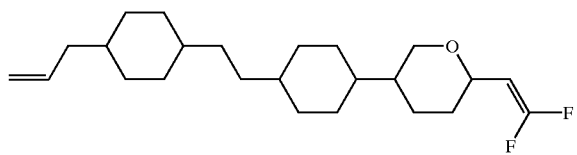
No. 509
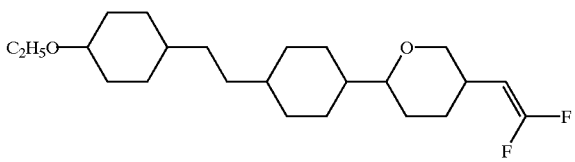
No. 510
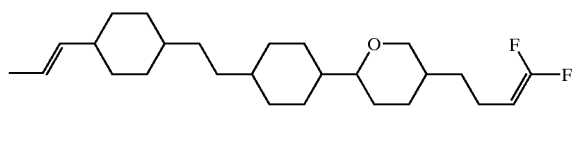
No. 511
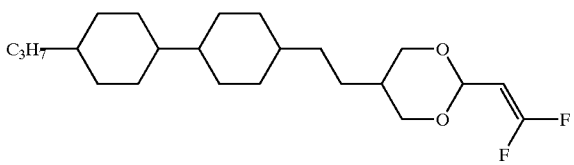
No. 512
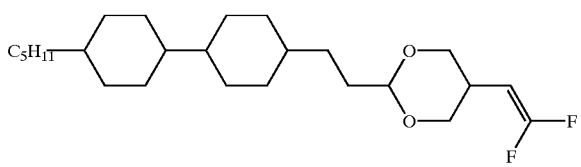
No. 513
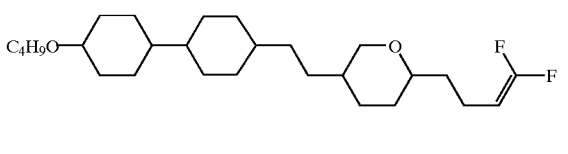
No. 514
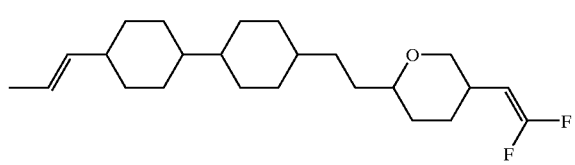
No. 515
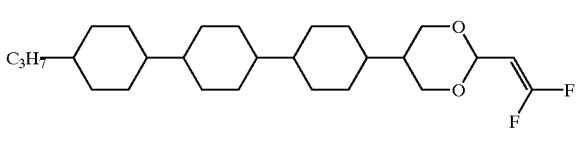
No. 516
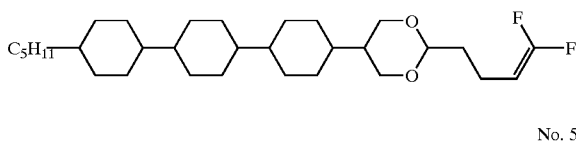
No. 517
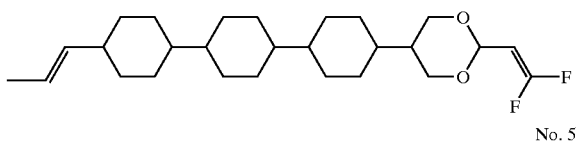
No. 518
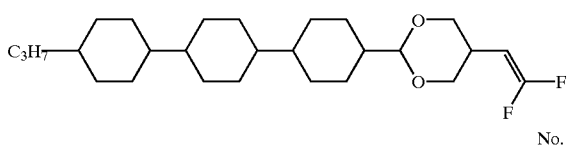
No. 519
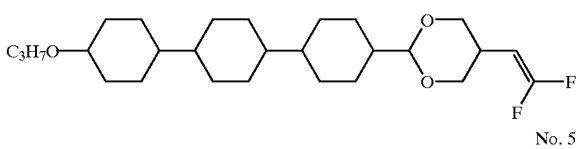
No. 520
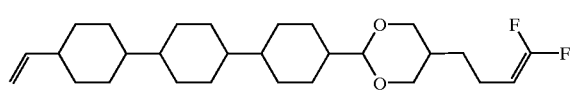
No. 521
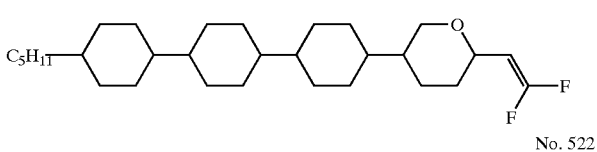
No. 522
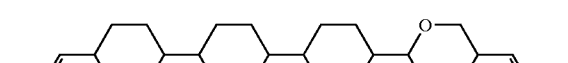
No. 523
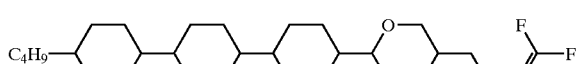
No. 524
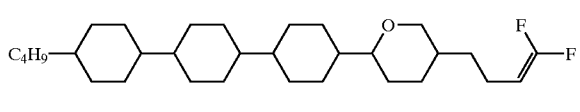

-continued
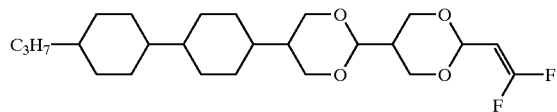
No. 525
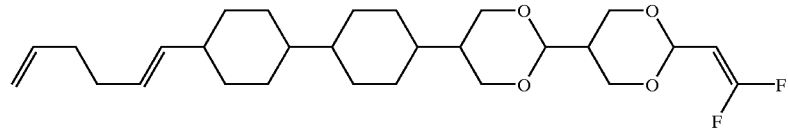
No. 526
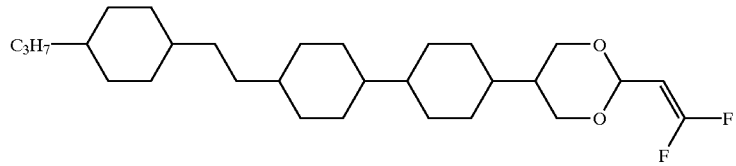
No. 527
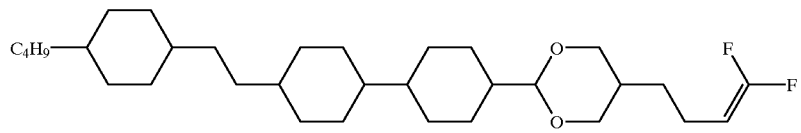
No. 528
No. 529
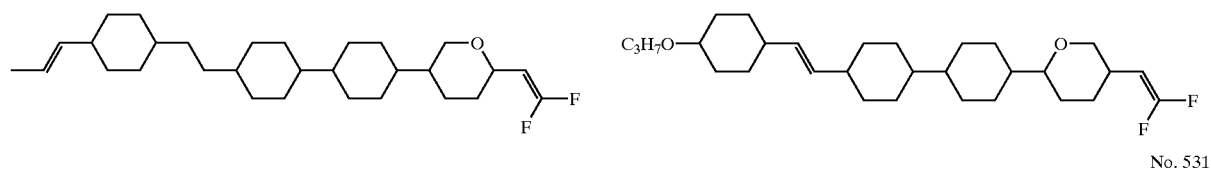
No. 530
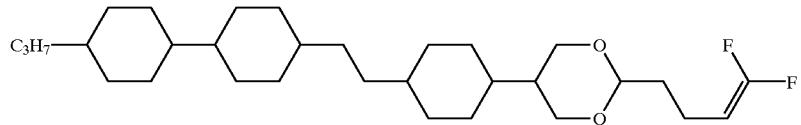
No. 531
No. 532
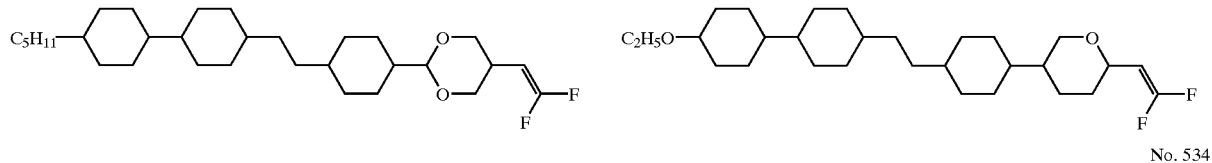
No. 533
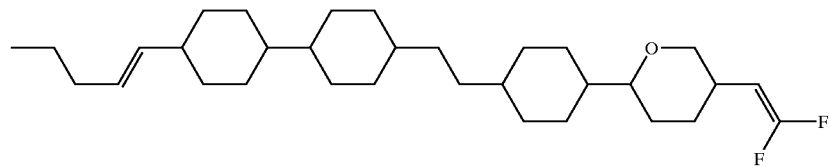
No. 534
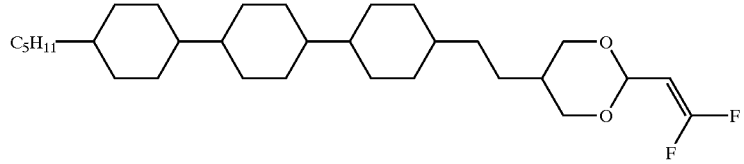
No. 535
No. 536
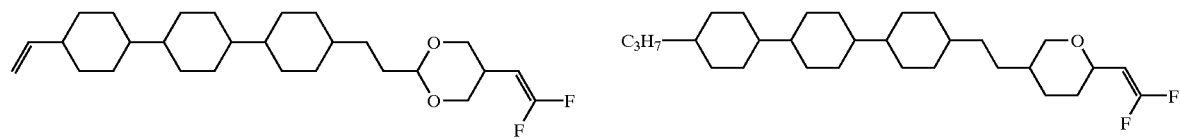
No. 537

-continued

No. 538, No. 539, No. 540, No. 541, No. 542, No. 543, No. 544, No. 545, No. 546, No. 547, No. 548, No. 549, No. 550, No. 551, No. 552, No. 553, No. 554, No. 555, No. 556

-continued
No. 557
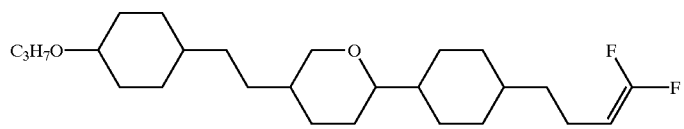
No. 558
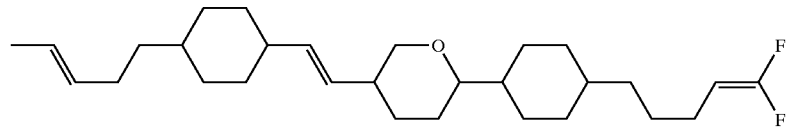
No. 559
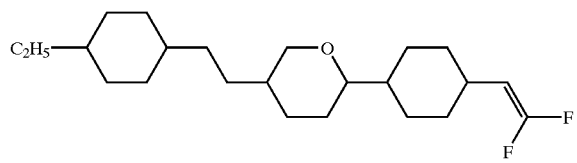
No. 560
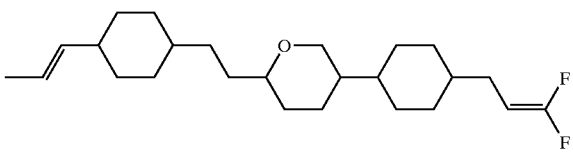
No. 561
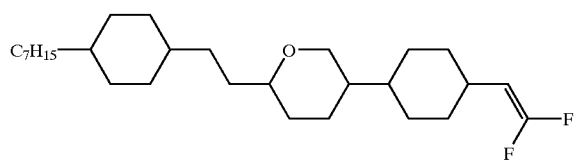
No. 562
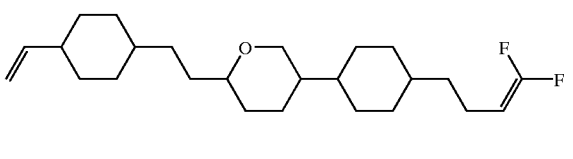
No. 563
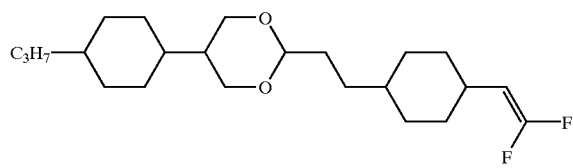
No. 564
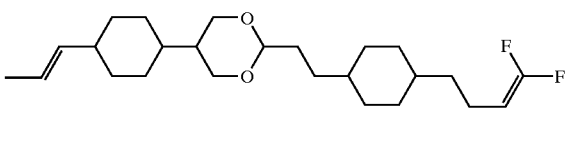
No. 565
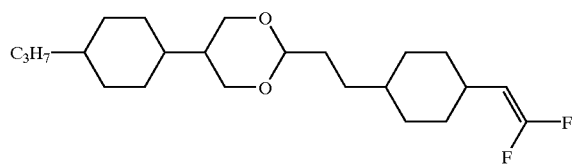
No. 566
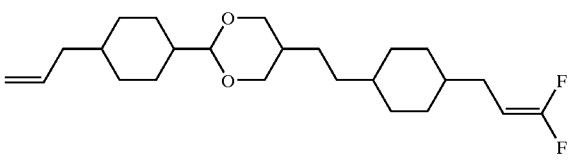
No. 567
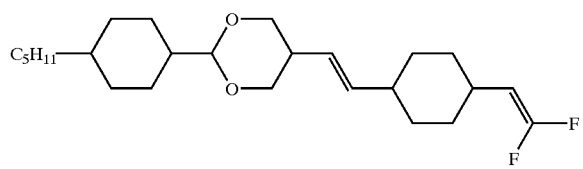
No. 568
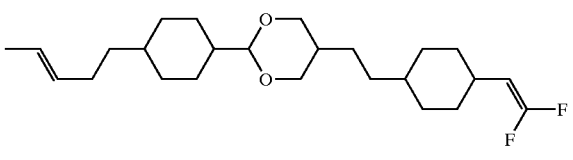
No. 569
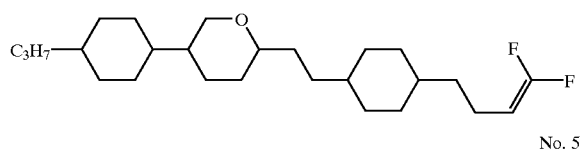
No. 570
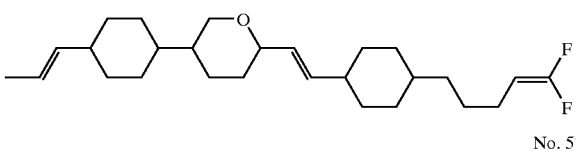
No. 571
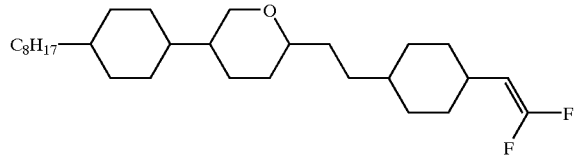
No. 572
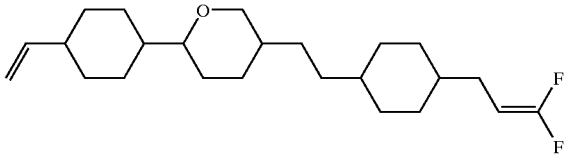

No. 573
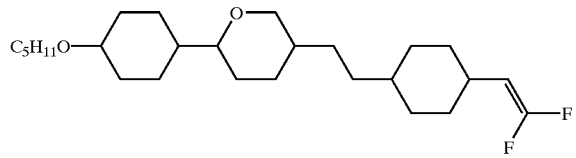

No. 574
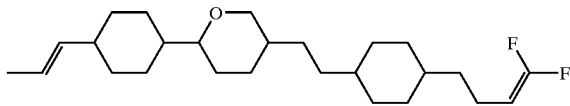

Examples in which the compounds of the present invention are used as components for the liquid crystal compositions shall be shown below. The compounds used in the composition examples and the examples described later were represented by codes exhibited by definitions which were shown in the following Table 1.

TABLE 1

Representation of compounds by the symbols

| 1) Left terminal group R— | Symbol | 3) Bonding group —Z1—, —Zn— | Symbol |
|---|---|---|---|
| $C_nH_{2n+1}$— | n— | —$C_2H_4$— | 2 |
| $C_nH_{2n+1}O$— | nO— | —$C_4H_8$— | 4 |
| $C_nH_{2n+1}OC_mH_{2m}$— | nOm— | —$CH_2O$— | 10 |
| $CH_2$=CH— | V— | —COO— | E |
| $CH_2$=$CHC_nH_{2n}$— | Vn— | —C≡C— | T |
| $C_nH_{2n+1}CH$=$CHC_mH_{2m}$— | nVm— | —CH=CH— | V |
| $CF_2$=CH— | VFF— | —$CF_2O$— | CF2O |
| $CF_2$=$CHC_nH_{2n}$— | VFFn— | | |

| 2) Ring structure —(A1)—, (An)— | Symbol | 4) Right terminal group —X | Symbol |
|---|---|---|---|
|  | B | —F | —F |
| 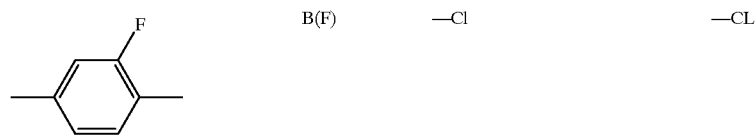 | B(F) | —Cl | —CL |
| 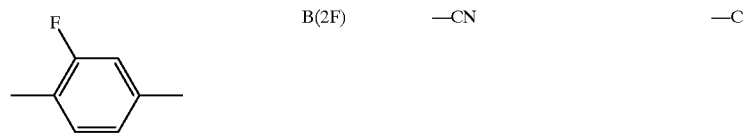 | B(2F) | —CN | —C |
| 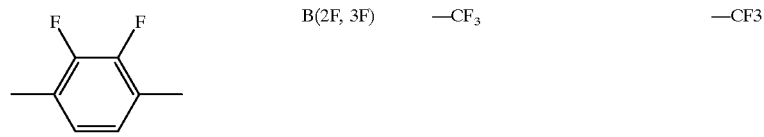 | B(2F, 3F) | —$CF_3$ | —CF3 |
| 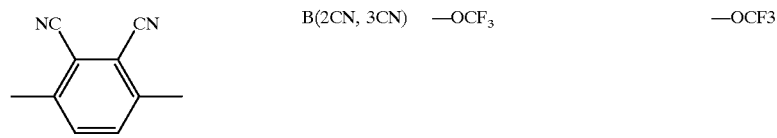 | B(2CN, 3CN) | —$OCF_3$ | —OCF3 |

TABLE 1-continued

Representation of compounds by the symbols $$R-(A_1)-Z_1-\cdots\cdots-Z_n-(A_n)-X$$

| Structure | Symbol | Group | Code |
|---|---|---|---|
| (benzene with 2 F) | B(F, F) | —OCF$_2$H | —OCF2H |
| (cyclohexane) | H | —C$_n$H$_{2n+1}$ | —n |
| (pyrimidine) | Py | —OC$_n$H$_{2n+1}$ | —On |
| (dioxane) | G | —COOCH$_3$ | —EMe |
| (cyclohexene) | Ch | —C$_n$H$_{2n}$CH=CH$_2$ | —nV |
| | | —C$_m$H$_{2m}$CH=CHC$_n$H$_{2n+1}$ | —mVn |
| | | —C$_m$H$_{2m}$CH=CHC$_n$H$_{2n}$F | —mVnF |
| | | —CH=CF$_2$ | —VFF |
| | | —C$_n$H$_{2n}$CH=CF$_2$ | —nVFF |

5) Examples of expression

Example 1; 3-GHH-VFF

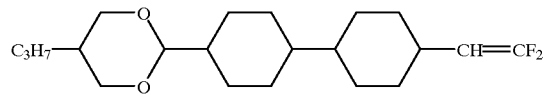

Example 2; 3-HB(F)TB-2

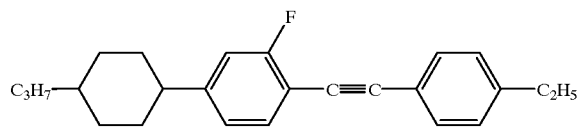

Example 3; 1V2-BEB(F,F)-C

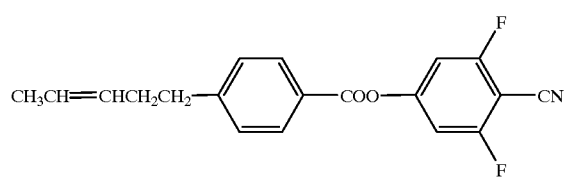

In the composition examples and the examples, [%] represents [weight %] unless otherwise described, and when a cis-trans isomer is present in the compound, the compound is a trans type. When a left terminal group is not described, the group represents a hydrogen atom.

Example 3

| | |
|---|---|
| 3-GH-VFF | 5.0% |
| 3-G2HH-VFF | 5.0% |
| 3-GHH-2VFF | 4.0% |
| 1V2-BEB (F, F) -C | 5.0% |
| 3-HB-C | 25.0% |
| 1-BTB-3 | 5.0% |
| 2-BTB-1 | 10.0% |
| 3-HH-4 | 6.0% |
| 3-HHB-1 | 11.0% |
| 3-H2BTB-2 | 4.0% |
| 3-H2BTB-3 | 4.0% |
| 3-H2BTB-4 | 4.0% |
| 3-HB (F) TB-2 | 6.0% |
| 3-HB (F) TB-3 | 6.0% |
| NI = 87.0 (° C.) | |
| η = 15.1 (mPa · s) | |
| Δn = 0.162 | |
| Δε = 7.6 | |
| Vth = 2.03 (V) | |

When adding 0.8 part of CM33 to 100 parts of the composition described above, the pitch was 11.4 μm.

Example 4

| | |
|---|---|
| 3-GHH-VFF | 4.0% |
| 2O1-BEB (F) -C | 5.0% |
| 3O1-BEB (F) -C | 15.0% |
| 4O1-BEB (F) -C | 13.0% |
| 5O1-BEB (F) -C | 13.0% |
| 2-HHB (F) -C | 15.0% |
| 3-HHB (F) -C | 15.0% |
| 3-HB (F) TB-2 | 4.0% |
| 3-HB (F) TB-3 | 4.0% |
| 3-HB (F) TB-4 | 4.0% |
| 3-HHB-1 | 4.0% |
| 3-HHB-O1 | 4.0% |
| NI = 91.3 (° C.) | |
| η = 87.0 (mPa · s) | |
| Δn = 0.149 | |
| Δε = 31.3 | |
| Vth = 0.86 (V) | |

Example 5

| | |
|---|---|
| 3-GHH-VFF | 4.0% |
| 3-G2HH-VFF | 4.0% |
| 5-PyB-F | 4.0% |
| 3-PyB (F) -F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-1 | 6.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |
| NI = 94.4 (° C.) | |
| η = 37.3 (mPa · s) | |
| Δn = 0.200 | |
| Δε = 7.1 | |
| Vth = 2.16 (V) | |

Example 6

| | |
|---|---|
| G2HH-VFF | 8.0% |
| 3-GB-C | 10.0% |
| 4-GB-C | 10.0% |
| 2-BEB-C | 12.0% |
| 3-BEB-C | 4.0% |
| 3-PyB (F) -F | 6.0% |
| 4-HEB-O2 | 6.0% |
| 5-HEB-O1 | 6.0% |
| 3-HEB-O2 | 5.0% |
| 5-HEB-O2 | 4.0% |
| 5-HEB-6 | 5.0% |
| 4-HEB-5 | 5.0% |
| 1O-BEB-2 | 4.0% |
| 3-HHB-1 | 6.0% |
| 3-HHEBB-C | 3.0% |
| 3-HBEBB-C | 3.0% |
| 5-HBEBB-C | 3.0% |
| NI = 69.2 (° C.) | |
| η = 43.3 (mPa · s) | |
| Δn = 0.120 | |
| Δε = 12.2 | |
| Vth = 1.26 (V) | |

Example 7

| | |
|---|---|
| 3-GHH-2VFF | 8.0% |
| 3-HB-C | 18.0% |
| 7-HB-C | 3.0% |
| 1O1-HB-C | 10.0% |
| 3-HB (F) -C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-1 | 7.0% |
| 3-HHB-F | 4.0% |
| 3-HHB-O1 | 4.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |
| NI = 79.6 (° C.) | |
| η = 20.0 (mPa · s) | |
| Δn = 0.138 | |
| Δε = 8.7 | |
| Vth = 1.68 (V) | |

Example 8

| | |
|---|---|
| 3-GH-VFF | 7.0% |
| 3-GH-2VFF | 7.0% |
| 3-GHH-VFF | 7.0% |
| 3-GHH-2VFF | 6.0% |
| 2-BEB (F) -C | 5.0% |
| 3-BEB (F) -C | 4.0% |
| 4-BEB (F) -C | 12.0% |
| 1V2-BEB (F, F) -C | 10.0% |
| 3-HH-EMe | 10.0% |
| 3-HB-O2 | 4.0% |
| 7-HEB-F | 2.0% |
| 3-HHEB-F | 2.0% |
| 5-HHEB-F | 2.0% |
| 3-HBEB-F | 4.0% |
| 2O1-HBEB (F) -C | 2.0% |
| 3-HB (F) EB (F) -C | 2.0% |
| 3-HBEB (F, F) -C | 2.0% |
| 3-HHB-F | 4.0% |
| 3-HHB-O1 | 4.0% |
| 3-HEBEB-F | 2.0% |
| 3-HEBEB-1 | 2.0% |

NI = 75.2 (° C.)
η = 41.3 (mPa · s)
Δn = 0.110
Δε = 27.0
Vth = 0.84 (V)

Example 9

| | |
|---|---|
| 3-GH-2VFF | 8.0% |
| 3-GHH-2VFF | 8.0% |
| 2-BEB (F) -C | 5.0% |
| 3-BEB (F) -C | 4.0% |
| 4-BEB (F) -C | 12.0% |
| 1V2-BEB (F, F) -C | 16.0% |
| 3-HB-O2 | 2.0% |
| 3-HH-4 | 3.0% |
| 3-HHB-F | 3.0% |
| 3-HHB-O1 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |
| 3-H2BTB-4 | 4.0% |
| 3-HB (F) TB-2 | 5.0% |

NI = 86.0 (° C.)
η = 41.2 (mPa · s)
Δn = 0.136
Δε = 29.3
Vth = 0.98 (V)

Example 10

| | |
|---|---|
| 1V2-GH-VFF | 6.0% |
| 3-GHH-2VFF | 6.0% |
| 2-BEB-C | 12.0% |
| 3-BEB-C | 4.0% |
| 4-BEB-C | 6.0% |
| 3-HB-C | 28.0% |
| 4-HEB-O2 | 8.0% |
| 5-HEB-O1 | 8.0% |
| 3-HEB-O2 | 6.0% |
| 5-HEB-O2 | 5.0% |
| 3-HHB-1 | 7.0% |
| 3-HHB-O1 | 4.0% |

NI = 65.4 (° C.)
η = 27.2 (mPa · s)
Δn = 0.113
Δε = 11.0
Vth = 1.27 (V)

Example 11

| | |
|---|---|
| 3-GHH-VFF | 7.0% |
| 3-G2HH-VFF | 6.0% |
| 3-GHH-2VFF | 7.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 1O-BEB-2 | 10.0% |
| 1O-EEB-5 | 12.0% |
| 2-HHB-1 | 4.0% |
| 3-HHB-F | 4.0% |
| 3-HHB-O1 | 4.0% |

NI = 67.0 (° C.)
η = 24.8 (mPa · s)
Δn = 0.156
Δε = 7.8
Vth = 1.59 (V)

Example 12

| | |
|---|---|
| 3-GH-VFF | 6.0% |
| 1V2-GH-VFF | 6.0% |
| 3-G2HH-VFF | 7.0% |
| 3-GHH-2VFF | 7.0% |
| 2-HB-C | 5.0% |
| 3-HB-C | 12.0% |
| 3-HB-O2 | 3.0% |
| 2-BTB-1 | 3.0% |
| 3-HHB-1 | 8.0% |
| 3-HHB-F | 4.0% |
| 3-HHB-O1 | 5.0% |
| 3-HHEB-F | 4.0% |
| 5-HHEB-F | 4.0% |
| 2-HHB (F) -F | 7.0% |
| 3-HHB (F) -F | 7.0% |
| 5-HHB (F) -F | 7.0% |
| 3-HHB (F, F) -F | 5.0% |

NI = 98.9 (° C.)
η = 22.3 (mPa · s)
Δn = 0.092
Δε = 6.6
Vth = 2.12 (V)

Example 13

| | |
|---|---|
| 3-GH-2VFF | 10.0% |
| 3-GHH-VFF | 5.0% |
| 3-G2HH-VFF | 5.0% |
| 3-BEB(F)-C | 8.0% |
| 3-HB-C | 8.0% |
| V-HB-C | 8.0% |
| 1V-HB-C | 8.0% |
| 3-HB-O2 | 3.0% |
| 3-HH-2V | 4.0% |
| 3-HH-2V1 | 7.0% |
| V2-HHB-1 | 5.0% |
| 3-HHB-1 | 5.0% |
| 3-HHEB-F | 7.0% |

-continued

| | |
|---|---|
| 3-H2BTB-2 | 6.0% |
| 3-H2BTB-3 | 6.0% |
| 3-H2BTB-4 | 5.0% |
| NI = 90.5 (° C.) | |
| η = 14.5 (mPa · s) | |
| Δn = 0.129 | |
| Δε = 9.8 | |
| Vth = 2.07 (V) | |

Example 14

| | |
|---|---|
| 1V2-GH-VFF | 6.0% |
| 3-GHH-VFF | 4.0% |
| V2-HB-C | 12.0% |
| 1V2-HB-C | 12.0% |
| 3-HB-C | 24.0% |
| 3-HB(F)-C | 5.0% |
| 2-BTB-1 | 2.0% |
| 3-HH-4 | 2.0% |
| 3-HH-VFF | 6.0% |
| 2-HHB-C | 3.0% |
| 3-HHB-C | 6.0% |
| 3-HB(F)TB-2 | 8.0% |
| 3-H2BTB-2 | 5.0% |
| 3-H2BTB-3 | 5.0% |
| NI = 84.1 (° C.) | |
| η = 19.8 (mPa · s) | |
| Δn = 0.149 | |
| Δε = 9.6 | |
| Vth = 1.90 (V) | |

Example 15

| | |
|---|---|
| 3-GH-2VFF | 10.0% |
| 3-GHH-VFF | 5.0% |
| 3-GHH-2VFF | 10.0% |
| 5-BEB(F)-C | 5.0% |
| V-HB-C | 11.0% |
| 5-PyB-C | 6.0% |
| 4-BB-3 | 11.0% |
| 5-HH-V | 11.0% |
| V-HHB-1 | 7.0% |
| 3-HHB-1 | 9.0% |
| 1V2-HBB-2 | 10.0% |
| 3-HHEBH-3 | 5.0% |
| NI = 82.3 (° C.) | |
| η = 19.1 (mPa · s) | |
| Δn = 0.111 | |
| Δε = 6.6 | |
| Vth = 1.98 (V) | |

Example 16

| | |
|---|---|
| 3-GH-VFF | 5.0% |
| 3-GH-2VFF | 5.0% |
| 1V2-GH-VFF | 5.0% |
| 3-GHH-VFF | 6.0% |
| 3-GHH-2VFF | 9.0% |
| 3-G2HH-VFF | 4.0% |
| 1V2-BEB(F,F)-C | 8.0% |
| 3-HB-C | 10.0% |
| V2V-HB-C | 14.0% |
| V2V-HH-3 | 4.0% |
| 3-HB-O2 | 4.0% |
| 3-HHB-1 | 10.0% |

-continued

| | |
|---|---|
| 3-HB(F)TB-2 | 4.0% |
| 3-HB(F)TB-3 | 4.0% |
| 3-H2BTB-2 | 4.0% |
| 3-H2BTB-3 | 4.0% |
| NI = 91.8 (° C.) | |
| η = 25.3 (mPa · s) | |
| Δn = 0.119 | |
| Δε = 10.8 | |
| Vth = 1.82 (V) | |

Example 17

| | |
|---|---|
| 3-GH-VFF | 4.0% |
| 3-GH-2VFF | 7.0% |
| V2-HB-TC | 10.0% |
| 3-HB-TC | 10.0% |
| 3-HB-C | 10.0% |
| 5-HB-C | 7.0% |
| 5-BBC | 30% |
| 2-BTB-1 | 10.0% |
| 2-BTB-O1 | 5.0% |
| 3-HH-4 | 5.0% |
| 3-HHB-1 | 10.0% |
| 3-H2BTB-2 | 3.0% |
| 3-H2BTB-3 | 3.0% |
| 3-HB(F)TB-2 | 3.0% |
| 5-BTB(F)TB-3 | 10.0% |
| NI = 83.9 (° C.) | |
| η = 12.6 (mPa · s) | |
| Δn = 0.196 | |
| Δε = 7.8 | |
| Vth = 1.96 (V) | |

Example 18

| | |
|---|---|
| 3-GH-VFF | 8.0% |
| 3-GH-2VFF | 8.0% |
| 1V2-GH-VFF | 8.0% |
| 3-GHH-2VFF | 11.0% |
| 1V2-BEB(F,F)-C | 6.0% |
| 3-HB-C | 18.0% |
| 2-BTB-1 | 10.0% |
| 5-HH-VFF | 6.0% |
| 1-BHH-VFF | 8.0% |
| 3-H2BTB-2 | 5.0% |
| 3-H2BTB-3 | 4.0% |
| 3-H2BTB-4 | 4.0% |
| 3-HHB-1 | 4.0% |
| NI = 67.7 (° C.) | |
| η = 21.3 (mPa · s) | |
| Δn = 0.123 | |
| Δε = 9.0 | |
| Vth = 1.74 (V) | |

Example 19

| | |
|---|---|
| 3-GH-VFF | 8.0% |
| 3-GH-2VFF | 8.0% |
| 1V2-GH-VFF | 8.0% |
| 3-GHH-VFF | 8.0% |
| 5-HBCF2OB(F,F)-C | 3.0% |
| 3-HB(F,F)CF2OB(F,F)-C | 3.0% |
| 3-HB-C | 18.0% |
| 2-BTB-1 | 10.0% |
| 5-HH-VFF | 6.0% |

-continued

| | |
|---|---|
| 1-BHH-2VFF | 11.0% |
| 3-H2BTB-2 | 5.0% |
| 3-H2BTB-3 | 4.0% |
| 3-H2BTB-4 | 4.0% |
| 3-HHB-1 | 4.0% |

NI = 72.9 (° C.)
η = 20.5 (mPa · s)
Δn = 0.122
Δε = 6.8
Vth = 2.06 (V)

Example 20

| | |
|---|---|
| 3-GHH-VFF | 6.0% |
| 3-G2HH-VFF | 7.0% |
| 2-HHB(F)-F | 17.0% |
| 3-HHB(F)-F | 17.0% |
| 5-HHB(F)-F | 16.0% |
| 2-H2HB(F)-F | 10.0% |
| 3-H2HB(F)-F | 5.0% |
| 5-H2HB(F)-F | 10.0% |
| 2-HBB(F)-F | 6.0% |
| 3-HBB(F)-F | 6.0% |

NI = 108.0 (° C.)
η = 27.4 (mPa · s)
Δn = 0.086
Δε = 5.2
Vth = 2.18 (V)

When adding 0.3 part of CN to 100 parts of the composition described above, the pitch was 78.7 μm.

Example 21

| | |
|---|---|
| 3-GH-VFF | 4.0% |
| 3-GH-2VFF | 4.0% |
| 3-GHH-VFF | 4.0% |
| 3-GHH-2VFF | 4.0% |
| 7-HB(F,F)-F | 3.0% |
| 3-HB-O2 | 7.0% |
| 2-HHB(F)-F | 10.0% |
| 3-HHB(F)-F | 10.0% |
| 5-HHB(F)-F | 10.0% |
| 2-HBB(F)-F | 9.0% |
| 3-HBB(F)-F | 9.0% |
| 2-HBB-F | 4.0% |
| 3-HBB-F | 4.0% |
| 5-HBB-F | 3.0% |
| 3-HBB(F,F)-F | 5.0% |
| 5-HBB(F,F)-F | 10.0% |

NI = 82.1 (° C.)
η = 23.9 (mPa · s)
Δn = 0.102
Δε = 6.0
Vth = 1.95 (V)

Example 22

| | |
|---|---|
| 3-GH-VFF | 6.0% |
| 1V2-GH-VFF | 6.0% |
| 5-HB-CL | 16.0% |
| 3-HH-5 | 4.0% |
| 3-HHB-F | 4.0% |
| 3-HHB-CL | 3.0% |

-continued

| | |
|---|---|
| 4-HHB-CL | 4.0% |
| 3-HHB(F)-F | 10.0% |
| 4-HHB(F)-F | 9.0% |
| 5-HHB(F)-F | 9.0% |
| 7-HHB(F)-F | 8.0% |
| 5-HBB(F)-F | 4.0% |
| 5-HBBH-1O1 | 3.0% |
| 3-HHBB(F,F)-F | 2.0% |
| 4-HHBB(F,F)-F | 3.0% |
| 5-HHBB(F,F)-F | 3.0% |
| 3-HH2BB(F,F)-F | 3.0% |
| 4-HH2BB(F,F)-F | 3.0% |

NI = 106.9 (° C.)
η = 22.2 (mPa · s)
Δn = 0.092
Δε = 5.0
Vth = 2.19 (V)

Example 23

| | |
|---|---|
| 3-GHH-VFF | 5.0% |
| 3-G2HH-VFF | 5.0% |
| G2HH-VFF | 5.0% |
| 3-GHH-2VFF | 5.0% |
| 3-HHB (F, F)-F | 9.0% |
| 3-H2HB (F, F)-F | 8.0% |
| 4-H2HB (F, F)-F | 8.0% |
| 5-H2HB (F, F)-F | 8.0% |
| 3-HBB (F, F)-F | 21.0% |
| 3-H2BB (F, F)-F | 10.0% |
| 5-HHBB (F, F)-F | 3.0% |
| 5-HHEBB-F | 2.0% |
| 3-HH2BB (F, F)-F | 3.0% |
| 4-HBBH-1O1 | 4.0% |
| 5-HBBH-1O1 | 4.0% |

NI = 112.0 (° C.)
η = 36.6 (mPa · s)
Δn = 0.107
Δε = 8.6
V th = 1.80 (V)

When adding 0.25 part of CM-43L to 100 parts of the composition described above, the pitch was 64.2 μm.

Example 24

| | |
|---|---|
| 1V2-GH-VFF | 5.0% |
| 3-GH-2VFF | 5.0% |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB (F, F)-OCF3 | 5.0% |
| 3-HBB (F)-F | 10.0% |
| 3-HH2B (F)-F | 3.0% |
| 3-HB (F) BH-3 | 3.0% |
| 5-HBBH-3 | 3.0% |
| 3-HHB (F, F)-OCF2H | 4.0% |

NI = 76.3 (° C.)
η = 12.8 (mPa · s)
Δn = 0.082
Δε = 4.6
V th = 2.37 (V)

Example 25

| | |
|---|---|
| 3-GHH-VFF | 7.0% |
| 3-GHH-2VFF | 8.0% |
| 2-HHB (F)-F | 3.0% |
| 2-BB (F)-F | 7.0% |
| 3-BB (F)-F | 7.0% |
| 4-HBB (F)-F | 2.0% |
| 2-H2BB (F)-F | 10.0% |
| 3-H2BB (F)-F | 10.0% |
| 3-HBB (F, F)-F | 22.0% |
| 5-HBB (F, F)-F | 6.0% |
| 2-HHB (F, F)-F | 5.0% |
| 3-HHB (F, F)-F | 5.0% |
| 4-HHB (F, F)-F | 5.0% |
| 3-HHB-F | 3.0% |

NI = 105.4 (° C.)
$\eta$ = 35.7 (mPa·s)
$\Delta n$ = 0.129
$\Delta\epsilon$ = 7.3
V th = 1.91 (V)

Example 26

| | |
|---|---|
| 3-GH-VFF | 4.0% |
| 5-HB-CL | 11.0% |
| 3-HH-4 | 4.0% |
| 3-HBB (F, F)-F | 20.0% |
| 5-HBB (F, F)-F | 15.0% |
| 3-HHB (F, F)-F | 8.0% |
| 3-HHEB (F, F)-F | 10.0% |
| 4-HHEB (F, F)-F | 3.0% |
| 5-HHEB (F, F)-F | 3.0% |
| 2-HBEB (F, F)-F | 3.0% |
| 3-HBEB (F, F)-F | 5.0% |
| 5-HBEB (F, F)-F | 3.0% |
| 3-HHBB (F, F)-F | 6.0% |
| 3-HHB-1 | 5.0% |

NI = 77.0 (° C.)
$\eta$ = 23.2 (mPa·s)
$\Delta n$ = 0.103
$\Delta\epsilon$ = 9.1
V th = 1.61 (V)

Example 27

| | |
|---|---|
| 3-GH-2VFF | 4.0% |
| 7-HB (F)-F | 6.0% |
| 5-H2B (F)-F | 6.0% |
| 3-HB-O2 | 4.0% |
| 3-HH-4 | 12.0% |
| 2-HHB (F)-F | 11.0% |
| 3-HHB (F)-F | 11.0% |
| 5-HHB (F)-F | 11.0% |
| 2-HBB (F)-F | 2.0% |
| 3-HBB (F)-F | 2.0% |
| 3-HBB (F, F)-F | 3.0% |
| 2-HHBB (F, F)-F | 4.0% |
| 3-HHBB (F, F)-F | 5.0% |
| 3-HHEB-F | 4.0% |
| 5-HHEB-F | 4.0% |
| 3-HHB-1 | 7.0% |
| 3-HHB-F | 4.0% |

NI = 96.2 (° C.)
$\eta$ = 18.8 (mPa·s)
$\Delta n$ = 0.082
$\Delta\epsilon$ = 4.5
V th = 2.39 (V)

Example 28

| | |
|---|---|
| 3-GH-VFF | 8.0% |
| 3-G2HH-VFF | 8.0% |
| 1V2-GH-VFF | 8.0% |
| 3-GHH-2VFF | 8.0% |
| 3-HH-4 | 4.0% |
| 3-H2HB (F, F)-F | 10.0% |
| 4-H2HB (F, F)-F | 10.0% |
| 5-H2HB (F, F)-F | 8.0% |
| 3-HBB (F, F)-F | 33.0% |
| 3-HHBB (F, F)-F | 3.0% |

NI = 69.8 (° C.)
$\eta$ = 25.4 (mPa·s)
$\Delta n$ = 0.086
$\Delta\epsilon$ = 8.0
V th = 1.54 (V)

Example 29

| | |
|---|---|
| 1V2-GH-VFF | 5.0% |
| 7-HB (F, F)-F | 5.0% |
| 3-H2HB (F, F)-F | 12.0% |
| 4-H2HB (F, F)-F | 10.0% |
| 3-HHB (F, F)-F | 10.0% |
| 3-HBB (F, F)-F | 10.0% |
| 3-HHEB (F, F)-F | 10.0% |
| 4-HHEB (F, F)-F | 3.0% |
| 5-HHEB (F, F)-F | 3.0% |
| 2-HBEB (F, F)-F | 3.0% |
| 3-HBEB (F, F)-F | 5.0% |
| 5-HBEB (F, F)-F | 3.0% |
| 3-HGB (F, F)-F | 15.0% |
| 3-HHBB (F, F)-F | 6.0% |

NI = 72.5 (° C.)
$\eta$ = 33.2 (mPa·s)
$\Delta n$ = 0.084
$\Delta\epsilon$ = 13.1
V th = 1.39 (V)

Example 30

| | |
|---|---|
| 3-GH-VFF | 5.0% |
| 5-H4HB (F, F)-F | 7.0% |
| 5-H4HB-OCF3 | 15.0% |
| 3-H4HB (F, F)-CF3 | 8.0% |
| 5-H4HB (F, F)-CF3 | 10.0% |
| 3-HB-CL | 6.0% |
| 5-HB-CL | 4.0% |
| 2-H2BB (F)-F | 5.0% |
| 3-H2BB (F)-F | 10.0% |
| 5-H2HB (F, F)-F | 5.0% |
| 3-HHB-OCF3 | 5.0% |
| 3-H2HB-OCF3 | 5.0% |
| V-HHB (F)-F | 5.0% |
| 3-HHB (F)-F | 5.0% |
| 3-HBEB (F, F)-F | 5.0% |

NI = 63.4 (° C.)
$\eta$ = 24.5 (mPa·s)
$\Delta n$ = 0.094
$\Delta\epsilon$ = 8.5
V th = 1.72 (V)

Example 31

| | |
|---|---|
| 3-GH-VFF | 5.0% |
| 3-GH-2VFF | 5.0% |
| 5-HB-CL | 17.0% |
| 7-HB (F, F)-F | 3.0% |
| 3-HH-5 | 5.0% |
| 3-HB-O2 | 15.0% |
| 3-H2HB (F, F)-F | 5.0% |
| 4-H2HB (F, F)-F | 5.0% |
| 3-HHB (F, F)-F | 6.0% |
| 2-HHB (F)-F | 7.0% |
| 3-HHB (F)-F | 7.0% |
| 5-HHB (F)-F | 7.0% |
| 3-HHB-1 | 8.0% |
| 3-HHB-O1 | 5.0% |

NI = 63.2 (° C.)
η = 15.1 (mPa · s)
Δn = 0.073
Δε = 3.8
V th = 2.63 (V)

Example 32

| | |
|---|---|
| 3-GHH-2VFF | 3.0% |
| 5-HB-CL | 4.0% |
| 4-HHB (F)-F | 10.0% |
| 5-HHB (F)-F | 9.0% |
| 7-HHB (F)-F | 9.0% |
| 3-HHB (F, F)-F | 8.0% |
| 3-H2HB (F, F)-F | 12.0% |
| 3-HBB (F, F)-F | 22.0% |
| 2-HHBB (F, F)-F | 6.0% |
| 3-GHB (F, F)-F | 3.0% |
| 4-GHB (F, F)-F | 8.0% |
| 5-GHB (F, F)-F | 6.0% |

NI = 82.3 (° C.)
η = 32.1 (mPa · s)
Δn = 0.090
Δε = 8.7
V th = 1.65 (V)

Example 33

| | |
|---|---|
| 3-GHH-VFF | 7.0% |
| 2-HHB (F)-F | 7.0% |
| 3-HHB (F)-F | 8.0% |
| 3-HHB (F, F)-F | 8.0% |
| 3-HBB (F, F)-F | 21.0% |
| 3-H2HB (F, F)-F | 10.0% |
| 3-HHEB (F, F)-F | 10.0% |
| 4-HHEB (F, F)-F | 3.0% |
| 2-HHEB (F, F)-F | 2.0% |
| 3-HBEB (F, F)-F | 3.0% |
| 3-GHB (F, F)-F | 3.0% |
| 4-GHB (F, F)-F | 7.0% |
| 5-GHB (F, F)-F | 7.0% |
| 3-HHBB (F, F)-F | 4.0% |

NI = 82.9 (° C.)
η = 38.5 (mPa · s)
Δn = 0.090
Δε = 10.9
Vth = 1.46 (V)

Example 34

| | |
|---|---|
| 1V2-GH-VFF | 5.0% |
| 7-HB (F)-F | 7.0% |
| 5-HB-CL | 3.0% |
| 3-HH-4 | 4.0% |
| 3-HH-EMe | 23.0% |
| 3-HHEB (F, F)-F | 10.0% |
| 4-HHEB (F, F)-F | 5.0% |
| 3-HHEB-F | 8.0% |
| 5-HHEB-F | 8.0% |
| 4-HGB (F, F)-F | 5.0% |
| 5-HGB (F, F)-F | 6.0% |
| 2-H2GB (F, F)-F | 4.0% |
| 3-H2GB (F, F)-F | 5.0% |
| 5-GHB (F, F)-F | 7.0% |

NI = 77.2 (° C.)
η = 21.3 (mPa · s)
Δn = 0.065
Δε = 6.2
Vth = 2.00 (V)

Example 35

| | |
|---|---|
| 3-GH-VFF | 6.0% |
| 3-GHH-VFF | 6.0% |
| 3-G2HH-VFF | 6.0% |
| 3-GH-2VFF | 6.0% |
| 3-GHH-2VFF | 6.0% |
| 3-H2HB (F, F)-F | 5.0% |
| 5-H2HB (F, F)-F | 5.0% |
| 3-HBB (F, F)-F | 30.0% |
| 5-HBB (F) B-2 | 10.0% |
| 5-HBB (F) B-3 | 10.0% |
| 3-BB (F) B (F, F)-F | 5.0% |
| 5-B2B (F, F) B (F)-F | 5.0% |

NI = 113.4 (° C.)
η = 46.3 (mPa · s)
Δn = 0.133
Δε = 9.5
Vth = 1.78 (V)

Example 36

| | |
|---|---|
| 3-G2HH-VFF | 3.0% |
| 3-HB (F, F) CF2OB (F, F)-F | 11.0% |
| 5-HB (F, F) CF2OB (F, F)-F | 11.0% |
| 5-HB-CL | 7.0% |
| 3-HH-4 | 14.0% |
| 2-HH-5 | 4.0% |
| 3-HHB-1 | 4.0% |
| 3-HHEB-F | 6.0% |
| 5-HHEB-F | 6.0% |
| 3-HHB (F, F)-F | 6.0% |
| 3-HHEB (F, F)-F | 8.0% |
| 4-HHEB (F, F)-F | 3.0% |
| 5-HHEB (F, F)-F | 2.0% |
| 2-HBEB (F, F)-F | 3.0% |
| 3-HBEB (F, F)-F | 3.0% |
| 5-HBEB (F, F)-F | 3.0% |
| 2-HHBB (F, F)-F | 3.0% |
| 3-HHBB (F, F)-F | 3.0% |

NI = 83.3 (° C.)
η = 21.1 (mPa · s)
Δn = 0.079
Δε = 8.2
Vth = 1.71 (V)

Example 37

| | |
|---|---|
| 3-GHH-VFF | 4.0% |
| 3-BB (F, F) CF2OB (F, F)-F | 35.0% |
| 3-HH-4 | 4.0% |
| 3-HHB (F, F)-F | 10.0% |
| 3-H2HB (F, F)-F | 9.0% |
| 3-HBB (F, F)-F | 15.0% |
| 2-HHBB (F, F)-F | 3.0% |
| 3-HHBB (F, F)-F | 3.0% |
| 3-HH2BB (F, F)-F | 4.0% |
| 3-HHB-1 | 6.0% |
| 5-HBBH-1O1 | 7.0% |
| NI = 84.2 (° C.) | |
| η = 31.0 (mPa · s) | |
| Δn = 0.117 | |
| Δε = 12.7 | |
| Vth = 1.37 (V) | |

Example 38

| | |
|---|---|
| 3-GH-VFF | 7.0% |
| 1V2-GH-VFF | 7.0% |
| 3-HEB-O4 | 28.0% |
| 4-HEB-O2 | 20.0% |
| 5-HEB-O1 | 20.0% |
| 3-HEB-O2 | 18.0% |
| NI = 65.0 (° C.) | |
| η = 17.0 (mPa · s) | |
| Δn = 0.084 | |

Example 39

| | |
|---|---|
| 3-GHH-2VFF | 6.0% |
| 3-HH-2 | 5.0% |
| 3-HH-O1 | 4.0% |
| 3-HH-O3 | 5.0% |
| 5-HH-O1 | 4.0% |
| 3-HB (2F, 3F)-O2 | 12.0% |
| 5-HB (2F, 3F)-O2 | 11.0% |
| 3-HHB (2F, 3F)-O2 | 14.0% |
| 5-HHB (2F, 3F)-O2 | 15.0% |
| 3-HHB (2F, 3F)-2 | 24.0% |
| NI = 91.0 (° C.) | |
| Δn = 0.083 | |
| Δε = -3.4 | |

Example 40

| | |
|---|---|
| 3-GH-2VFF | 5.0% |
| 3-HH-5 | 5.0% |
| 3-HH-O1 | 6.0% |
| 3-HH-O3 | 6.0% |
| 3-HB-O1 | 5.0% |
| 3-HB-O2 | 5.0% |
| 3-HB (2F, 3F)-O2 | 10.0% |
| 5-HB (2F, 3F)-O2 | 10.0% |
| 3-HHB (2F, 3F)-O2 | 12.0% |
| 5-HHB (2F, 3F)-O2 | 13.0% |
| 3-HHB (2F, 3F)-2 | 4.0% |
| 2-HHB (2F, 3F)-1 | 4.0% |
| 3-HHEH-3 | 5.0% |
| 3-HHEH-5 | 5.0% |
| 4-HHEH-3 | 5.0% |
| NI = 82.2 (° C.) | |

Δn = 0.077
Δε = -2.8

INDUSTRIAL APPLICABILITY

The compounds of the present invention, that is, the di- to tetracyclic compounds having a hetero ring structure and containing a difluorovinyl group at a terminal are physically and chemically very stable under conditions on which a display is used. It is characterized by having a wide liquid crystal phase temperature range, a good solubility in a liquid crystal composition even at a low temperature, low viscosity, suitable dielectric anisotropy and a large elastic constant ratio $K_{33}/K_{11}$. Further, use of the compound of the present invention for the structural component makes it possible, as shown in the examples, to provide a liquid crystal composition and a liquid crystal display which have good characteristics and are novel. Further, the synthetic intermediate is very useful in synthesizing the compound of the present invention.

What is claimed is:

1. A difluorovinyl compound represented by Formula (1):

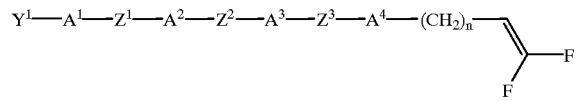

(1)

wherein $Y^1$ represents H or a straight chain or branched alkyl group having 1 to 10 carbon atoms, and optional —$CH_2$— in the above alkyl group may be replaced by —O— or —CH=CH—, but —O— is not adjacent to each other, and at least one H in $Y^1$ may be substituted with halogen or a cyano group; $A^1$, $A^2$, $A^3$ and $A^4$ each independently represent 1,4-cyclohexylene in which optional —$CH_2$— which is not adjacent to each other may be replaced by —O—, 1,4-phenylene in which optional H may be substituted with halogen, and a single bond, in which at least two of $A^1$, $A^2$, $A^3$ and $A^4$ have the ring structure described above, and at least one of them is 1,4-cyclohexylene in which —$CH_2$— is replace by —O—; $Z^1$, $Z^2$ and $Z^3$ each independently represent a single bond, —$(CH_2)_2$—, —CH=CH—, —$(CH_2)_4$—, —$O(CH_2)_3$— or —$(CH_2)_3O$—; n represents 0 or an integer of 1 to 10, provided that when any of $A^1$, $A^2$, $A^3$ and $A^4$ is 1,4-phenylene, $Z^1$, $Z^2$ and $Z^3$ are single bonds, and among them, when $A^4$ is 1,3-dioxane-2,5-diyl and $A^2$ is 1,4-phenylene and when $A^3$ is 1,4-cyclohexylene and $A^4$ is a single bond, $Y^1$ is H, and n is not 0.

2. A difluorovinyl compound as described in claim 1, wherein $A^1$, $A^2$, $A^3$ and $A^4$ each independently represent 1,4-cyclohexylene in which optional —$CH_2$— which is not adjacent to each other may be replaced by —O—, 1,4-phenylene and a single bond, in which at least two of $A^1$, $A^2$, $A^3$ and $A^4$ have the ring structure described above, and at least one of them is 1,4-cyclohexylene in which —$CH_2$— is replaced by —O—; $Z^1$, $Z^2$ and $Z^3$ each independently represent a single bond, —$(CH_2)_2$— or —$(CH_2)_4$—, provided that when any of $A^1$, $A^2$, $A^3$ and $A^4$ is 1,4-phenylene, $Z^1$, $Z^2$ and $Z^3$ are single bonds, and among them, when $A^1$ is 1,3-dioxane-2,5-diyl and $A^2$ is 1,4-phenylene and when $A^3$ is 1,4-cyclohexylene and $A^4$ is a single bond, $Y^1$ is H, and n is not 0.

3. A difluorovinyl compound as described in claim 1, wherein $A^1$ is 1,3-dioxane-2,5-diyl; $A^2$ is 1,4-cyclohexylene; and $A^3$, $A^4$, $Z^1$, $Z^2$ and $Z^3$ are single bonds.

4. A difluorovinyl compound as described in claim 1, wherein either one of $A^1$ and $A^2$ is 1,3-dioxane-2,5-diyl, and the other is 1,4-cyclohexylene; $A^3$ is 1,4-cyclohexylene; and $A^4$, $Z^1$, $Z^2$ and $Z^3$ are single bonds.

5. A difluorovinyl compound as described in claim 1, wherein either one of $A^1$, $A^2$ and $A^3$ is 1,3-dioxane-2,5-diyl, and the remaining two are 1,4-cyclohexylenes; $A^4$ is 1,4-cyclohexylene; and $Z^1$, $Z^2$ and $Z^3$ are single bonds.

6. A difluorovinyl compound as described in claim 1, wherein $A^1$ is 1,3-dioxane-2,5-diyl; $A^2$ is 1,4-cyclohexylene; $Z^1$ is —(CH$_2$)$_2$— or —(CH$_2$)$_4$—; and $A^3$, $A^4$, $Z^2$ and $Z^3$ are single bonds.

7. A difluorovinyl compound as described in claim 1, wherein either one of $A^1$ and $A^2$ is 1,3-dioxane-2,5-diyl, and the other is 1,4-cyclohexylene; $A^3$ is 1,4-cyclohexylene; either one of $Z^1$ and $Z^2$ is —(CH$_2$)$_2$— or —(CH$_2$)$_4$—, and the other is a single bond; and $A^4$, $Z^1$, $Z^2$ and $Z^3$ are single bonds.

8. A difluorovinyl compound as described in claim 1, wherein either one of $A^1$, $A^2$ and $A^3$ is 1,3-dioxane-2,5-diyl, and the remaining two are 1,4-cyclohexylenes; A is 1,4-cyclohexylene; and either one of $Z^1$, $Z^2$ and $Z^3$ is —(CH$_2$)$_2$— or —(CH$_2$)$_4$—, and the remaining two are single bonds.

9. A liquid crystal composition comprising at least one difluorovinyl compound as described in claim 1.

10. A liquid crystal composition comprising at least one difluorovinyl compound as described in claim 1 as a first component and at least one compound selected from the group consisting of compounds represented by Formulas (2), (3) and (4) as a second component:

(2)

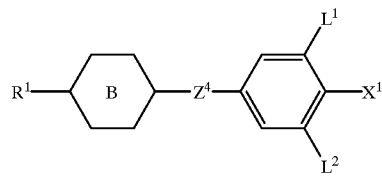

(3)

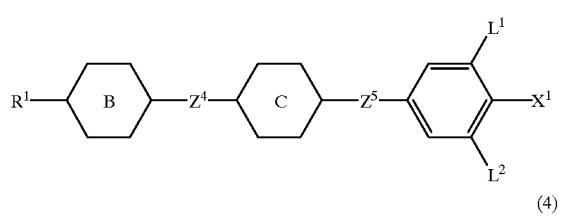

(4)

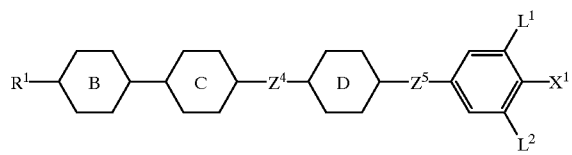

wherein $R^1$ represents an alkyl group having 1 to 10 carbon atoms, in which optional —CH$_2$— in this alkyl group may be replaced by —O— or —CH=CH—, but —O— is not adjacent to each other and in which optional H in this group may be substituted with F; $X^1$ represents F, Cl, —OCF$_3$, —OCF$_2$H, —CF$_3$, CF$_2$H, —CFH$_2$, —OCF$_2$CF$_2$H or —OCF$_2$CFHCF$_3$; $L^1$ and $L^2$ each independently represent H or F; $Z^4$ and $Z^5$ each independently represent —(CH$_2$)$_2$—, —(CH$_2$)$_4$—, —COO—, —CF$_2$O—, —OCF$_2$—, —CH=CH— or a single bond; a ring B and a ring C each independently represent 1,4-cyclohexylene, 1,3-dioxane-2,5-diyl or 1,4-phenylene in which H may be substituted with F; and a ring D represents 1,4-cyclohexylene or 1,4-phenylene in which H may be substituted with F.

11. A liquid crystal composition comprising at least one difluorovinyl compound as described in claim 1 as the first component and at least one compound selected from the group consisting of compounds represented by Formulas (5) and (6) as a second component:

(5)

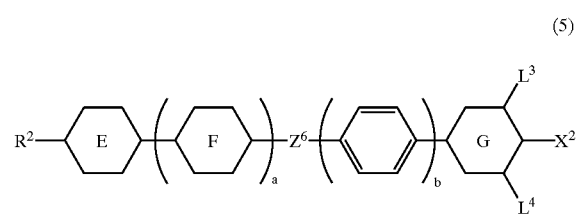

(6)

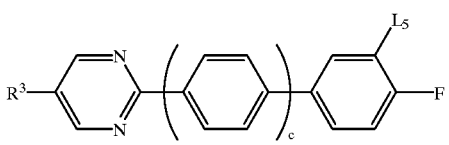

wherein $R^2$ and $R^3$ each independently represent an alkyl group having 1 to 10 carbon atoms, in which optional —CH$_2$— in these alkyl groups may be replaced by —O— or —CH=CH—, but —O— is not adjacent to each other and in which optional H in these alkyl groups may be substituted with F; $X^2$ represents —CN or —C≡C—CN; a ring E represents 1,4-cyclohexylene, 1,4-phenylene, 1,3-dioxane-2,5-diyl or pyrimidine-2,5-diyl; a ring F represents 1,4-cyclohexylene, 1,4-phenylene in which H may be substituted with F or pyrimidine-2,5-diyl; a ring G represents 1,4-cyclohexylene or 1,4-phenylene; $Z^6$ represents —(CH$_2$)$_2$—, —COO—, —CF$_2$O—, —OCF$_2$— or a single bond; $L^3$, $L^4$ and $L^5$ each independently represent H or F; and a, b and c each independently represent 0 or 1.

12. A liquid crystal composition comprising at least one difluorovinyl compound as described in claim 1 as the first component and at least one compound selected from the group consisting of compounds represented by Formulas (7), (8) and (9) as a second component:

(7)

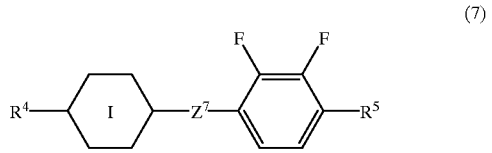

(8)

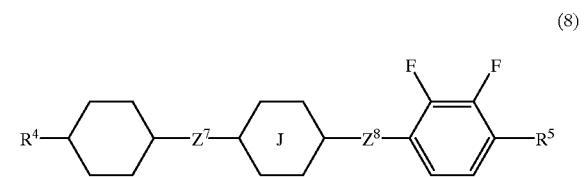

(9)

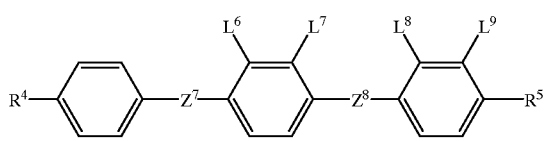

(10)

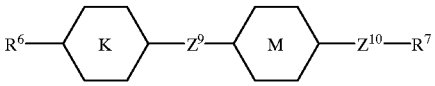

(11)

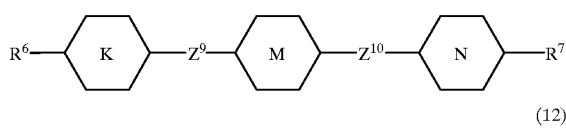

(12)

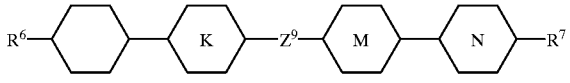

wherein $R^4$ and $R^5$ each independently represent an alkyl group having 1 to 10 carbon atoms, in which optional —CH$_2$— in this alkyl group may be replaced by —O— or —CH═CH—, but —O— is not adjacent to each other and in which optional H in this alkyl group may be substituted with F; a ring I and a ring J each independently represent 1,4-cyclohexylene or 1,4-phenylene; $L^6$, $L^7$, $L^8$ and $L^9$ each independently represent H or F, but all are not H at the same time; and $Z^7$ and $Z^8$ each independently represent —(CH$_2$)$_2$—, —COO— or a single bond.

13. A liquid crystal composition comprising at least one difluorovinyl compound as described in claim 1 as the first component, at least one compound selected from the group consisting of the compounds represented by Formulas (2), (3) and (4) as the second component:

(2)

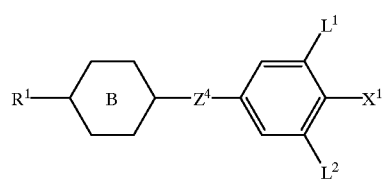

(3)

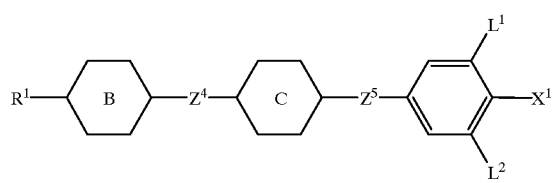

(4)

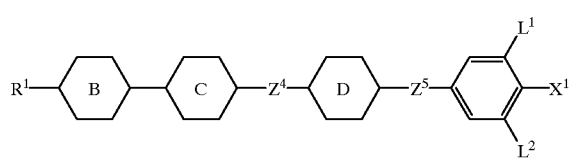

wherein $R^1$ represents an alkyl group having 1 to 10 carbon atoms, in which optional —CH$_2$— in this alkyl group may be replaced by —O— or —CH═CH—, but —O— is not adjacent to each other and in which optional H in this group may be substituted with F; $X^1$ represents F, Cl, —OCF$_3$, —OCF$_2$H, —CF$_3$, —CF$_2$H, —CFH$_2$, —OCF$_2$CF$_2$H or —OCF$_2$CFHCF$_3$; $L^1$ and $L^2$ each independently represent H or F; $Z^4$ and $Z^5$ each independently represent —(CH$_2$)$_2$—, —(CH$_2$)$_4$—, —COO—, —CF$_2$O—, —OCF$_2$—, —CH═CH— or a single bond; a ring B and a ring C each independently represent 1,4-cyclohexylene, 1,3-dioxane-2, 5-diyl or 1,4-phenylene in which H may be substituted with F; and a ring D represents 1,4-cyclohexylene or 1,4-phenylene in which H may be substituted with F;

and at least one compound selected from the group consisting of compounds represented by Formulas (10), (11) and (12) as a third component:

wherein $R^6$ and $R^7$ each independently represent an alkyl group having 1 to 10 carbon atoms, in which optional —CH$_2$— in this alkyl group may be replaced by —O— or —CH═CH—, but —O— is not adjacent to each other and in which optional H in this alkyl group may be substituted with F; a ring K, a ring M and a ring N each independently represent 1,4-cyclohexylene, pyrimidine-2,5-diyl or 1,4-phenylene in which H may be substituted with F; and $Z^9$ and $Z^{10}$ each independently represent —C≡C—, —COO—, —(CH$_2$)$_2$—, —CH═CH— or a single bond.

14. A liquid crystal composition comprising at least one difluorovinyl compound as described in claim 1 as the first component, at least one compound selected from the group consisting of the compounds represented by Formulas (5) and (6) as the second component:

(5)

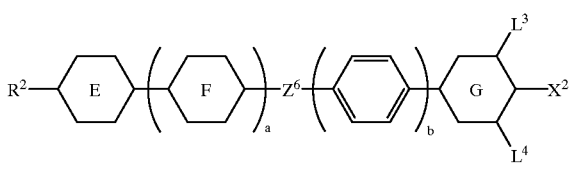

(6)

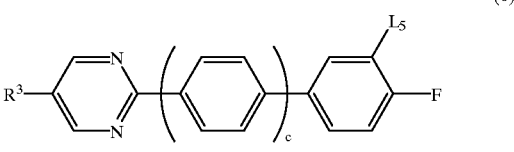

wherein $R^2$ and $R^3$ each independently represent an alkyl group having 1 to 10 carbon atoms, in which optional —CH$_2$— in these alkyl groups may be replaced by —O— or —CH═CH—, or —O— is not adjacent to each other and in which optional H in these alkyl groups may be substituted with F; $X^2$ represents —CN or —C≡C—CN; a ring F represents 1,4-cyclohexylene, 1,4-phenylene, 1,3-dioxane-2,5-diyl or pyrimidine-2,5-diyl; a ring F represents 1,4-cyclohexylene, 1,4-phenylene in which H may be substituted with F or pyrimidine-2,5-diyl; a ring G represents 1,4-cyclohexylene or 1,4-phenylene; $Z^6$ represents —(CH$_2$)$_2$—, —COO—, —CF$_2$O—, —OCF$_2$— or a single bond; $L^3$, $L^4$ and $L^5$ each independently represent H or F; and a, b and c each independently represent 0 or 1;

and at least one compound selected from the group consisting of the compounds represented by Formulas (10), (11) and (12) as the third component:

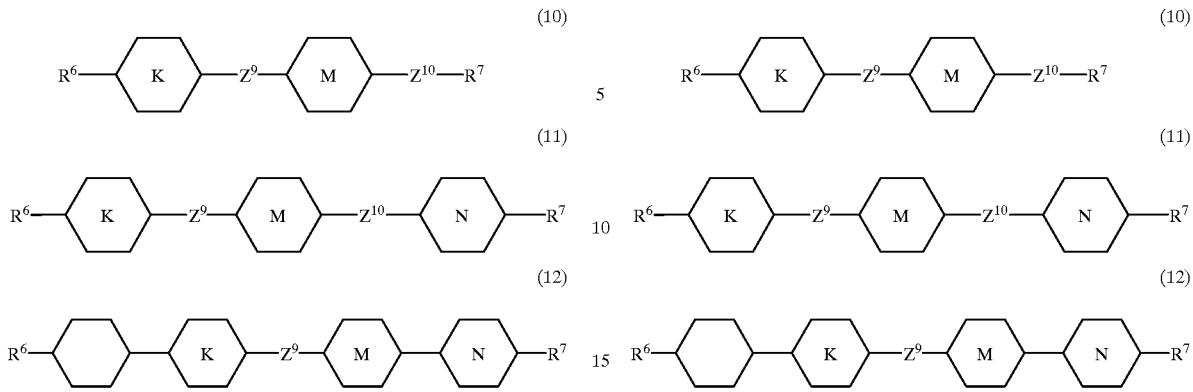

(10)

(11)

(12)

wherein $R^6$ and $R^7$ each independently represent an alkyl group having 1 to 10 carbon atoms, in which optional —$CH_2$— in this alkyl group may be replaced by —O— or —CH=CH—, but —O— is not adjacent to each other and in which optional H in this alkyl group may be substituted with F; a ring K, a ring M and a ring N each independently represent 1,4-cyclohexylene, pyrimidine-2,5-diyl or 1,4-phenylene in which H may be substituted with F; and $Z^9$ and $Z^{10}$ each independently represent —C≡C—, —COO—, —$(CH_2)_2$—, —CH=CH— or a single bond.

15. A liquid crystal composition comprising at least one difluorovinyl compound as described in claim 1 as the first component, at least one compound selected from the group consisting of the compounds represented by Formulas (7), (8) and (9) as the second component:

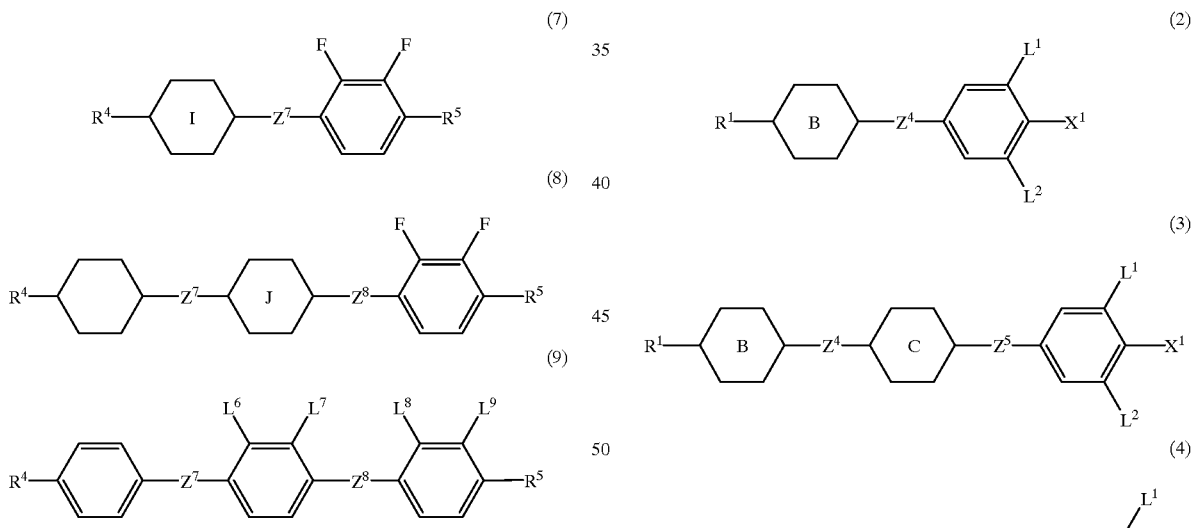

(7)

(8)

(9)

wherein $R^4$ and $R^5$ each independently represent an alkyl group having 1 to 10 carbon atoms, in which optional —$CH_2$— in this alkyl group may be replaced by —O— or —CH=CH—, but —O— is not adjacent to each other and in which optional H in this alkyl group may be substituted with F; a ring I and a ring J each independently represent 1,4-cyclohexylene or 1,4-phenylene; $L^6$, $L^7$, $L^8$ and $L^9$ each independently represent H or F, but all are not H at the same time; and $Z^7$ and $Z^8$ each independently represent —$(CH_2)_2$—, —COO— or a single bond;

and at least one compound selected from the group consisting of the compounds represented by Formulas (10), (11) and (12) as the third component:

wherein $R^6$ and $R^7$ each independently represent an alkyl group having 1 to 10 carbon atoms, in which optional —$CH_2$— in this alkyl group may be replaced by —O— or —CH=CH—, but —O— is not adjacent to each other and in which optional H in this alkyl group may be substituted with F; a ring K, a ring M and a ring N each independently represent 1,4-cyclohexylene, pyrimidine-2,5-diyl or 1,4-phenylene in which H may be substituted with F; and $Z^9$ and $Z^{10}$ each independently represent —C≡C—, —COO—, —$(CH_2)_2$—, —CH=CH— or a single bond.

16. A liquid crystal composition comprising at least one difluorovinyl compound as described in claim 1 as the first component, at least one compound selected from the group consisting of the compounds represented by Formulas (2), (3) and (4) as the second component:

(2)

(3)

(4)

wherein $R^1$ represents an alkyl group having 1 to 10 carbon atoms, in which optional —$CH_2$— in this alkyl group may be replaced by —O— or —CH=CH—, but —O— is not adjacent to each other and in which optional H in this group may be substituted with F; $X^1$ represents F, Cl, —$OCF_3$, —$OCF_2H$, —$CF_3$, —$CF_2H$, —$CFH_2$, —$OCF_2CF_2H$ or —$OCF_2CFHCF_3$; $L^1$ and $L^2$ each independently represent H or F; $Z^4$ and $Z^5$ each independently represent —$(CH_2)_2$—, —$(CH_2)_4$—, —COO—, —$CF_2O$—, —$OCF_2$—, —CH=CH— or a single bond; a ring B and a ring C each independently represent 1,4-cyclohexylene, 1,3-dioxane-2,5-diyl or 1,4-phenylene in which H may be substituted with F; and a ring D represents 1,4-cyclohexylene or 1,4-phenylene in which H may be substituted with F;

at least one compound selected from the group consisting of the compounds represented by Formulas (5) and (6) as the third component:

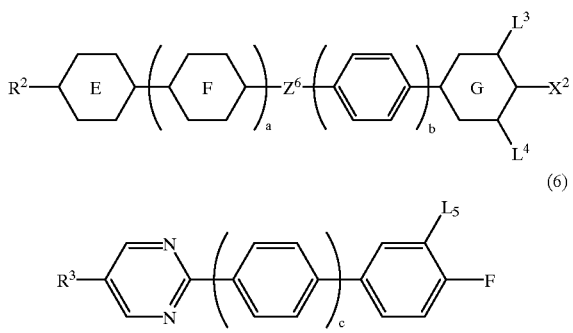

(5)

(6)

wherein $R^2$ and $R^3$ each independently represent an alkyl group having 1 to 10 carbon atoms, in which optional —CH$_2$— in these alkyl groups may be replaced by —O— or —CH=CH—, but —O— is not adjacent to each other and in which optional H in these alkyl groups may be substituted with F; $X^2$ represents —CN or —C≡C—CN; a ring E represents 1,4-cyclohexylene, 1,4-phenylene, 1,3-dioxane-2,5-diyl or pyrimidine-2,5-diyl; a ring F represents 1,4-cyclohexylene, 1,4-phenylene in which H may be substituted with F or pyrimidine-2,5-diyl; a ring G represents 1,4-cyclohexylene or 1,4-phenylene; $Z^6$ represents —(CH$_2$)$_2$—, —COO—, —CF$_2$O—, —OCF$_2$— or a single bond; $L^3$, $L^4$ and $L^5$ each independently represent H or F; and a, b and c each independently represent 0 or 1;

and at least one compound selected from the group consisting of the compounds represented by Formulas (10), (11) and (12) as the fourth component:

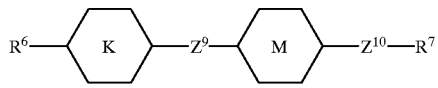

(10)

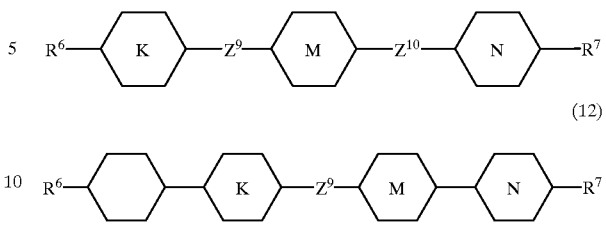

(11)

(12)

wherein $R^6$ and $R^7$ each independently represent an alkyl group having 1 to 10 carbon atoms, in which optional —CH$_2$— in this alkyl group may be replaced by —O— or —CH=CH—, but —O— is not adjacent to each other and in which optional H in this alkyl group may be substituted with F; a ring K, a ring M and a ring N each independently represent 1,4-cyclohexylene, pyrimidine-2,5-diyl or 1,4-phenylene in which H may be substituted with F; and $Z^9$ and $Z^{10}$ each independently represent —C≡C—, —COO—, —(CH$_2$)$_2$—, —CH=CH— or a single bond.

17. A liquid crystal composition comprising at least one liquid crystal composition as described in claim 9 and further comprising at least one optically active compound.

18. A liquid crystal display constituted with the liquid crystal composition as described in claim 9.

19. A difluorovinyl compound represented by Formula (13):

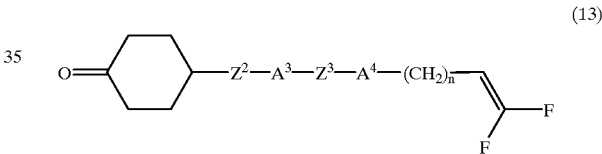

(13)

wherein $A^3$ and $A^4$ each independently represent 1,4-cyclohexylene in which optional —CH$_2$— may be replaced by —O—, 1,4-phenylene in which optional H may be substituted with halogen, and a single bond; $Z^2$ and $Z^3$ each independently represent a single bond, —(CH$_2$)$_2$—, —CH=CH—, —(CH$_2$)$_4$—, —O(CH$_2$)$_3$— or —(CH$_2$)$_3$O; and n represents 0 or an integer of 1 to 10.

* * * * *